US010392635B2

(12) United States Patent
Poulos et al.

(10) Patent No.: US 10,392,635 B2
(45) **Date of Patent: *Aug. 27, 2019**

(54) PRODUCTION OF TETRAHYDROCANNABINOLIC ACID IN YEAST

(71) Applicant: Librede Inc., Sherman Oaks, CA (US)

(72) Inventors: Jason L. Poulos, Los Angeles, CA (US); Anthony N. Farnia, Pasadena, CA (US)

(73) Assignee: Librede Inc., Sherman Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/122,702

(22) Filed: Sep. 5, 2018

(65) Prior Publication Data

US 2018/0371507 A1 Dec. 27, 2018

Related U.S. Application Data

(63) Continuation of application No. 15/815,651, filed on Nov. 16, 2017, now Pat. No. 10,093,949, which is a (Continued)

(51) Int. Cl.

| | |
|---|---|
| ***C12P 7/42*** | (2006.01) |
| ***C12N 1/14*** | (2006.01) |
| ***C12N 15/00*** | (2006.01) |
| ***C12N 9/88*** | (2006.01) |
| ***C12N 9/10*** | (2006.01) |
| ***C12N 9/00*** | (2006.01) |

(Continued)

(52) U.S. Cl.

CPC .............. *C12P 7/42* (2013.01); *C12N 9/1029* (2013.01); *C12N 9/1085* (2013.01); *C12N 9/88* (2013.01); *C12N 9/93* (2013.01); *C12N 15/81* (2013.01); *C12Y 203/01206* (2015.07); *C12Y 205/01* (2013.01); *C12Y 504/99* (2013.01); *C12Y 602/01* (2013.01)

(58) Field of Classification Search

None

See application file for complete search history.

(56) References Cited

U.S. PATENT DOCUMENTS

| | | | |
|---|---|---|---|
| 6,630,507 | B1 | 10/2003 | Hampson et al. |
| 7,186,850 | B2 | 3/2007 | Silverberg |

(Continued)

FOREIGN PATENT DOCUMENTS

| | | |
|---|---|---|
| WO | WO2013006953 | 1/2013 |
| WO | WO2014134281 | 9/2014 |
| WO | WO2016010827 | 1/2016 |

OTHER PUBLICATIONS

Gagne, S.J. et al. Identification of olivetolic acid cyclase from Cannabis sativa reveals a unique catalytic route to plant polyketides. Proceedings of the National Academy of Sciences of the United States of America 109, 12811-12816 (2012).

(Continued)

*Primary Examiner* — Yong D Pak

(74) *Attorney, Agent, or Firm* — Carr & Ferrell LLP

(57) ABSTRACT

Exemplary embodiments provided herein include genetically engineering microorganisms, such as yeast or bacteria, to produce cannabinoids by inserting genes that produce the appropriate enzymes for the metabolic production of a desired compound.

3 Claims, 8 Drawing Sheets

Specification includes a Sequence Listing.

Related U.S. Application Data continuation of application No. 14/795,816, filed on Jul. 9, 2015, now Pat. No. 9,822,384.

(60) Provisional application No. 62/024,099, filed on Jul. 14, 2014.

(51) Int. Cl.
*C07H 21/04* (2006.01)
*C12N 15/81* (2006.01)

(56) References Cited

U.S. PATENT DOCUMENTS

| | | | | |
|---|---|---|---|---|
| 8,673,368 | B2 | 3/2014 | Guy et al. | |
| 8,884,100 | B2 | 11/2014 | Page et al. | |
| 9,611,460 | B2 | 4/2017 | Page et al. | |
| 9,822,384 | B2 | 11/2017 | Poulos et al. | |
| 10,093,949 | B2 | 10/2018 | Poulos et al. | |
| 2009/0226991 | A1 | 9/2009 | Feldman et al. | |
| 2012/0144523 | A1* | 6/2012 | Page .................... | C12N 9/1085 800/278 |
| 2013/0067619 | A1 | 3/2013 | Page et al. | |
| 2013/0210107 | A1 | 8/2013 | Akada et al. | |
| 2014/0178954 | A1 | 6/2014 | Hitz et al. | |
| 2016/0010126 | A1 | 1/2016 | Poulos et al. | |
| 2018/0073043 | A1 | 3/2018 | Poulos et al. | |

OTHER PUBLICATIONS

Stout, J.M., Boubakir, Z., Ambrose, S.J., Purves, R.W. & Page, J.E. The hexanoyl-CoA precursor for cannabinoid biosynthesis is formed by an acyl-activating enzyme in Cannabis sativa trichomes. The Plant Journal 71, 353-365 (2012).

Shoyama, Y. et al. Structure and function of 1-Tetrahydrocannabinolic Acid (THCA) synthase, the enzyme controlling the psychoactivity of cannabis sativa. J. Mol. Biol., 423 (1), 96-105 (2012).

ElSohly et al. Chemical constituents of marijuana: The complex mixture of natural cannabinoids. National Center for Natural Products Research, School of Pharmacy, The University of Mississippi, University, MS 38677. Life Sciences (78), 539-548 (2005).

Ignea et al. Engineering monoterpene production in yeast using a synthetic dominant negative geranyl diphosphate synthase. ACS Synth Biol, May 16, 2014. vol. 3, No. 5. pp. 298-306.

Fonseca et al. The yeast *Kluyveromyces marxianus* and its biotechnological potential. Appl Microbiol Biotechnol, Jun. 2008, vol. 79, No. 3, pp. 339-354.

International Search Report and Written Opinion dated Dec. 28, 2015 in Patent Cooperation Treaty Application No. PCT/US2015/039812, filed Jul. 9, 2015, 21 pages.

"Recombinase expression vector pSH68, complete sequence", GenBank entry HQ401270.1, [retrieved on Nov. 18, 2015 from http://www.ncbi.nlm.nih.gov/nuccore/HW401270] Sep. 12, 2011 (Sep. 12, 2011), 3 pages.

Written Opinion of the International Preliminary Examining Authority dated Jun. 24, 2016 in Patent Cooperation Treaty Application No. PCT/US2015/039812, filed Jul. 9, 2015, 5 pages.

Fischer, Marc et al., Metabolic Engineering of Monoterpene Synthesis in Year, Biotechnology and Bioengineering, vol. 108, No. 8, Aug. 2011, 10 pages.

"Office Action," Canada Patent Application No. 2990071, dated Oct. 30, 2018, 4 pages.

* cited by examiner

Librede's Pathway from Glucose to CBD

SEQUENCE LISTING

```
<160> NUMBER OF SEQ ID NOS: 53

<210> SEQ ID NO 1
<211> LENGTH: 7969
<212> TYPE: DNA
<213> ORGANISM: Artificial Sequence
<220> FEATURE:
<223> OTHER INFORMATION: Codon optimized

<400> SEQUENCE: 1

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

ttttttttt ccccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctactg gcgcgtggag    840

taaaaaggtt tggatcagga tttgcgcctt tggatgaggc actttccaga gcggtggtag    900

atctttcgaa caggccgtac gcagttgtcg aacttggttt gcaaagggag aaagtaggag    960
```

-continued

```
atctctcttg cgagatgatc ccgcattttc ttgaaagctt tgcagaggct agcagaatta   1020

ccctccacgt tgattgtctg cgaggcaaga atgatcatca ccgtagtgag agtgcgttca   1080

aggctcttgc ggttgccata agagaagcca cctcgcccaa tggtaccaac gatgttccct   1140

ccaccaaagg tgttcttatg tagtgacacc gattatttaa agctgcagca tacgatatat   1200

atacatgtgt atatatgtat acctatgaat gtcagtaagt atgtatacga acagtatgat   1260

actgaagatg acaaggtaat gcatcattct atacgtgtca ttctgaacga ggcgcgcttt   1320

ccttttttct tttgctttt tcttttttt tctcttgaac tcgacggatc tatgcggtgt   1380

gaaataccgc acagatgcgt aaggagaaaa taccgcatca ggaaattgta aacgttaata   1440

ttttgttaaa attcgcgtta aatttttgtt aaatcagctc atttttaac caataggccg   1500

aaatcggcaa aatcccttat aaatcaaaag aatagaccga gatagggttg agtgttgttc   1560

cagtttggaa caagagtcca ctattaaaga acgtggactc caacgtcaaa gggcgaaaaa   1620

ccgtctatca gggcgatggc ccactacgtg aaccatcacc ctaatcaagt tttttggggt   1680

cgaggtgccg taaagcacta aatcggaacc ctaaagggag cccccgattt agagcttgac   1740

ggggaaagcc ggcgaacgtg gcgagaaagg aagggaagaa agcgaaagga gcgggcgcta   1800

gggcgctggc aagtgtagcg gtcacgctgc gcgtaaccac cacacccgcc gcgcttaatg   1860

cgccgctaca gggcgcgtcg cgccattcgc cattcaggct gcgcaactgt tgggaagggc   1920

gatcggtgcg ggcctcttcg ctattacgcc agctggcgaa agggggatgt gctgcaaggc   1980

gattaagttg ggtaacgcca gggttttccc agtcacgacg ttgtaaaacg acggccagtg   2040

agcgcgcgta atacgactca ctatagggcg aattgggtac cggccgcaaa ttaaagcctt   2100

cgagcgtccc aaaaccttct caagcaaggt tttcagtata atgttacatg cgtacacgcg   2160

tctgtacaga aaaaaaagaa aaatttgaaa tataaataac gttcttaata ctaacataac   2220

tataaaaaaa taaataggga cctagacttc aggttgtcta actccttcct tttcggttag   2280

agcggatgtg gggggagggc gtgaatgtaa gcgtgacata actaattaca tgactcgagg   2340

tcgactcatt cgaaatgact gaattgttgt ctcaaaactc ttctcatgat cttgtttgtt   2400

gcagttctag gtaaggatga caatgggaca actctagtaa ctttgaataa tgggttcaat   2460

ttcttttgca aacccaagtt aaaggataat ctcaattggt tcaaatcaat ggttgtgtcg   2520

tttgaatcct tcaatacgaa aaatatgacc aattgttctg gaccaccacc caaaggtgga   2580

acaccaatag cagtggtttc aaaaactctg tcatctactt cattacagac tctttcgatt   2640

tcgatagaac taattttgat accaccgatg ttcatagtgt catcggctct accgtgtgca   2700

tggtagtaac cgttagaggt caattcgaaa atgtcaccat gtcttctcaa tacttcacca   2760

ttcaaggttg gcataccctt gaaatagaca tcgtgatgat taccgtttaa caatgttttt   2820

gaggcaccaa acataacagg acctaatgcc aattcaccga tacctggctt atttttaggc   2880

attgggtaac cgttcttatc taatatgtac aaggtgcaac ccatacattg ggatgaaaaa   2940

gaacttaaag attgagcttg caaaaatgaa ccagcagaaa aagcaccacc gatttctgta   3000

ccaccacaca tttctataac tggcttgtag ttagctctac ccattaacca caaatattcg   3060

tctacattag aggcttcacc ggatgaagaa aagcatctta tggtggacca atcgtaacct   3120

gaaacacaat ttgtggattt ccatgatctt acaatagatg gtacgacacc caacattgtg   3180

acctttgcat cttgaacaaa tttagcgaaa ccagagacta aaggactacc gttgtacaag   3240

gcaatagatg caccatttaa caaactagca taaaccaacc aaggacccat catccaaccc   3300

aaattagttg gccatactat aacgtcacct tttctaatat ccaaatgaga ccaaccatca   3360
```

-continued

```
gcagcagcct tcaatggggt ggcttgtgtc caaggaattg cttttggttc acctgtagta   3420
ccactggaga ataagatgtt agtataagca tcaacaggtt gttctctggc agtaaactcg   3480
cagtttttaa actccttggc tctttctaaa aagtaatccc aagatatgtc accatctctc   3540
aattctgcac caatgttaga accactacaa gggataacta ttgccattgg ggatttagct   3600
tcaactactc ttgaatacaa tggtattctc tttttacctc tgatgatgtg atcttgtgtg   3660
aaaattgcct tagctttgga taatctcaat ctagttgaga tttcaggggc ggaaaatgaa   3720
tctgctatag agacaactac gtaaccagcc aatactatgg ccaaatatat aacaacagca   3780
tcaacatgca ttggcatatc gatggctatt gcacaacctt tttctaaacc catttcttcc   3840
aatgcataac caaccaacca aactctcttt ctcaattgat ctaatgtcaa cttattcaaa   3900
ggcaagtcat cgttaccctc gtctctccaa acgatcatag tatcgttcaa tttcttattg   3960
gagtttacgt tcaagcaatt tttagctgag ttcaagtaac caccaggtaa ccattcagaa   4020
ccacctgggt tgttgatgtc atctcttctc aagatacatt ctgggtcctt agagaaacta   4080
attttcattt catccatcaa tactgttctc caatagactt cagggtttct aacagaaaat   4140
tcttggaagt gagaaaaaga agaaattgga tctttgtact ttacacccaa aaattcttta   4200
cctctctttt ccaacaaagc acccaaatta gttgacttga ctttttcagg gtctggaatc   4260
caagcaggtg gggctggacc gaaatccttg tagcaaccat aaaacaacat ttggtgtaag   4320
gagaaaggca aatctggtga caagatatgg ttagcgatgt tgatccaagt ttgaggggtt   4380
gcagcaccat aattacaaac gatttctgcc aatctaccat gtaatgtttc tgctacttct   4440
gaggtgatac ccaatgcgat gaaatctgag gcaacgactg aatccaagga cttatagttt   4500
ttacccatac tagttctaga tccgtcgaaa ctaagttctt ggtgttttaa aactaaaaaa   4560
aagactaact ataaaagtag aatttaagaa gtttaagaaa tagatttaca gaattacaat   4620
caatacctac cgtctttata tacttattag tcaagtaggg gaataatttc agggaactgg   4680
tttaaacctt ttttttcagc tttttccaaa tcagagagag cagaaggtaa tagaaggtgt   4740
aagaaaatga gatagataca tgcgtgggtc aattgccttg tgtcatcatt tactccaggc   4800
aggttgcatc actccattga ggttgtgccc gtttttttgcc tgtttgtgcc ctgttctctg   4860
tagttgcgct aagagaatgg acctatgaac tgatggttgg tgaagaaaac aatattttgg   4920
tgctgggatt cttttttttt ctggatgcca gcttaaaaag cgggctccat tatatttagt   4980
ggatgccagg aataaacctg ttcacccaag caccatcagt gttatatatt ctgtgtaacc   5040
cgccccctat tttggcatgt acgggttaca gcagaattaa aaggctaatt ttttgactaa   5100
ataaagttag gaaaatcact actattaatt atttacgtat tctttgaaat ggcagtattg   5160
ataatgataa actcgagagc tccagctttt gttcccttta gtgagggtta attgcgcgct   5220
tggcgtaatc atggtcatag ctgtttcctg tgtgaaattg ttatccgctc acaattccac   5280
acaacatagg agccggaagc ataaagtgta aagcctgggg tgcctaatga gtgaggtaac   5340
tcacattaat tgcgttgcgc tcactgcccg ctttccagtc gggaaacctg tcgtgccagc   5400
tgcattaatg aatcggccaa cgcgcgggga gaggcggttt gcgtattggg cgctcttccg   5460
cttcctcgct cactgactcg ctgcgctcgg tcgttcggct gcggcgagcg gtatcagctc   5520
actcaaaggc ggtaatacgg ttatccacag aatcagggga taacgcagga aagaacatgt   5580
gagcaaaagg ccagcaaaag gccaggaacc gtaaaaaggc cgcgttgctg gcgtttttcc   5640
ataggctccg cccccctgac gagcatcaca aaaatcgacg ctcaagtcag aggtggcgaa   5700
```

-continued

```
acccgacagg actataaaga taccaggcgt ttccccctgg aagctccctc gtgcgctctc   5760
ctgttccgac cctgccgctt accggatacc tgtccgcctt tctcccttcg ggaagcgtgg   5820
cgctttctca tagctcacgc tgtaggtatc tcagttcggt gtaggtcgtt cgctccaagc   5880
tgggctgtgt gcacgaaccc cccgttcagc ccgaccgctg cgccttatcc ggtaactatc   5940
gtcttgagtc caacccggta agacacgact tatcgccact ggcagcagcc actggtaaca   6000
ggattagcag agcgaggtat gtaggcggtg ctacagagtt cttgaagtgg tggcctaact   6060
acggctacac tagaaggaca gtatttggta tctgcgctct gctgaagcca gttaccttcg   6120
gaaaaagagt tggtagctct tgatccggca aacaaaccac cgctggtagc ggtggttttt   6180
ttgtttgcaa gcagcagatt acgcgcagaa aaaaaggatc tcaagaagat cctttgatct   6240
tttctacggg gtctgacgct cagtggaacg aaaactcacg ttaagggatt ttggtcatga   6300
gattatcaaa aaggatcttc acctagatcc ttttaaatta aaaatgaagt tttaaatcaa   6360
tctaaagtat atatgagtaa acttggtctg acagttacca atgcttaatc agtgaggcac   6420
ctatctcagc gatctgtcta tttcgttcat ccatagttgc ctgactcccc gtcgtgtaga   6480
taactacgat acgggagggc ttaccatctg gccccagtgc tgcaatgata ccgcgagacc   6540
cacgctcacc ggctccagat ttatcagcaa taaaccagcc agccggaagg gccgagcgca   6600
gaagtggtcc tgcaacttta tccgcctcca tccagtctat taattgttgc cgggaagcta   6660
gagtaagtag ttcgccagtt aatagtttgc gcaacgttgt tgccattgct acaggcatcg   6720
tggtgtcacg ctcgtcgttt ggtatggctt cattcagctc cggttcccaa cgatcaaggc   6780
gagttacatg atcccccatg ttgtgcaaaa aagcggttag ctccttcggt cctccgatcg   6840
ttgtcagaag taagttggcc gcagtgttat cactcatggt tatggcagca ctgcataatt   6900
ctcttactgt catgccatcc gtaagatgct tttctgtgac tggtgagtac tcaaccaagt   6960
cattctgaga atagtgtatg cggcgaccga gttgctcttg cccggcgtca atacgggata   7020
ataccgcgcc acatagcaga actttaaaag tgctcatcat tggaaaacgt tcttcggggc   7080
gaaaactctc aaggatctta ccgctgttga gatccagttc gatgtaaccc actcgtgcac   7140
ccaactgatc ttcagcatct tttactttca ccagcgtttc tgggtgagca aaaacaggaa   7200
ggcaaaatgc cgcaaaaaag ggaataaggg cgacacggaa atgttgaata ctcatactct   7260
tcctttttca atattattga agcatttatc agggttattg tctcatgagc ggatacatat   7320
ttgaatgtat ttagaaaaat aaacaaatag gggttccgcg cacatttccc cgaaaagtgc   7380
cacctgggtc cttttcatca cgtgctataa aaataattat aatttaaatt ttttaatata   7440
aatatataaa ttaaaaatag aaagtaaaaa aagaaattaa agaaaaaata gtttttgttt   7500
tccgaagatg taaaagactc tagggggatc gccaacaaat actacctttt atcttgctct   7560
tcctgctctc aggtattaat gccgaattgt ttcatcttgt ctgtgtagaa gaccacacac   7620
gaaaatcctg tgattttaca ttttacttat cgttaatcga atgtatatct atttaatctg   7680
cttttcttgt ctaataaata tatatgtaaa gtacgctttt tgttgaaatt ttttaaacct   7740
ttgtttattt ttttttcttc attccgtaac tcttctacct tctttattta ctttctaaaa   7800
tccaaataca aaacataaaa ataaataaac acagagtaaa ttcccaaatt attccatcat   7860
taaaagatac gaggcgcgtg taagttacag gcaagcgatc cgtcctaaga aaccattatt   7920
atcatgacat taacctataa aaataggcgt atcacgaggc cctttcgtc              7969
```

<210> SEQ ID NO 2
<211> LENGTH: 10004

<212> TYPE: DNA
<213> ORGANISM: Artificial Sequence
<220> FEATURE:
<223> OTHER INFORMATION: Codon optimized

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctttca attcatcatt ttttttttat tctttttttt gatttcggtt    360
tctttgaaat ttttttgatt cggtaatctc cgaacagaag gaagaacgaa ggaaggagca    420
cagacttaga ttggtatata tacgcatatg tagtgttgaa gaaacatgaa attgcccagt    480
attcttaacc caactgcaca gaacaaaaac ctgcaggaaa cgaagataaa tcatgtcgaa    540
agctacatat aaggaacgtg ctgctactca tcctagtcct gttgctgcca agctatttaa    600
tatcatgcac gaaaagcaaa caaacttgtg tgcttcattg gatgttcgta ccaccaagga    660
attactggag ttagttgaag cattaggtcc caaaatttgt ttactaaaaa cacatgtgga    720
tatcttgact gatttttcca tggagggcac agttaagccg ctaaaggcat tatccgccaa    780
gtacaatttt ttactcttcg aagacagaaa atttgctgac attggtaata cagtcaaatt    840
gcagtactct gcgggtgtat acagaatagc agaatgggca gacattacga atgcacacgg    900
tgtggtgggc ccaggtattg ttagcggttt gaagcaggcg gcagaagaag taacaaagga    960
acctagaggc cttttgatgt tagcagaatt gtcatgcaag ggctccctat ctactggaga   1020
atatactaag ggtactgttg acattgcgaa gagcgacaaa gattttgtta tcggctttat   1080
tgctcaaaga gacatgggtg gaagagatga aggttacgat tggttgatta tgacacccgg   1140
tgtgggttta gatgacaagg gagacgcatt gggtcaacag tatagaaccg tggatgatgt   1200
ggtctctaca ggatctgaca ttattattgt tggaagagga ctatttgcaa agggaaggga   1260
tgctaaggta gagggtgaac gttacagaaa agcaggctgg gaagcatatt tgagaagatg   1320
cggccagcaa aactaatgac accgattatt taaagctgca gcatacgata tatatacatg   1380
tgtatatatg tatacctatg aatgtcagta agtatgtata cgaacagtat gatactgaag   1440
atgacaaggt aatgcatcat tctatacgtg tcattctgaa cgaggcgcgc tttccttttt   1500
tctttttgct ttttcttttt ttttctcttg aactcgacgg atctatgcgg tgtgaaatac   1560
cgcacagatg cgtaaggaga aaataccgca tcaggaaatt gtaaacgtta atattttgtt   1620
aaaattcgcg ttaaattttt gttaaatcag ctcatttttt aaccaatagg ccgaaatcgg   1680
caaaatccct tataaatcaa aagaatagac cgagataggg ttgagtgttg ttccagtttg   1740
gaacaagagt ccactattaa agaacgtgga ctccaacgtc aaagggcgaa aaaccgtcta   1800
tcagggcgat ggcccactac gtgaaccatc accctaatca agttttttgg ggtcgaggtg   1860
ccgtaaagca ctaaatcgga accctaaagg gagcccccga tttagagctt gacggggaaa   1920
gccggcgaac gtggcgagaa aggaagggaa gaaagcgaaa ggagcgggcg ctagggcgct   1980
ggcaagtgta gcggtcacgc tgcgcgtaac caccacaccc gccgcgctta atgcgccgct   2040
acagggcgcg tcgcgccatt cgccattcag gctgcgcaac tgttgggaag ggcgatcggt   2100
gcgggcctct tcgctattac gccagctggc gaaaggggga tgtgctgcaa ggcgattaag   2160
```

```
ttgggtaacg ccagggtttt cccagtcacg acgttgtaaa acgacggcca gtgagcgcgc   2220

gtaatacgac tcactatagg gcgaattggg taccggccgc aaattaaagc cttcgagcgt   2280

cccaaaacct tctcaagcaa ggttttcagt ataatgttac atgcgtacac gcgtctgtac   2340

agaaaaaaaa gaaaaatttg aaatataaat aacgttctta atactaacat aactataaaa   2400

aaataaatag ggacctagac ttcaggttgt ctaactcctt ccttttcggt tagagcggat   2460

gtggggggag ggcgtgaatg taagcgtgac ataactaatt acatgactcg aggtcgactt   2520

acttgtcatc gtcatctttg tagtcaatat cgtggtcttt atagtcaccg tcatgatcct   2580

tgtaatcctt tgatctcttg tagaccttat tcaagaaagc tgtcaaaacg tcggctttaa   2640

aacctcttga ttcatcaact tgactaatct ttgcctttaa gtctttagcg atggattctt   2700

cgtattcatg gtacaattgt tcaatcttca aatcattaaa aattttctta cactttgctt   2760

cagcaactga gtccttttta ccgtagtttt catccaaagt ctttctttgt tcggcagatg   2820

ctaattccaa agccttgtta ataacccaac tgcacttatt gtcttgaata tctgtaccga   2880

ttttacctat ttgttctgga gtaccgaaac agtctaagta gtcatcttgg atttggaagt   2940

attcacccaa aggtatcaaa acatctcttg cttgcttcaa gtctttttca tcagtaatac   3000

cagctacgta catagccaag gcgactggca aatagaagga gtaataagca gtttcaaagg   3060

tgacgatgaa tgaatgtttc ttcaaggaaa actttgacaa gtcaacttta tcttcaggtg   3120

cagttatcaa atccatcaat tgacccaatt ctgtttggaa agtaacttcg tggaataatt   3180

cggtaatatc gatgtagtac ttttcgtttc tgaaatgtga cttcaacaat ttatagatag   3240

cggcttccaa cataaaagca tcatttatgg ctatttcacc aacttctgga actttgtacc   3300

agcatggttg acctcttctt gttatagact tatccatcat gtcatcggca accaaaaagt   3360

atgcttgcaa caattcaata caccaaccca agatagcgac cttttcgtat tcttcttgac   3420

ctaattgttc aacggttttg ttagacaaga tagcataagt atcaactaca ctcaaacctc   3480

tattcaattt accacctgga gtattgtagt ttaaagagtg agcataccaa tcgcaggctt   3540

ctttaggcat accataagct aacaaactag cgttcaattc ttcaactaac tttgggaata   3600

cgttcaagaa tctttctctt cttatttcct tttctgaagc cataggacct ggattttctt   3660

caacgtcacc acatgttaac aaagaacctc taccttcttc gaaatgactg aattgttgtc   3720

tcaaaactct tctcatgatc ttgtttgttg cagttctagg taaggatgac aatgggacaa   3780

ctctagtaac tttgaataat gggttcaatt tcttttgcaa acccaagtta aaggataatc   3840

tcaattggtt caaatcaatg gttgtgtcgt ttgaatcctt caatacgaaa aatatgacca   3900

attgttctgg accaccaccc aaaggtggaa caccaatagc agtggtttca aaaactctgt   3960

catctacttc attacagact ctttcgattt cgatagaact aattttgata ccaccgatgt   4020

tcatagtgtc atcggctcta ccgtgtgcat ggtagtaacc gttagaggtc aattcgaaaa   4080

tgtcaccatg tcttctcaat acttcaccat tcaaggttgg catacccttg aaatagacat   4140

cgtgatgatt accgtttaac aatgtttttg aggcaccaaa cataacagga cctaatgcca   4200

attcaccgat acctggctta tttttaggca ttgggtaacc gttcttatct aatatgtaca   4260

aggtgcaacc catacattgg gatgaaaaag aacttaaaga ttgagcttgc aaaaatgaac   4320

cagcagaaaa agcaccaccg atttctgtac caccacacat ttctataact ggcttgtagt   4380

tagctctacc cattaaccac aaatattcgt ctacattaga ggcttcaccg gatgaagaaa   4440

agcatcttat ggtggaccaa tcgtaacctg aaacacaatt tgtggatttc catgatctta   4500

caatagatgg tacgacaccc aacattgtga cctttgcatc ttgaacaaat ttagcgaaac   4560
```

```
cagagactaa aggactaccg ttgtacaagg caatagatgc accatttaac aaactagcat   4620

aaaccaacca aggacccatc atccaaccca aattagttgg ccatactata acgtcacctt   4680

ttctaatatc caaatgagac caaccatcag cagcagcctt caatggggtg gcttgtgtcc   4740

aaggaattgc ttttggttca cctgtagtac cactggagaa taagatgtta gtataagcat   4800

caacaggttg ttctctggca gtaaactcgc agtttttaaa ctccttggct ctttctaaaa   4860

agtaatccca agatatgtca ccatctctca attctgcacc aatgttagaa ccactacaag   4920

ggataactat tgccattggg gatttagctt caactactct tgaatacaat ggtattctct   4980

ttttacctct gatgatgtga tcttgtgtga aaattgcctt agctttggat aatctcaatc   5040

tagttgagat ttcaggggcg gaaaatgaat ctgctataga gacaactacg taaccagcca   5100

atactatggc caaatatata acaacagcat caacatgcat tggcatatcg atggctattg   5160

cacaaccttt ttctaaaccc atttcttcca atgcataacc aaccaaccaa actctctttc   5220

tcaattgatc taatgtcaac ttattcaaag gcaagtcatc gttaccctcg tctctccaaa   5280

cgatcatagt atcgttcaat ttcttattgg agtttacgtt caagcaattt ttagctgagt   5340

tcaagtaacc accaggtaac cattcagaac cacctgggtt gttgatgtca tctcttctca   5400

agatacattc tgggtcctta gagaaactaa ttttcatttc atccatcaat actgttctcc   5460

aatagacttc agggtttcta acagaaaatt cttggaagtg agaaaaagaa gaaattggat   5520

ctttgtactt tacacccaaa aattctttac ctctcttttc caacaaagca cccaaattag   5580

ttgacttgac tttttcaggg tctggaatcc aagcaggtgg ggctggaccg aaatccttgt   5640

agcaaccata aaacaacatt tggtgtaagg agaaaggcaa atctggtgac aagatatggt   5700

tagcgatgtt gatccaagtt tgaggggttg cagcaccata attacaaacg atttctgcca   5760

atctaccatg taatgtttct gctacttctg aggtgatacc caatgcgatg aaatctgagg   5820

caacgactga atccaaggac ttatagtttt tacccatact agttctagat ccgtcgaaac   5880

taagttcttg gtgttttaaa actaaaaaaa agactaacta taaaagtaga atttaagaag   5940

tttaagaaat agatttacag aattacaatc aatacctacc gtctttatat acttattagt   6000

caagtagggg aataatttca gggaactggt ttaaaccttt tttttcagct ttttccaaat   6060

cagagagagc agaaggtaat agaaggtgta agaaaaatgag atagatacat gcgtgggtca   6120

attgccttgt gtcatcattt actccaggca ggttgcatca ctccattgag gttgtgcccg   6180

ttttttgcct gtttgtgccc tgttctctgt agttgcgcta agagaatgga cctatgaact   6240

gatggttggt gaagaaaaca atattttggt gctgggattc tttttttttc tggatgccag   6300

cttaaaaagc gggctccatt atatttagtg gatgccagga ataaacctgt tcacccaagc   6360

accatcagtg ttatatattc tgtgtaaccc gccccctatt ttggcatgta cgggttacag   6420

cagaattaaa aggctaattt tttgactaaa taaagttagg aaaatcacta ctattaatta   6480

tttacgtatt ctttgaaatg gcagtattga taatgataaa ctcgagagct ccagcttttg   6540

ttcagttgat tgtatgcttg gtatagcttg aaatattgtg cagaaaaaga aacaaggaag   6600

aaagggaacg agaacaatga cgaggaaaca aaagattaat aattgcaggt ctatttatac   6660

ttgatagcaa gacagcaaac tttttttat ttcaaattca agtaactgga aggaaggccg   6720

tataccgttg ctcattagag agtagtgtgc gtgaatgaag gaaggaaaaa gtttcgtgtg   6780

cttcgagata cccctcatca gctctggaac aacgacatct gttggtgctg tctttgtcgt   6840

taattttttc ctttagtgtc ttccatcatt tttttgtcat tgcggatatg gtgagacaac   6900
```

-continued

```
aacgggggag agagaaaaga aaaaaaaaga aaagaagttg catgcgccta ttattacttc   6960
aatagatggc aaatggaaaa agggtagtga aacttcgata tgatgatggc tatcaagtct   7020
agggctacag tattagttcg ttatgtacca ccatcaatga ggcagtgtaa ttggtgtagt   7080
cttgtttagc ccattatgtc ttgtctggta tctgttctat tgtatatctc cctccgcca    7140
cctacatgtt agggagacca acgaaggtat tataggaatc ccgatgtatg ggtttggttg   7200
ccagaaaaga ggaagtccat attgtacacc cggaaacaac aaaaggatgc gcgcttggcg   7260
taatcatggt catagctgtt tcctgtgtga aattgttatc cgctcacaat tccacacaac   7320
ataggagccg gaagcataaa gtgtaaagcc tggggtgcct aatgagtgag gtaactcaca   7380
ttaattgcgt tgcgctcact gcccgctttc cagtcgggaa acctgtcgtg ccagctgcat   7440
taatgaatcg gccaacgcgc ggggagaggc ggtttgcgta ttgggcgctc ttccgcttcc   7500
tcgctcactg actcgctgcg ctcggtcgtt cggctgcggc gagcggtatc agctcactca   7560
aaggcggtaa tacggttatc cacagaatca ggggataacg caggaaagaa catgtgagca   7620
aaaggccagc aaaaggccag gaaccgtaaa aaggccgcgt tgctggcgtt tttccatagg   7680
ctccgccccc ctgacgagca tcacaaaaat cgacgctcaa gtcagaggtg gcgaaacccg   7740
acaggactat aaagatacca ggcgtttccc cctggaagct ccctcgtgcg ctctcctgtt   7800
ccgaccctgc cgcttaccgg atacctgtcc gcctttctcc cttcgggaag cgtggcgctt   7860
tctcatagct cacgctgtag gtatctcagt tcggtgtagg tcgttcgctc caagctgggc   7920
tgtgtgcacg aaccccccgt tcagcccgac cgctgcgcct tatccggtaa ctatcgtctt   7980
gagtccaacc cggtaagaca cgacttatcg ccactggcag cagccactgg taacaggatt   8040
agcagagcga ggtatgtagg cggtgctaca gagttcttga agtggtggcc taactacggc   8100
tacactagaa ggacagtatt tggtatctgc gctctgctga agccagttac cttcggaaaa   8160
agagttggta gctcttgatc cggcaaacaa accaccgctg gtagcggtgg tttttttgtt   8220
tgcaagcagc agattacgcg cagaaaaaaa ggatctcaag aagatccttt gatcttttct   8280
acggggtctg acgctcagtg gaacgaaaac tcacgttaag ggattttggt catgagatta   8340
tcaaaaagga tcttcaccta gatcctttta aattaaaaat gaagttttaa atcaatctaa   8400
agtatatatg agtaaacttg gtctgacagt taccaatgct taatcagtga ggcacctatc   8460
tcagcgatct gtctatttcg ttcatccata gttgcctgac tccccgtcgt gtagataact   8520
acgatacggg agggcttacc atctggcccc agtgctgcaa tgataccgcg agacccacgc   8580
tcaccggctc cagatttatc agcaataaac cagccagccg gaagggccga gcgcagaagt   8640
ggtcctgcaa ctttatccgc ctccatccag tctattaatt gttgccggga agctagagta   8700
agtagttcgc cagttaatag tttgcgcaac gttgttgcca ttgctacagg catcgtggtg   8760
tcacgctcgt cgtttggtat ggcttcattc agctccggtt cccaacgatc aaggcgagtt   8820
acatgatccc ccatgttgtg caaaaaagcg gttagctcct tcggtcctcc gatcgttgtc   8880
agaagtaagt tggccgcagt gttatcactc atggttatgg cagcactgca taattctctt   8940
actgtcatgc catccgtaag atgcttttct gtgactggtg agtactcaac caagtcattc   9000
tgagaatagt gtatgcggcg accgagttgc tcttgcccgg cgtcaatacg ggataatacc   9060
gcgccacata gcagaacttt aaaagtgctc atcattggaa aacgttcttc ggggcgaaaa   9120
ctctcaagga tcttaccgct gttgagatcc agttcgatgt aacccactcg tgcacccaac   9180
tgatcttcag catcttttac tttcaccagc gtttctgggt gagcaaaaac aggaaggcaa   9240
aatgccgcaa aaaagggaat aagggcgaca cggaaatgtt gaatactcat actcttcctt   9300
```

```
tttcaatatt attgaagcat ttatcagggt tattgtctca tgagcggata catatttgaa   9360

tgtatttaga aaaataaaca aataggggtt ccgcgcacat ttccccgaaa agtgccacct   9420

gggtcctttt catcacgtgc tataaaaata attataattt aaattttttta atataaatat   9480

ataaattaaa aatagaaagt aaaaaaagaa attaaagaaa aaatagtttt tgttttccga   9540

agatgtaaaa gactctaggg ggatcgccaa caaatactac cttttatctt gctcttcctg   9600

ctctcaggta ttaatgccga attgtttcat cttgtctgtg tagaagacca cacacgaaaa   9660

tcctgtgatt ttacatttta cttatcgtta atcgaatgta tatctattta atctgctttt   9720

cttgtctaat aaatatatat gtaaagtacg ctttttgttg aaattttttta aacctttgtt   9780

tatttttttt tcttcattcc gtaactcttc taccttcttt atttactttc taaaatccaa   9840

atacaaaaca taaaaataaa taaacacaga gtaaattccc aaattattcc atcattaaaa   9900

gatacgaggc gcgtgtaagt tacaggcaag cgatccgtcc taagaaacca ttattatcat   9960

gacattaacc tataaaaata ggcgtatcac gaggcccttt cgtc                    10004
```

```
<210> SEQ ID NO 3
<211> LENGTH: 9508
<212> TYPE: DNA
<213> ORGANISM: Artificial Sequence
<220> FEATURE:
<223> OTHER INFORMATION: Codon optimized

<400> SEQUENCE: 3

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tcttttttcta    300

ttactcttgg cctcctaacg acattactat atatataata taggaagcat ttaatagaca    360

gcatcgtaat atatgtgtac tttgcagtta tgacgccaga tggcagtagt ggaagatatt    420

ctttattgaa aaatagcttg tcaccttacg tacaatcttg atccggagct tttctttttt    480

tgccgattaa gaattaattc ggtcgaaaaa agaaaaggag agggccaaga gggagggcat    540

tggtgactat tgagcacgtg agtatacgtg attaagcaca caaaggcagc ttggagtatg    600

tctgttatta atttcacagg tagttctggt ccattggtga aagtttgcgg cttgcagagc    660

acagaggccg cagaatgtgc tctagattcc gatgctgact tgctgggtat tatatgtgtg    720

cccaatagaa agagaacaat tgacccggtt attgcaagga aaatttcaag tcttgtaaaa    780

gcatataaaa atagttcagg cactccgaaa tacttggttg gcgtgtttcg taatcaacct    840

aaggaggatg ttttggctct ggtcaatgat tacggcattg atatcgtcca actgcatgga    900

gatgagtcgt ggcaagaata ccaagagttc ctcggtttgc cagttattaa aagactcgta    960

tttccaaaag actgcaacat actactcagt gcagcttcac agaaacctca ttcgtttatt   1020

cccttgtttg attcagaagc aggtgggaca ggtgaacttt tggattggaa ctcgatttct   1080

gactgggttg gaaggcaaga gagccccgaa agcttacatt ttatgttagc tggtggactg   1140

acgccagaaa atgttggtga tgcgcttaga ttaaatggcg ttattggtgt tgatgtaagc   1200

ggaggtgtgg agacaaatgg tgtaaaagac tctaacaaaa tagcaaattt cgtcaaaaat   1260

gctaagaaat agtgacaccg attatttaaa gctgcagcat acgatatata tacatgtgta   1320
```

```
tatatgtata cctatgaatg tcagtaagta tgtatacgaa cagtatgata ctgaagatga   1380
caaggtaatg catcattcta tacgtgtcat tctgaacgag gcgcgctttc ctttttttctt   1440
tttgcttttt cttttttttt ctcttgaact cgacggatct atgcggtgtg aaataccgca   1500
cagatgcgta aggagaaaat accgcatcag gaaattgtaa acgttaatat tttgttaaaa   1560
ttcgcgttaa atttttgtta aatcagctca ttttttaacc aataggccga aatcggcaaa   1620
atcccttata aatcaaaaga atagaccgag atagggttga gtgttgttcc agtttggaac   1680
aagagtccac tattaaagaa cgtggactcc aacgtcaaag ggcgaaaaac cgtctatcag   1740
ggcgatggcc cactacgtga accatcaccc taatcaagtt ttttggggtc gaggtgccgt   1800
aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa gggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280
aaaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg gtggtgaggt ggcaaaggtg ggatggattg   2520
ttcgtttctg aaaaagttgt tagggtcggc tttagtcttt actttaacta atctgttgaa   2580
atttttacca aagtactttt caccccaaat tcttgcttgt gtatagttat ttggagattc   2640
agggttagtt ttacctaagt ccaaatctct gtagttcaaa tatgccaatc ttgggttttg   2700
actaacgtaa ggtgtagtga agttgtaaac ggatctgacc cagttgatat gcttttcgtt   2760
atcttcttgc ttttcccatg aggctgtgta ccataattca tacatgatac cagctctgtg   2820
aggaaatggt atggctgatt cagatatttc ttccataata ccaccgtatg gatacaaaac   2880
gtacatgccg acacctacat cttcttcgta caacttttcc aatatcttga ccattgcagt   2940
ttcagggatt ggtttcttaa cgtagtccaa tttaatagaa aaagcggtct ttttaccagc   3000
ggatctatcc aacaagattt ccttttttgaa gttagcggtg ttgaagttta caacacctga   3060
atagaagatg gttgtgtcta tccaagaaaa ttccttgcaa tctgtctttt taatacccaa   3120
ttctgggaat gacttattca tcaaatcaac caaagaatct acaccaccat ggaaaattga   3180
agaaaaataa ccgtgaacag tggtcttatt tttaccatgg ttatctgtaa tatttttagt   3240
gatgaaatgg gtcatcaaaa ccaagtcctt atcgtacttg taagcgatgt tttgccactt   3300
attaaacaac ttaaccaaac cgtggatttc catgttcttt ttgacagaga aaatagtact   3360
tttggaagga acagcgacta acttaatttt ccaagcggca atgataccga aattttcacc   3420
accaccacct cttatggccc aaaacaaatc ttcacccata gactttctgt ccaaaacttt   3480
accatctacg ttaaccaaat gggcgtctat aatattatct gcagctaaac cgtagtttct   3540
catcaatgca ccataaccac caccagaaaa gtgaccaccg acacctactg ttggacagta   3600
accaccaggg aaagaaaagt tttcattctt ttcgttgatc cagtagtaaa cttcacccaa   3660
ggtggcacct gcttctaccc atgctgtttg actgtgaacg tcgatcttta tggaatgcat   3720
```

```
atttctcaaa tcgactacaa cgaatggaac ttgtgagatg taagacatgc cttctgcatc   3780
atgaccacct gatctagttc tgatttgcaa acctactttc ttagagcaca atatagaagc   3840
ttgaatgtga ctaacattgg aaggtgtaac aatgactaaa ggttttggtg tagtgtcaga   3900
agtgaatctc aaattttgga tggtactgtt caaaacggac atgtacaatt gatcatgttg   3960
agtatatata aactttgggt tagcagggtt gtttgggatg tattcggaga aacacttcaa   4020
aaagttttct tgtggatttg cgatggagat ttggatgttg aaggacaaga agaagaagat   4080
tattttacag acgaaccaga aagagaatgc ggagcagttc ataggacctg gattttcttc   4140
aacgtcacca caggtcaaca aagaacctct accttcaata aaaacgtata ccaaatattc   4200
agcgtagtac aatttccaca taaactcgta gaatcttcta cctgcttcag ggtcataatt   4260
tgtcaaagcg aaatctctag tttgcaagat caaccagaaa gccaagatgg catgtgacaa   4320
caacataacg ttagaattaa aggcttgtgg ccaaatgata cctgccaaaa tggctgcgac   4380
gtaacttaac aaaacgatac cggagcagaa caaagtcaaa tttcttgaac cgtacttaga   4440
agccaaggta ctaataccga actttgtgtc accttcaacg tcagaggcat ccttgatcaa   4500
ggctaatgca gaacccatac ttttcatgaa tgccaacaaa aatgtgaatg aaggtctcaa   4560
ttcgaatggc aaacctaaag cagctcttga agcgtagtag aaggtgaagt ttgtgatgat   4620
atgagctaag aaattcaaca aaaaggcagt actagggttt tgtttccatc taaaaggtgg   4680
tacggaatag acaataccac cgaagatacc gaaacagtaa ccgaagatgt acaatggacc   4740
acccttcatt ttaattgtga tgatcaaacc gaacaaggct actatgatag acatgatcca   4800
tgcagtattg acggatattt cacctgaagc caaaggcaaa tctggtttgt taattctgtc   4860
gatgtgcaaa tcgtatattt gattaattgt agtggtgaat gaagcgatgc acaagatggc   4920
aactaaaaag aaaaatgcct tgaacatcaa ggaccatgaa attaagttag tgttatgcaa   4980
caattcttta ccgaataaac cgcatgcaca agaagtaaaa gcgattatgg tgtatggtct   5040
ttgcaacttc caacatgctt taccgaagtt caaaattttt gtggcaacag agtgattatc   5100
actttcaggt ggttcagttt gatttgtagt tgcagctctg atagagttct tagctataga   5160
caaactttcg gagcacttat tttgtaagtg gaaggacttg gttgaacaat gttttgatgg   5220
aaagttgttg taagagtact taataggtgt ctttggatgt ctgtaacaca acaatgatgt   5280
ttttggattg ttgttgtgag gattcaataa ggtatgatag ttagtttgga aggagaaagt   5340
acagacggat gataaaccca tactagttct agatccgtcg aaactaagtt cttggtgttt   5400
taaaactaaa aaaaagacta actataaaag tagaatttaa gaagtttaag aaatagattt   5460
acagaattac aatcaatacc taccgtcttt atatacttat tagtcaagta ggggaataat   5520
ttcagggaac tggtttaaac cttttttttc agctttttcc aaatcagaga gagcagaagg   5580
taatagaagg tgtaagaaaa tgagatagat acatgcgtgg gtcaattgcc ttgtgtcatc   5640
atttactcca ggcaggttgc atcactccat tgaggttgtg cccgtttttt gcctgtttgt   5700
gccctgttct ctgtagttgc gctaagagaa tggacctatg aactgatggt tggtgaagaa   5760
aacaatattt tggtgctggg attctttttt tttctggatg ccagcttaaa aagcgggctc   5820
cattatattt agtggatgcc aggaataaac ctgttcaccc aagcaccatc agtgttatat   5880
attctgtgta acccgccccc tattttggca tgtacgggtt acagcagaat taaaaggcta   5940
attttttgac taaataaagt taggaaaatc actactatta attatttacg tattctttga   6000
aatggcagta ttgataatga taaactcgag agctccagct tttgttcagt tgattgtatg   6060
```

```
cttggtatag cttgaaatat tgtgcagaaa aagaaacaag gaagaaaggg aacgagaaca   6120
atgacgagga aacaaaagat taataattgc aggtctattt atacttgata gcaagacagc   6180
aaactttttt ttatttcaaa ttcaagtaac tggaaggaag gccgtatacc gttgctcatt   6240
agagagtagt gtgcgtgaat gaaggaagga aaaagtttcg tgtgcttcga gataccccctc  6300
atcagctctg gaacaacgac atctgttggt gctgtctttg tcgttaattt tttcctttag   6360
tgtcttccat catttttttg tcattgcgga tatggtgaga caacaacggg ggagagagaa   6420
aagaaaaaaa aagaaaagaa gttgcatgcg cctattatta cttcaataga tggcaaatgg   6480
aaaaagggta gtgaaacttc gatatgatga tggctatcaa gtctagggct acagtattag   6540
ttcgttatgt accaccatca atgaggcagt gtaattggtg tagtcttgtt tagcccatta   6600
tgtcttgtct ggtatctgtt ctattgtata tctcccctcc gccacctaca tgttagggag   6660
accaacgaag gtattatagg aatcccgatg tatgggtttg gttgccagaa aagaggaagt   6720
ccatattgta cacccggaaa caacaaaagg atgcgcgctt ggcgtaatca tggtcatagc   6780
tgtttcctgt gtgaaattgt tatccgctca caattccaca caacatagga gccggaagca   6840
taaagtgtaa agcctggggt gcctaatgag tgaggtaact cacattaatt gcgttgcgct   6900
cactgcccgc tttccagtcg ggaaacctgt cgtgccagct gcattaatga atcggccaac   6960
gcgcggggag aggcggtttg cgtattgggc gctcttccgc ttcctcgctc actgactcgc   7020
tgcgctcggt cgttcggctg cggcgagcgg tatcagctca ctcaaaggcg gtaatacggt   7080
tatccacaga atcaggggat aacgcaggaa agaacatgtg agcaaaaggc cagcaaaagg   7140
ccaggaaccg taaaaaggcc gcgttgctgg cgtttttcca taggctccgc ccccctgacg   7200
agcatcacaa aaatcgacgc tcaagtcaga ggtggcgaaa cccgacagga ctataaagat   7260
accaggcgtt tccccctgga agctccctcg tgcgctctcc tgttccgacc ctgccgctta   7320
ccggatacct gtccgccttt ctcccttcgg gaagcgtggc gctttctcat agctcacgct   7380
gtaggtatct cagttcggtg taggtcgttc gctccaagct gggctgtgtg cacgaacccc   7440
ccgttcagcc cgaccgctgc gccttatccg gtaactatcg tcttgagtcc aacccggtaa   7500
gacacgactt atcgccactg gcagcagcca ctggtaacag gattagcaga gcgaggtatg   7560
taggcggtgc tacagagttc ttgaagtggt ggcctaacta cggctacact agaaggacag   7620
tatttggtat ctgcgctctg ctgaagccag ttaccttcgg aaaaagagtt ggtagctctt   7680
gatccggcaa acaaaccacc gctggtagcg gtggtttttt tgtttgcaag cagcagatta   7740
cgcgcagaaa aaaaggatct caagaagatc ctttgatctt ttctacgggg tctgacgctc   7800
agtggaacga aaactcacgt taagggattt tggtcatgag attatcaaaa aggatcttca   7860
cctagatcct tttaaattaa aaatgaagtt ttaaatcaat ctaaagtata tatgagtaaa   7920
cttggtctga cagttaccaa tgcttaatca gtgaggcacc tatctcagcg atctgtctat   7980
ttcgttcatc catagttgcc tgactccccg tcgtgtagat aactacgata cgggagggct   8040
taccatctgg ccccagtgct gcaatgatac cgcgagaccc acgctcaccg gctccagatt   8100
tatcagcaat aaaccagcca gccggaaggg ccgagcgcag aagtggtcct gcaactttat   8160
ccgcctccat ccagtctatt aattgttgcc gggaagctag agtaagtagt tcgccagtta   8220
atagtttgcg caacgttgtt gccattgcta caggcatcgt ggtgtcacgc tcgtcgtttg   8280
gtatggcttc attcagctcc ggttcccaac gatcaaggcg agttacatga tcccccatgt   8340
tgtgcaaaaa agcggttagc tccttcggtc ctccgatcgt tgtcagaagt aagttggccg   8400
cagtgttatc actcatggtt atggcagcac tgcataattc tcttactgtc atgccatccg   8460
```

```
taagatgctt ttctgtgact ggtgagtact caaccaagtc attctgagaa tagtgtatgc   8520
ggcgaccgag ttgctcttgc ccggcgtcaa tacgggataa taccgcgcca catagcagaa   8580
ctttaaaagt gctcatcatt ggaaaacgtt cttcggggcg aaaactctca aggatcttac   8640
cgctgttgag atccagttcg atgtaaccca ctcgtgcacc caactgatct tcagcatctt   8700
ttactttcac cagcgtttct gggtgagcaa aaacaggaag gcaaaatgcc gcaaaaaagg   8760
gaataagggc gacacggaaa tgttgaatac tcatactctt cctttttcaa tattattgaa   8820
gcatttatca gggttattgt ctcatgagcg gatacatatt tgaatgtatt tagaaaaata   8880
aacaaatagg ggttccgcgc acatttcccc gaaaagtgcc acctgggtcc ttttcatcac   8940
gtgctataaa aataattata atttaaattt tttaatataa atatataaat taaaaataga   9000
aagtaaaaaa agaaattaaa gaaaaaatag tttttgtttt ccgaagatgt aaaagactct   9060
agggggatcg ccaacaaata ctacctttta tcttgctctt cctgctctca ggtattaatg   9120
ccgaattgtt tcatcttgtc tgtgtagaag accacacacg aaaatcctgt gattttacat   9180
tttacttatc gttaatcgaa tgtatatcta tttaatctgc ttttcttgtc taataaatat   9240
atatgtaaag tacgcttttt gttgaaattt tttaaacctt tgtttatttt tttttcttca   9300
ttccgtaact cttctacctt ctttatttac tttctaaaat ccaaatacaa aacataaaaa   9360
taaataaaca cagagtaaat tcccaaatta ttccatcatt aaaagatacg aggcgcgtgt   9420
aagttacagg caagcgatcc gtcctaagaa accattatta tcatgacatt aacctataaa   9480
aataggcgta tcacgaggcc ctttcgtc                                       9508
```

```
<210> SEQ ID NO 4
<211> LENGTH: 9505
<212> TYPE: DNA
<213> ORGANISM: Artificial Sequence
<220> FEATURE:
<223> OTHER INFORMATION: Codon optimized

<400> SEQUENCE: 4
```

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctaacg acattactat atatataata taggaagcat ttaatagaca    360
gcatcgtaat atatgtgtac tttgcagtta tgacgccaga tggcagtagt ggaagatatt    420
ctttattgaa aaatagcttg tcaccttacg tacaatcttg atccggagct tttctttttt    480
tgccgattaa gaattaattc ggtcgaaaaa agaaaaggag agggccaaga gggagggcat    540
tggtgactat tgagcacgtg agtatacgtg attaagcaca caaaggcagc ttggagtatg    600
tctgttatta atttcacagg tagttctggt ccattggtga aagtttgcgg cttgcagagc    660
acagaggccg cagaatgtgc tctagattcc gatgctgact tgctgggtat tatatgtgtg    720
cccaatagaa agagaacaat tgacccggtt attgcaagga aaatttcaag tcttgtaaaa    780
gcatataaaa atagttcagg cactccgaaa tacttggttg gcgtgtttcg taatcaacct    840
aaggaggatg ttttggctct ggtcaatgat tacggcattg atatcgtcca actgcatgga    900
gatgagtcgt ggcaagaata ccaagagttc ctcggtttgc cagttattaa aagactcgta    960
```

```
tttccaaaag actgcaacat actactcagt gcagcttcac agaaacctca ttcgtttatt   1020
cccttgtttg attcagaagc aggtgggaca ggtgaacttt tggattggaa ctcgatttct   1080
gactgggttg gaaggcaaga gagccccgaa agcttacatt ttatgttagc tggtggactg   1140
acgccagaaa atgttggtga tgcgcttaga ttaaatggcg ttattggtgt tgatgtaagc   1200
ggaggtgtgg agacaaatgg tgtaaaagac tctaacaaaa tagcaaattt cgtcaaaaat   1260
gctaagaaat agtgacaccg attatttaaa gctgcagcat acgatatata tacatgtgta   1320
tatatgtata cctatgaatg tcagtaagta tgtatacgaa cagtatgata ctgaagatga   1380
caaggtaatg catcattcta tacgtgtcat tctgaacgag gcgcgctttc ctttttctt    1440
tttgcttttt cttttttttt ctcttgaact cgacggatct atgcggtgtg aaataccgca   1500
cagatgcgta aggagaaaat accgcatcag gaaattgtaa acgttaatat tttgttaaaa   1560
ttcgcgttaa atttttgtta aatcagctca ttttttaacc aataggccga aatcggcaaa   1620
atcccttata aatcaaaaga atagaccgag atagggttga gtgttgttcc agtttggaac   1680
aagagtccac tattaaagaa cgtggactcc aacgtcaaag ggcgaaaaac cgtctatcag   1740
ggcgatggcc cactacgtga accatcaccc taatcaagtt ttttggggtc gaggtgccgt   1800
aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa gggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280
aaaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg tctatgtcta ggtaaaggtg gaatggattg   2520
ttcgtttcta aagaagttgt ttgggtcaac caatgtctta acctttacta atctatcgaa   2580
atttttaccg aagtattttt caccccaaat tctagcttgg gtatagttgt taggattctt   2640
tggatcgtta ataccgatgt ccaaatctct gtagttcaaa tatgccaatc tagggttttt   2700
agaaacgtat ggagtcatga agttatagat gtttctaatc cagtttaagt gcttttcgtt   2760
atcttcttgc ttttcccatg aacaaatgta ccacaattcg tataagatac cagctctatg   2820
aggaaatgga atggcagatt cactgatttc gtccattata ccaccgtatg gatacaaggc   2880
gtacatgcct gcaccaatat cttcttcgta caatttttct aagatttgga cgaaaactga   2940
ttcaggtatt ggctttttaa cgtagtctaa cttaatttta aaggcaccgt tttgacctgc   3000
ggatctatcc aataatattt ctttgttgaa gttgtctgta tcgtagttga caacacctga   3060
ataaaagatg atggtgtcga tccaagacaa ttgtctacaa tcagttttct taatacctaa   3120
ttctggaaaa gacttattca tcaagtctac taaggaatcg acaccaccca agaaaactga   3180
agaaaagtat gtgtggatag cagtcttatt tttaccttgg ttatcggtga tgtttcttgt   3240
gatgaaatga gtcatcaaca acaagtcctt atcgtacttg tatgcgatgt tttgccactt   3300
attgaccaat ttaactaatt catggatttc cattatcttt ttgactgaga acatagtaga   3360
```

```
ctttggtact gcgactaatc ttatcttcca agcaactatg ataccgaatg attctgcacc   3420
accacctctc aaagcccaaa ataagtcttc acccatagac tttctatcca aaactttacc   3480
gtgaacattt accaaatgag cgtcgattat gttatcagcg gccaaaccgt agtttctcat   3540
taaaggacca taaccaccac caccaaaatg accacctgcg caaactgttg gacagtaacc   3600
agcagccaat gataagtttt cattcttttc gttaacccag tagtatactt cacccaatgt   3660
tgcaccagct tcaacccaag cagtttgtga gtgtacgtct attttaattg atctcatgtt   3720
tctcaaatca acgataacga atggaacttg ggagatgtat gacatgcctt cactatcatg   3780
accaccggat ctagttctaa tttgcaaacc aacctttta gaacataaga tagtaccttg   3840
gatgtgagat acatgactag ggttacaat gaccaaaggt tttggagtgg tatcagaagt   3900
gaatctcaaa ttatggattg tactgttcaa gacggacatg tacaatgggt tgttttgagt   3960
gtaaaccaac ttcaaattgg tggcgttatt aggtatgtat tgtgagaagc acttcaaaaa   4020
gtttctctt gggtttgcga tacttgtttg gatgttaaag gaaaagaaaa agaagatgat   4080
cttgcatacg aaccaaaagg agaaagttga acatttcata ggacctggat tttcttcaac   4140
gtcaccacag gtcaacaaag aacctctacc ttcaataaaa acgtatacca aatattcagc   4200
gtagtacaat ttccacataa actcgtagaa tcttctacct gcttcagggt cataatttgt   4260
caaagcgaaa tctctagttt gcaagatcaa ccagaaagcc aagatggcat gtgacaacaa   4320
cataacgtta gaattaaagg cttgtggcca aatgatacct gccaaaatgg ctgcgacgta   4380
acttaacaaa acgataccgg agcagaacaa agtcaaattt cttgaaccgt acttagaagc   4440
caaggtacta ataccgaact ttgtgtcacc ttcaacgtca gaggcatcct tgatcaaggc   4500
taatgcagaa cccatacttt tcatgaatgc caacaaaaat gtgaatgaag gtctcaattc   4560
gaatggcaaa cctaaagcag ctcttgaagc gtagtagaag gtgaagtttg tgatgatatg   4620
agctaagaaa ttcaacaaaa aggcagtact agggttttgt ttccatctaa aaggtggtac   4680
ggaatagaca ataccaccga agataccgaa acagtaaccg aagatgtaca atggaccacc   4740
cttcatttta attgtgatga tcaaaccgaa caaggctact atgatagaca tgatccatgc   4800
agtattgacg gatatttcac ctgaagccaa aggcaaatct ggtttgttaa ttctgtcgat   4860
gtgcaaatcg tatatttgat taattgtagt ggtgaatgaa gcgatgcaca agatggcaac   4920
taaaaagaaa aatgccttga acatcaagga ccatgaaatt aagttagtgt tatgcaacaa   4980
ttctttaccg aataaaccgc atgcacaaga agtaaaagcg attatggtgt atggtctttg   5040
caacttccaa catgctttac cgaagttcaa aatttttgtg gcaacagagt gattatcact   5100
ttcaggtggt tcagtttgat ttgtagttgc agctctgata gagttcttag ctatagacaa   5160
actttcggag cacttatttt gtaagtggaa ggacttggtt gaacaatgtt ttgatggaaa   5220
gttgttgtaa gagtacttaa taggtgtctt tggatgtctg taacacaaca atgatgtttt   5280
tggattgttg ttgtgaggat tcaataaggt atgatagtta gtttggaagg agaaagtaca   5340
gacggatgat aaacccatac tagttctaga tccgtcgaaa ctaagttctt ggtgttttaa   5400
aactaaaaaa aagactaact ataaaagtag aatttaagaa gtttaagaaa tagatttaca   5460
gaattacaat caatacctac cgtctttata tacttattag tcaagtaggg gaataatttc   5520
agggaactgg tttaaacctt ttttttcagc tttttccaaa tcagagagag cagaaggtaa   5580
tagaaggtgt aagaaaatga gatagataca tgcgtgggtc aattgccttg tgtcatcatt   5640
tactccaggc aggttgcatc actccattga ggttgtgccc gttttttgcc tgtttgtgcc   5700
```

-continued

```
ctgttctctg tagttgcgct aagagaatgg acctatgaac tgatggttgg tgaagaaaac   5760
aatattttgg tgctgggatt cttttttttt ctggatgcca gcttaaaaag cgggctccat   5820
tatatttagt ggatgccagg aataaacctg ttcacccaag caccatcagt gttatatatt   5880
ctgtgtaacc cgcccccctat tttggcatgt acgggttaca gcagaattaa aaggctaatt   5940
ttttgactaa ataaagttag gaaaatcact actattaatt atttacgtat tctttgaaat   6000
ggcagtattg ataatgataa actcgagagc tccagctttt gttcagttga ttgtatgctt   6060
ggtatagctt gaaatattgt gcagaaaaag aaacaaggaa gaaagggaac gagaacaatg   6120
acgaggaaac aaaagattaa taattgcagg tctatttata cttgatagca agacagcaaa   6180
cttttttttta tttcaaattc aagtaactgg aaggaaggcc gtataccgtt gctcattaga   6240
gagtagtgtg cgtgaatgaa ggaaggaaaa agtttcgtgt gcttcgagat acccctcatc   6300
agctctggaa caacgacatc tgttggtgct gtctttgtcg ttaatttttt cctttagtgt   6360
cttccatcat ttttttgtca ttgcggatat ggtgagacaa caacgggggga gagagaaaag   6420
aaaaaaaaag aaaagaagtt gcatgcgcct attattactt caatagatgg caaatggaaa   6480
aagggtagtg aaacttcgat atgatgatgg ctatcaagtc tagggctaca gtattagttc   6540
gttatgtacc accatcaatg aggcagtgta attggtgtag tcttgtttag cccattatgt   6600
cttgtctggt atctgttcta ttgtatatct cccctccgcc acctacatgt tagggagacc   6660
aacgaaggta ttataggaat cccgatgtat gggtttggtt gccagaaaag aggaagtcca   6720
tattgtacac ccggaaacaa caaaaggatg cgcgcttggc gtaatcatgg tcatagctgt   6780
ttcctgtgtg aaattgttat ccgctcacaa ttccacacaa cataggagcc ggaagcataa   6840
agtgtaaagc ctggggtgcc taatgagtga ggtaactcac attaattgcg ttgcgctcac   6900
tgcccgcttt ccagtcggga aacctgtcgt gccagctgca ttaatgaatc ggccaacgcg   6960
cggggagagg cggtttgcgt attgggcgct cttccgcttc ctcgctcact gactcgctgc   7020
gctcggtcgt tcggctgcgg cgagcggtat cagctcactc aaaggcggta atacggttat   7080
ccacagaatc aggggataac gcaggaaaga acatgtgagc aaaaggccag caaaaggcca   7140
ggaaccgtaa aaaggccgcg ttgctggcgt ttttccatag gctccgcccc cctgacgagc   7200
atcacaaaaa tcgacgctca agtcagaggt ggcgaaaccc gacaggacta taaagatacc   7260
aggcgtttcc ccctggaagc tccctcgtgc gctctcctgt tccgaccctg ccgcttaccg   7320
gatacctgtc cgcctttctc ccttcgggaa gcgtggcgct ttctcatagc tcacgctgta   7380
ggtatctcag ttcggtgtag gtcgttcgct ccaagctggg ctgtgtgcac gaaccccccg   7440
ttcagcccga ccgctgcgcc ttatccggta actatcgtct tgagtccaac ccggtaagac   7500
acgacttatc gccactggca gcagccactg gtaacaggat tagcagagcg aggtatgtag   7560
gcggtgctac agagttcttg aagtggtggc ctaactacgg ctacactaga aggacagtat   7620
ttggtatctg cgctctgctg aagccagtta ccttcggaaa aagagttggt agctcttgat   7680
ccggcaaaca aaccaccgct ggtagcggtg gtttttttgt ttgcaagcag cagattacgc   7740
gcagaaaaaa aggatctcaa gaagatcctt tgatcttttc tacggggtct gacgctcagt   7800
ggaacgaaaa ctcacgttaa gggattttgg tcatgagatt atcaaaaagg atcttcacct   7860
agatcctttt aaattaaaaa tgaagtttta aatcaatcta aagtatatat gagtaaactt   7920
ggtctgacag ttaccaatgc ttaatcagtg aggcacctat ctcagcgatc tgtctatttc   7980
gttcatccat agttgcctga ctccccgtcg tgtagataac tacgatacgg gagggcttac   8040
catctggccc cagtgctgca atgataccgc gagacccacg ctcaccggct ccagatttat   8100
```

```
cagcaataaa ccagccagcc ggaagggccg agcgcagaag tggtcctgca actttatccg   8160

cctccatcca gtctattaat tgttgccggg aagctagagt aagtagttcg ccagttaata   8220

gtttgcgcaa cgttgttgcc attgctacag gcatcgtggt gtcacgctcg tcgtttggta   8280

tggcttcatt cagctccggt tcccaacgat caaggcgagt tacatgatcc cccatgttgt   8340

gcaaaaaagc ggttagctcc ttcggtcctc cgatcgttgt cagaagtaag ttggccgcag   8400

tgttatcact catggttatg gcagcactgc ataattctct tactgtcatg ccatccgtaa   8460

gatgcttttc tgtgactggt gagtactcaa ccaagtcatt ctgagaatag tgtatgcggc   8520

gaccgagttg ctcttgcccg gcgtcaatac gggataatac cgcgccacat agcagaactt   8580

taaaagtgct catcattgga aaacgttctt cggggcgaaa actctcaagg atcttaccgc   8640

tgttgagatc cagttcgatg taacccactc gtgcacccaa ctgatcttca gcatctttta   8700

ctttcaccag cgtttctggg tgagcaaaaa caggaaggca aaatgccgca aaaaagggaa   8760

taagggcgac acggaaatgt tgaatactca tactcttcct ttttcaatat tattgaagca   8820

tttatcaggg ttattgtctc atgagcggat acatatttga atgtatttag aaaaataaac   8880

aaataggggt tccgcgcaca tttccccgaa aagtgccacc tgggtccttt tcatcacgtg   8940

ctataaaaat aattataatt taaatttttt aatataaata tataaattaa aaatagaaag   9000

taaaaaaaga aattaaagaa aaaatagttt ttgttttccg aagatgtaaa agactctagg   9060

gggatcgcca acaaatacta ccttttatct tgctcttcct gctctcaggt attaatgccg   9120

aattgtttca tcttgtctgt gtagaagacc acacacgaaa atcctgtgat tttacatttt   9180

acttatcgtt aatcgaatgt atatctattt aatctgcttt tcttgtctaa taaatatata   9240

tgtaaagtac gctttttgtt gaaatttttt aaacctttgt ttattttttt ttcttcattc   9300

cgtaactctt ctaccttctt tatttacttt ctaaaatcca aatacaaaac ataaaaataa   9360

ataaacacag agtaaattcc caaattattc catcattaaa agatacgagg cgcgtgtaag   9420

ttacaggcaa gcgatccgtc ctaagaaacc attattatca tgacattaac ctataaaaat   9480

aggcgtatca cgaggccctt tcgtc                                         9505
```

<210> SEQ ID NO 5
<211> LENGTH: 8696
<212> TYPE: DNA
<213> ORGANISM: Artificial Sequence
<220> FEATURE:
<223> OTHER INFORMATION: Codon optimized

<400> SEQUENCE: 5

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accatatatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctaact gtgggaatac tcaggtatcg taagatgcaa gagttcgaat    360

ctcttagcaa ccattatttt tttcctcaac ataacgagaa cacacagggg cgctatcgca    420

cagaatcaaa ttcgatgact ggaaattttt tgttaatttc agaggtcgcc tgacgcatat    480

acctttttca actgaaaaat tgggagaaaa aggaaaggtg agaggccgga accggctttt    540

catatagaat agagaagcgt tcatgactaa atgcttgcat cacaatactt gaagttgaca    600
```

```
atattattta aggacctatt gttttttcca ataggtggtt agcaatcgtc ttactttcta    660
acttttctta ccttttacat ttcagcaata tatatatata tttcaaggat ataccattct    720
aatgtctgcc cctatgtctg cccctaagaa gatcgtcgtt ttgccaggtg accacgttgg    780
tcaagaaatc acagccgaag ccattaaggt tcttaaagct atttctgatg ttcgttccaa    840
tgtcaagttc gatttcgaaa atcatttaat tggtggtgct gctatcgatg ctacaggtgt    900
cccacttcca gatgaggcgc tggaagcctc caagaaggtt gatgccgttt tgttaggtgc    960
tgtgggtggt cctaaatggg gtaccggtag tgttagacct gaacaaggtt tactaaaaat   1020
ccgtaaagaa cttcaattgt acgccaactt aagaccatgt aactttgcat ccgactctct   1080
tttagactta tctccaatca agccacaatt tgctaaaggt actgacttcg ttgttgtcag   1140
agaattagtg ggaggtattt actttggtaa gagaaaggaa gacgatggtg atggtgtcgc   1200
ttgggatagt gaacaataca ccgttccaga agtgcaaaga atcacaagaa tggccgcttt   1260
catggcccta caacatgagc caccattgcc tatttggtcc ttggataaag ctaatgtttt   1320
ggcctcttca agattatgga gaaaaactgt ggaggaaacc atcaagaacg aattccctac   1380
attgaaggtt caacatcaat tgattgattc tgccgccatg atcctagtta agaacccaac   1440
ccacctaaat ggtattataa tcaccagcaa catgtttggt gatatcatct ccgatgaagc   1500
ctccgttatc ccaggttcct tgggtttgtt gccatctgcg tccttggcct ctttgccaga   1560
caagaacacc gcatttggtt tgtacgaacc atgccacggt tctgctccag atttgccaaa   1620
gaataaggtt gaccctatcg ccactatctt gtctgctgca atgatgttga aattgtcatt   1680
gaacttgcct gaagaaggta aggccattga agatgcagtt aaaaaggttt tggatgcagg   1740
tatcagaact ggtgatttag gtggttccaa cagtaccacc gaagtcggtg atgctgtcgc   1800
cgaagaagtt aagaaaatcc ttgcttaatg acaccgatta tttaaagctg cagcatacga   1860
tatatataca tgtgtatata tgtataccta tgaatgtcag taagtatgta tacgaacagt   1920
atgatactga agatgacaag gtaatgcatc attctatacg tgtcattctg aacgaggcgc   1980
gctttccttt tttctttttg ctttttcttt ttttttctct tgaactcgac ggatctatgc   2040
ggtgtgaaat accgcacaga tgcgtaagga gaaaataccg catcaggaaa ttgtaaacgt   2100
taatattttg ttaaaattcg cgttaaattt ttgttaaatc agctcatttt ttaaccaata   2160
ggccgaaatc ggcaaaatcc cttataaatc aaaagaatag accgagatag ggttgagtgt   2220
tgttccagtt tggaacaaga gtccactatt aaagaacgtg gactccaacg tcaaagggcg   2280
aaaaaccgtc tatcagggcg atggcccact acgtgaacca tcaccctaat caagtttttt   2340
ggggtcgagg tgccgtaaag cactaaatcg gaaccctaaa gggagccccc gatttagagc   2400
ttgacgggga aagccggcga acgtggcgag aaaggaaggg aagaaagcga aaggagcggg   2460
cgctagggcg ctggcaagtg tagcggtcac gctgcgcgta accaccacac ccgccgcgct   2520
taatgcgccg ctacagggcg cgtcgcgcca ttcgccattc aggctgcgca actgttggga   2580
agggcgatcg gtgcgggcct cttcgctatt acgccagctg gcgaaagggg gatgtgctgc   2640
aaggcgatta agttgggtaa cgccagggtt ttcccagtca cgacgttgta aaacgacggc   2700
cagtgagcgc gcgtaatacg actcactata gggcgaattg ggtaccggcc gcaaattaaa   2760
gccttcgagc gtcccaaaac cttctcaagc aaggttttca gtataatgtt acatgcgtac   2820
acgcgtctgt acagaaaaaa aagaaaaatt tgaaatataa ataacgttct taatactaac   2880
ataactataa aaaaataaat agggacctag acttcaggtt gtctaactcc ttccttttcg   2940
gttagagcgg atgtgggggg agggcgtgaa tgtaagcgtg acataactaa ttacatgact   3000
```

```
cgaggtcgac ttatgcatag tctggaacat cgtaagggta ctttcttggg gtgtaatcga   3060
agatcaacaa tttttcccag aaggatctgt aaacgtcacc aaaaccaacg tgagctggat   3120
gaatgatgta atcttggata gtttcaactg attcgaaggt tacttcgaca atgtgtgtat   3180
aaccttcttc tttcttttgt gtaacgtctt taccccagta tacatctttc atagcaggta   3240
taatgttgac caaattaacg taggtcttga aaaattcttc cttttgagct tctgtgattt   3300
catctttaaa cttcaatact atcaaatgct tgacggccat aggacctggg ttttcttcaa   3360
cgtcaccaca agttaacaag gaacctctac cttcatattt aattggtact gatctgacaa   3420
ctactctttc gacggtcaaa ccaggaccga aaccaaataa gacaccccat tcaaaaccgt   3480
caccagtagt agatttaccc tcttctaatg atctctttct caattcatcc attacgaaca   3540
agacagtgga tgaagacatg ttaccgtgtt cagataaaac atgtctacta tctacaaact   3600
tttctttctt caaatccaat ttttcttcaa ccttatccaa aatggcttta ccacctggat   3660
gtgttatcca gaaaatagag ttccaatctg agatacctat aggagtgaat gcttctatca   3720
aacacttttc tatgttgtta gagattaaca ttggaacgtc tttgtgcaaa tcgaagatca   3780
aacctgcttc tcttatatga ccaccaattg taccttcaga attaggcaag atggtttgac   3840
ctgtactgac taattcaaat attggtcttt caccaacaga ttcgtcaggt tctgcaccaa   3900
caataacagc agcagcaccg tcaccgaaga tagcttgacc aactaacaat tccaagtcag   3960
aatcacttgg acctctaaac aagcaagcca taatgtcgca acaaacagct aatactctgg   4020
cacccttgtt gttttctgca atatccttag cgattctcaa aacagtacca ccaccgtagc   4080
aacctaattg atacatcatg actctcttaa cggatggtga caaacctaac aatttggcac   4140
agtggtagtc tgcaccaggc atatctgtag tagatgcact tgtaaaaatc aaatgagtga   4200
tctttgactt tggttgaccc cattccttaa tggcttttgc acaagcatct ttacccaatt   4260
taggaacttc gacaactaac atgtcttgtc tggcatccaa tgtttgcatt tcgtgttcta   4320
ccaatcttgg attttgcttc aaatgttctt cgttcaagaa gcagtttctc tttctgatca   4380
tagacttatc acatattttt ctaaactttt ccttcaattg agtcatgtgt tcactcttgg   4440
taactctgaa gtaataatca ggaaattcat cttggatcaa tatgttttct gggttggctg   4500
tacctatggc taatacggag gcaggacctt cggctctcaa atggttcata ctagttctag   4560
atccgtcgaa actaagttct tggtgtttta aaactaaaaa aaagactaac tataaaagta   4620
gaatttaaga agtttaagaa atagatttac agaattacaa tcaataccta ccgtctttat   4680
atacttatta gtcaagtagg ggaataattt cagggaactg gtttaaacct ttttttttcag   4740
ctttttccaa atcagagaga gcagaaggta atagaaggtg taagaaaatg agatagatac   4800
atgcgtgggt caattgcctt gtgtcatcat ttactccagg caggttgcat cactccattg   4860
aggttgtgcc cgtttttttgc ctgtttgtgc cctgttctct gtagttgcgc taagagaatg   4920
gacctatgaa ctgatggttg gtgaagaaaa caatattttg gtgctgggat tcttttttttt   4980
tctggatgcc agcttaaaaa gcgggctcca ttatatttag tggatgccag gaataaacct   5040
gttcacccaa gcaccatcag tgttatatat tctgtgtaac ccgcccccta ttttggcatg   5100
tacgggttac agcagaatta aaaggctaat tttttgacta aataaagtta ggaaaatcac   5160
tactattaat tatttacgta ttctttgaaa tggcagtatt gataatgata aactcgagag   5220
ctccagcttt tgttcagttg attgtatgct tggtatagct tgaaatattg tgcagaaaaa   5280
gaaacaagga agaaagggaa cgagaacaat gacgaggaaa caaaagatta ataattgcag   5340
```

-continued

```
gtctatttat acttgatagc aagacagcaa acttttttt atttcaaatt caagtaactg   5400
gaaggaaggc cgtataccgt tgctcattag agagtagtgt gcgtgaatga aggaaggaaa   5460
aagtttcgtg tgcttcgaga taccccctcat cagctctgga acaacgacat ctgttggtgc   5520
tgtctttgtc gttaattttt tcctttagtg tcttccatca tttttttgtc attgcggata   5580
tggtgagaca acaacggggg agagagaaaa gaaaaaaaaa gaaaagaagt tgcatgcgcc   5640
tattattact tcaatagatg gcaaatggaa aaagggtagt gaaacttcga tatgatgatg   5700
gctatcaagt ctagggctac agtattagtt cgttatgtac caccatcaat gaggcagtgt   5760
aattggtgta gtcttgttta gcccattatg tcttgtctgg tatctgttct attgtatatc   5820
tcccctccgc cacctacatg ttagggagac caacgaaggt attataggaa tcccgatgta   5880
tgggtttggt tgccagaaaa gaggaagtcc atattgtaca cccggaaaca acaaaaggat   5940
gcgcgcttgg cgtaatcatg gtcatagctg tttcctgtgt gaaattgtta tccgctcaca   6000
attccacaca acataggagc cggaagcata aagtgtaaag cctggggtgc ctaatgagtg   6060
aggtaactca cattaattgc gttgcgctca ctgcccgctt tccagtcggg aaacctgtcg   6120
tgccagctgc attaatgaat cggccaacgc gcggggagag gcggtttgcg tattgggcgc   6180
tcttccgctt cctcgctcac tgactcgctg cgctcggtcg ttcggctgcg gcgagcggta   6240
tcagctcact caaaggcggt aatacggtta tccacagaat caggggataa cgcaggaaag   6300
aacatgtgag caaaaggcca gcaaaaggcc aggaaccgta aaaaggccgc gttgctggcg   6360
tttttccata ggctccgccc ccctgacgag catcacaaaa atcgacgctc aagtcagagg   6420
tggcgaaacc cgacaggact ataaagatac caggcgtttc cccctggaag ctccctcgtg   6480
cgctctcctg ttccgaccct gccgcttacc ggatacctgt ccgcctttct cccttcggga   6540
agcgtggcgc tttctcatag ctcacgctgt aggtatctca gttcggtgta ggtcgttcgc   6600
tccaagctgg gctgtgtgca cgaacccccc gttcagcccg accgctgcgc cttatccggt   6660
aactatcgtc ttgagtccaa cccggtaaga cacgacttat cgccactggc agcagccact   6720
ggtaacagga ttagcagagc gaggtatgta ggcggtgcta cagagttctt gaagtggtgg   6780
cctaactacg gctacactag aaggacagta tttggtatct gcgctctgct gaagccagtt   6840
accttcggaa aaagagttgg tagctcttga tccggcaaac aaaccaccgc tggtagcggt   6900
ggtttttttg tttgcaagca gcagattacg cgcagaaaaa aaggatctca agaagatcct   6960
ttgatctttt ctacggggtc tgacgctcag tggaacgaaa actcacgtta agggattttg   7020
gtcatgagat tatcaaaaag gatcttcacc tagatccttt taaattaaaa atgaagtttt   7080
aaatcaatct aaagtatata tgagtaaact tggtctgaca gttaccaatg cttaatcagt   7140
gaggcaccta tctcagcgat ctgtctattt cgttcatcca tagttgcctg actccccgtc   7200
gtgtagataa ctacgatacg ggagggctta ccatctggcc ccagtgctgc aatgataccg   7260
cgagacccac gctcaccggc tccagattta tcagcaataa accagccagc cggaagggcc   7320
gagcgcagaa gtggtcctgc aactttatcc gcctccatcc agtctattaa ttgttgccgg   7380
gaagctagag taagtagttc gccagttaat agtttgcgca acgttgttgc cattgctaca   7440
ggcatcgtgg tgtcacgctc gtcgtttggt atggcttcat tcagctccgg ttcccaacga   7500
tcaaggcgag ttacatgatc ccccatgttg tgcaaaaaag cggttagctc cttcggtcct   7560
ccgatcgttg tcagaagtaa gttggccgca gtgttatcac tcatggttat ggcagcactg   7620
cataattctc ttactgtcat gccatccgta agatgctttt ctgtgactgg tgagtactca   7680
accaagtcat tctgagaata gtgtatgcgg cgaccgagtt gctcttgccc ggcgtcaata   7740
```

```
cgggataata ccgcgccaca tagcagaact ttaaaagtgc tcatcattgg aaaacgttct   7800

tcggggcgaa aactctcaag gatcttaccg ctgttgagat ccagttcgat gtaacccact   7860

cgtgcaccca actgatcttc agcatctttt actttcacca gcgtttctgg gtgagcaaaa   7920

acaggaaggc aaaatgccgc aaaaaaggga ataagggcga cacggaaatg ttgaatactc   7980

atactcttcc tttttcaata ttattgaagc atttatcagg gttattgtct catgagcgga   8040

tacatatttg aatgtattta gaaaaataaa caaatagggg ttccgcgcac atttccccga   8100

aaagtgccac ctgggtcctt ttcatcacgt gctataaaaa taattataat ttaaattttt   8160

taatataaat atataaatta aaaatagaaa gtaaaaaaag aaattaaaga aaaaatagtt   8220

tttgttttcc gaagatgtaa aagactctag ggggatcgcc aacaaatact accttttatc   8280

ttgctcttcc tgctctcagg tattaatgcc gaattgtttc atcttgtctg tgtagaagac   8340

cacacacgaa aatcctgtga ttttacattt tacttatcgt taatcgaatg tatatctatt   8400

taatctgctt ttcttgtcta ataaatatat atgtaaagta cgctttttgt tgaaattttt   8460

taaacctttg tttatttttt tttcttcatt ccgtaactct tctaccttct ttatttactt   8520

tctaaaatcc aaatacaaaa cataaaaata aataaacaca gagtaaattc ccaaattatt   8580

ccatcattaa aagatacgag gcgcgtgtaa gttacaggca agcgatccgt cctaagaaac   8640

cattattatc atgacattaa cctataaaaa taggcgtatc acgaggccct ttcgtc       8696
```

<210> SEQ ID NO 6
<211> LENGTH: 4322
<212> TYPE: DNA
<213> ORGANISM: Artificial Sequence
<220> FEATURE:
<223> OTHER INFORMATION: Codon optimized

<400> SEQUENCE: 6

```
aggaaacgaa gataaatctc gagtttatca ttatcaatac tgccatttca aagaatacgt     60

aaataattaa tagtagtgat ttcctaact ttatttagtc aaaaaattag ccttttaatt    120

ctgctgtaac ccgtacatgc caaaataggg ggcgggttac acagaatata taacactgat    180

ggtgcttggg tgaacaggtt tattcctggc atccactaaa tataatggag cccgcttttt    240

aagctggcat ccagaaaaaa aaagaatccc agcaccaaaa tattgttttc ttcaccaacc    300

atcagttcat aggtccattc tcttagcgca actacagaga acagggcaca aacaggcaaa    360

aaacgggcac aacctcaatg gagtgatgca acctgcctgg agtaaatgat gacacaaggc    420

aattgaccca cgcatgtatc tatctcattt tcttacacct tctattacct tctgctctct    480

ctgatttgga aaaagctgaa aaaaaaggtt taaaccagtt ccctgaaatt attcccctac    540

ttgactaata agtatataaa gacggtaggt attgattgta attctgtaaa tctatttctt    600

aaacttctta aattctactt ttatagttag tctttttttt agttttaaaa caccaagaac    660

ttagtttcga cggatctaga actagtatgg gtaaaaacta taagtccttg gattcagtcg    720

ttgcctcaga tttcatcgca ttgggtatca cctcagaagt agcagaaaca ttacatggta    780

gattggcaga aatcgtttgt aattatggtg ctgcaacccc tcaaacttgg atcaacatcg    840

ctaaccatat cttgtcacca gatttgcctt tctccttaca ccaaatgttg ttttatggtt    900

gctacaagga tttcggtcca gccccacctg cttggattcc agaccctgaa aaagtcaagt    960

caactaattt gggtgctttg ttggaaaaga gaggtaaaga atttttgggt gtaaagtaca   1020

aagatccaat ttcttctttt tctcacttcc aagaattttc tgttagaaac cctgaagtct   1080
```

-continued

```
attggagaac agtattgatg gatgaaatga aaattagttt ctctaaggac ccagaatgta   1140
tcttgagaag agatgacatc aacaacccag gtggttctga atggttacct ggtggttact   1200
tgaactcagc taaaaattgc ttgaacgtaa actccaataa gaaattgaac gatactatga   1260
tcgtttggag agacgagggt aacgatgact tgcctttgaa taagttgaca ttagatcaat   1320
tgagaaagag agtttggttg gttggttatg cattggaaga aatgggttta gaaaaaggtt   1380
gtgcaatagc catcgatatg ccaatgcatg ttgatgctgt tgttatatat ttggccatag   1440
tattggctgg ttacgtagtt gtctctatag cagattcatt ttccgcccct gaaatctcaa   1500
ctagattgag attatccaaa gctaaggcaa ttttcacaca agatcacatc atcagaggta   1560
aaaagagaat accattgtat tcaagagtag ttgaagctaa atccccaatg gcaatagtta   1620
tcccttgtag tggttctaac attggtgcag aattgagaga tggtgacata tcttgggatt   1680
actttttaga aagagccaag gagtttaaaa actgcgagtt tactgccaga gaacaacctg   1740
ttgatgctta tactaacatc ttattctcca gtggtactac aggtgaacca aaagcaattc   1800
cttggacaca agccacccca ttgaaggctg ctgctgatgg ttggtctcat ttggatatta   1860
gaaaaggtga cgttatagta tggccaacta atttgggttg gatgatgggt ccttggttgg   1920
tttatgctag tttgttaaat ggtgcatcta ttgccttgta caacggtagt cctttagtct   1980
ctggtttcgc taaatttgtt caagatgcaa aggtcacaat gttgggtgtc gtaccatcta   2040
ttgtaagatc atggaaatcc acaaattgtg tttcaggtta cgattggtcc accataagat   2100
gcttttcttc atccggtgaa gcctctaatg tagacgaata tttgtggtta atgggtagag   2160
ctaactacaa gccagttata gaaatgtgtg gtggtacaga aatcggtggt gctttttctg   2220
ctggttcatt tttgcaagct caatctttaa gttctttttc atcccaatgt atgggttgca   2280
ccttgtacat attagataag aacggttacc caatgcctaa aaataagcca ggtatcggtg   2340
aattggcatt aggtcctgtt atgtttggtg cctcaaaaac attgttaaac ggtaatcatc   2400
acgatgtcta tttcaagggt atgccaacct tgaatggtga agtattgaga agacatggtg   2460
acattttcga attgacctct aacggttact accatgcaca cggtagagcc gatgacacta   2520
tgaacatcgg tggtatcaaa attagttcta tcgaaatcga aagagtctgt aatgaagtag   2580
atgacagagt tttgaaacc actgctattg gtgttccacc tttgggtggt ggtccagaac   2640
aattggtcat atttttcgta ttgaaggatt caaacgacac aaccattgat ttgaaccaat   2700
tgagattatc ctttaacttg ggtttgcaaa agaaattgaa cccattattc aaagttacta   2760
gagttgtccc attgtcatcc ttacctagaa ctgcaacaaa caagatcatg agaagagttt   2820
tgagacaaca attcagtcat ttcgaagaag gtagaggttc tttgttaaca tgtggtgacg   2880
ttgaagaaaa tccaggtcct atggcttcag aaaaggaaat aagaagagaa agattcttga   2940
acgtattccc aaagttagtt gaagaattga acgctagttt gttagcttat ggtatgccta   3000
aagaagcctg cgattggtat gctcactctt taaactacaa tactccaggt ggtaaattga   3060
atagaggttt gagtgtagtt gatacttatg ctatcttgtc taacaaaacc gttgaacaat   3120
taggtcaaga agaatacgaa aaggtcgcta tcttgggttg gtgtattgaa ttgttgcaag   3180
catacttttt ggttgccgat gacatgatgg ataagtctat aacaagaaga ggtcaaccat   3240
gctggtacaa agttccagaa gttggtgaaa tagccataaa tgatgctttt atgttggaag   3300
ccgctatcta taaattgttg aagtcacatt tcagaaacga aaagtactac atcgatatta   3360
ccgaattatt ccacgaagtt actttccaaa cagaattggg tcaattgatg gatttgataa   3420
ctgcacctga agataaagtt gacttgtcaa agttttcctt gaagaaacat tcattcatcg   3480
```

```
tcacctttga aactgcttat tactccttct atttgccagt cgccttggct atgtacgtag   3540

ctggtattac tgatgaaaaa gacttgaagc aagcaagaga tgttttgata cctttgggtg   3600

aatacttcca aatccaagat gactacttag actgtttcgg tactccagaa caaataggta   3660

aaatcggtac agatattcaa gacaataagt gcagttgggt tattaacaag gctttggaat   3720

tagcatctgc cgaacaaaga aagactttgg atgaaaacta cggtaaaaag gactcagttg   3780

ctgaagcaaa gtgtaagaaa atttttaatg atttgaagat tgaacaattg taccatgaat   3840

acgaagaatc catcgctaaa gacttaaagg caaagattag tcaagttgat gaatcaagag   3900

gttttaaagc cgacgttttg acagctttct tgaataaggt ctacaagaga tcaaaggatt   3960

acaaggatca tgacggtgac tataaagacc acgatattga ctacaaagat gacgatgaca   4020

agtaagtcga cctcgagtca tgtaattagt tatgtcacgc ttacattcac gccctccccc   4080

cacatccgct ctaaccgaaa aggaaggagt tagacaacct gaagtctagg tccctattta   4140

tttttttata gttatgttag tattaagaac gttatttata tttcaaattt ttcttttttt   4200

tctgtacaga cgcgtgtacg catgtaacat tatactgaaa accttgcttg agaaggtttt   4260

gggacgctcg aaggctttaa tttgcgtgac ataactaatt acatgacttg actgattttt   4320

cc                                                                  4322
```

<210> SEQ ID NO 7
<211> LENGTH: 2522
<212> TYPE: DNA
<213> ORGANISM: Artificial Sequence
<220> FEATURE:
<223> OTHER INFORMATION: Codon optimized

<400> SEQUENCE: 7

```
aggaaacgaa gataaatctc gagtttatca ttatcaatac tgccatttca aagaatacgt     60

aaataattaa tagtagtgat tttcctaact ttatttagtc aaaaaattag ccttttaatt    120

ctgctgtaac ccgtacatgc caaaataggg ggcgggttac acagaatata taacactgat    180

ggtgcttggg tgaacaggtt tattcctggc atccactaaa tataatggag cccgcttttt    240

aagctggcat ccagaaaaaa aaagaatccc agcaccaaaa tattgttttc ttcaccaacc    300

atcagttcat aggtccattc tcttagcgca actacagaga acagggcaca aacaggcaaa    360

aaacgggcac aacctcaatg gagtgatgca acctgcctgg agtaaatgat gacacaaggc    420

aattgaccca cgcatgtatc tatctcattt tcttacacct tctattacct tctgctctct    480

ctgatttgga aaaagctgaa aaaaaaggtt taaaccagtt ccctgaaatt attcccctac    540

ttgactaata agtatataaa gacggtaggt attgattgta attctgtaaa tctatttctt    600

aaacttctta aattctactt ttatagttag tctttttttt agttttaaaa caccaagaac    660

ttagtttcga cggatctaga actagtatga accatttgag agccgaaggt cctgcctccg    720

tattagccat aggtacagcc aacccagaaa acatattgat ccaagatgaa tttcctgatt    780

attacttcag agttaccaag agtgaacaca tgactcaatt gaaggaaaag tttagaaaaa    840

tatgtgataa gtctatgatc agaaagagaa actgcttctt gaacgaagaa catttgaagc    900

aaaatccaag attggtagaa cacgaaatgc aaacattgga tgccagacaa gacatgttag    960

ttgtcgaagt tcctaaattg ggtaaagatg cttgtgcaaa agccattaag gaatggggtc   1020

aaccaaagtc aaagatcact catttgattt ttacaagtgc atctactaca gatatgcctg   1080

gtgcagacta ccactgtgcc aaattgttag gtttgtcacc atccgttaag agagtcatga   1140
```

```
tgtatcaatt aggttgctac ggtggtggta ctgttttgag aatcgctaag gatattgcag   1200

aaaacaacaa gggtgccaga gtattagctg tttgttgcga cattatggct tgcttgttta   1260

gaggtccaag tgattctgac ttggaattgt tagttggtca agctatcttc ggtgacggtg   1320

ctgctgctgt tattgttggt gcagaacctg acgaatctgt tggtgaaaga ccaatatttg   1380

aattagtcag tacaggtcaa accatcttgc ctaattctga aggtacaatt ggtggtcata   1440

taagagaagc aggtttgatc ttcgatttgc acaaagacgt tccaatgtta atctctaaca   1500

acatagaaaa gtgtttgata gaagcattca ctcctatagg tatctcagat tggaactcta   1560

ttttctggat aacacatcca ggtggtaaag ccattttgga taaggttgaa gaaaaattgg   1620

atttgaagaa agaaaagttt gtagatagta gacatgtttt atctgaacac ggtaacatgt   1680

cttcatccac tgtcttgttc gtaatggatg aattgagaaa gagatcatta gaagagggta   1740

aatctactac tggtgacggt tttgaatggg gtgtcttatt tggtttcggt cctggtttga   1800

ccgtcgaaag agtagttgtc agatcagtac caattaaata tgaaggtaga ggttccttgt   1860

taacttgtgg tgacgttgaa gaaaacccag gtcctatggc cgtcaagcat ttgatagtat   1920

tgaagtttaa agatgaaatc acagaagctc aaaaggaaga atttttcaag acctacgtta   1980

atttggtcaa cattatacct gctatgaaag atgtatactg ggtaaagac gttacacaaa   2040

agaaagaaga aggttataca cacattgtcg aagtaacctt cgaatcagtt gaaactatcc   2100

aagattacat cattcatcca gctcacgttg gttttggtga cgtttacaga tccttctggg   2160

aaaaattgtt gatcttcgat tacaccccaa gaaagtaccc ttacgatgtt ccagactatg   2220

cataagtcga cctcgagtca tgtaattagt tatgtcacgc ttacattcac gccctccccc   2280

cacatccgct ctaaccgaaa aggaaggagt tagacaacct gaagtctagg tccctattta   2340

tttttttata gttatgttag tattaagaac gttatttata tttcaaattt ttcttttttt   2400

tctgtacaga cgcgtgtacg catgtaacat tatactgaaa accttgcttg agaaggtttt   2460

gggacgctcg aaggctttaa tttgcgtgac ataactaatt acatgacttg actgattttt   2520

cc                                                                  2522
```

<210> SEQ ID NO 8
<211> LENGTH: 3887
<212> TYPE: DNA
<213> ORGANISM: Artificial Sequence
<220> FEATURE:
<223> OTHER INFORMATION: Codon optimized

<400> SEQUENCE: 8

```
aggaaacgaa gataaatctc gagtttatca ttatcaatac tgccatttca aagaatacgt     60

aaataattaa tagtagtgat ttcctaact ttatttagtc aaaaaattag ccttttaatt     120

ctgctgtaac ccgtacatgc caaaataggg ggcgggttac acagaatata taacactgat    180

ggtgcttggg tgaacaggtt tattcctggc atccactaaa tataatggag cccgcttttt    240

aagctggcat ccagaaaaaa aaagaatccc agcaccaaaa tattgttttc ttcaccaacc    300

atcagttcat aggtccattc tcttagcgca actacagaga acagggcaca aacaggcaaa    360

aaacgggcac aacctcaatg gagtgatgca acctgcctgg agtaaatgat gacacaaggc    420

aattgaccca cgcatgtatc tatctcattt tcttacacct tctattacct tctgctctct    480

ctgatttgga aaaagctgaa aaaaaaggtt taaaccagtt ccctgaaatt attcccctac    540

ttgactaata agtatataaa gacggtaggt attgattgta attctgtaaa tctatttctt    600

aaacttctta aattctactt ttatagttag tcttttttt agttttaaaa caccaagaac     660
```

-continued

```
ttagtttcga cggatctaga actagtatgg gtttatcatc cgtctgtact ttctccttcc    720

aaactaacta tcatacctta ttgaatcctc acaacaacaa tccaaaaaca tcattgttgt    780

gttacagaca tccaaagaca cctattaagt actcttacaa caactttcca tcaaaacatt    840

gttcaaccaa gtccttccac ttacaaaata agtgctccga aagtttgtct atagctaaga    900

actctatcag agctgcaact acaaatcaaa ctgaaccacc tgaaagtgat aatcactctg    960

ttgccacaaa aattttgaac ttcggtaaag catgttggaa gttgcaaaga ccatacacca   1020

taatcgcttt tacttcttgt gcatgcggtt tattcggtaa agaattgttg cataacacta   1080

acttaatttc atggtccttg atgttcaagg catttttctt tttagttgcc atcttgtgca   1140

tcgcttcatt caccactaca attaatcaaa tatacgattt gcacatcgac agaattaaca   1200

aaccagattt gcctttggct tcaggtgaaa tatccgtcaa tactgcatgg atcatgtcta   1260

tcatagtagc cttgttcggt ttgatcatca caattaaaat gaagggtggt ccattgtaca   1320

tcttcggtta ctgtttcggt atcttcggtg gtattgtcta ttccgtacca ccttttagat   1380

ggaaacaaaa ccctagtact gcctttttgt tgaatttctt agctcatatc atcacaaact   1440

tcaccttcta ctacgcttca agagctgctt taggtttgcc attcgaattg agaccttcat   1500

tcacattttt gttggcattc atgaaaagta tgggttctgc attagccttg atcaaggatg   1560

cctctgacgt tgaaggtgac acaaagttcg gtattagtac cttggcttct aagtacggtt   1620

caagaaattt gactttgttc tgctccggta tcgttttgtt aagttacgtc gcagccattt   1680

tggcaggtat catttggcca caagccttta attctaacgt tatgttgttg tcacatgcca   1740

tcttggcttt ctggttgatc ttgcaaacta gagatttcgc tttgacaaat tatgaccctg   1800

aagcaggtag aagattctac gagtttatgt ggaaattgta ctacgctgaa tatttggtat   1860

acgtttttat tgaaggtaga ggttctttgt tgacctgtgg tgacgttgaa gaaaatccag   1920

gtcctatgaa atgttcaact ttctcctttt ggttcgtatg caagatcatc ttcttttttct   1980

tttcctttaa catccaaaca agtatcgcaa acccaagaga aaactttttg aagtgcttct   2040

cacaatacat acctaataac gccaccaatt tgaagttggt ttacactcaa aacaacccat   2100

tgtacatgtc cgtcttgaac agtacaatcc ataatttgag attcacttct gataccactc   2160

caaaaccttt ggtcattgta acccctagtc atgtatctca catccaaggt actatcttat   2220

gttctaaaaa ggttggtttg caaattagaa ctagatccgg tggtcatgat agtgaaggca   2280

tgtcatacat ctcccaagtt ccattcgtta tcgttgattt gagaaacatg agatcaatta   2340

aaatagacgt acactcacaa actgcttggg ttgaagctgg tgcaacattg ggtgaagtat   2400

actactgggt taacgaaaag aatgaaaact tatcattggc tgctggttac tgtccaacag   2460

tttgcgcagg tggtcatttt ggtggtggtg gttatggtcc tttaatgaga aactacggtt   2520

tggccgctga taacataatc gacgctcatt tggtaaatgt tcacggtaaa gttttggata   2580

gaaagtctat gggtgaagac ttattttggg ctttgagagg tggtggtgca gaatcattcg   2640

gtatcatagt tgcttggaag ataagattag tcgcagtacc aaagtctact atgttctcag   2700

tcaaaaagat aatggaaatc catgaattag ttaaattggt caataagtgg caaaacatcg   2760

catacaagta cgataaggac ttgttgttga tgactcattt catcacaaga aacatcaccg   2820

ataaccaagg taaaaataag actgctatcc acacatactt ttcttcagtt ttcttgggtg   2880

gtgtcgattc cttagtagac ttgatgaata agtcttttcc agaattaggt attaagaaaa   2940

ctgattgtag acaattgtct tggatcgaca ccatcatctt ttattcaggt gttgtcaact   3000
```

```
acgatacaga caacttcaac aaagaaatat tattggatag atccgcaggt caaaacggtg   3060

cctttaaaat taagttagac tacgttaaaa agccaatacc tgaatcagtt ttcgtccaaa   3120

tcttagaaaa attgtacgaa gaagatattg gtgcaggcat gtacgccttg tatccatacg   3180

gtggtataat ggacgaaatc agtgaatctg ccattccatt tcctcataga gctggtatct   3240

tatacgaatt gtggtacatt tgttcatggg aaaagcaaga agataacgaa aagcacttaa   3300

actggattag aaacatctat aacttcatga ctccatacgt ttctaaaaac cctagattgg   3360

catatttgaa ctacagagat ttggacatcg gtattaacga tccaaagaat cctaacaact   3420

atacccaagc tagaatttgg ggtgaaaaat acttcggtaa aaatttcgat agattagtaa   3480

aggttaagac attggttgac ccaaacaact tctttagaaa cgaacaatcc attccacctt   3540

tacctagaca tagacacgaa caaaaattaa taagtgaaga agatttgtaa gtcgacctcg   3600

agtcatgtaa ttagttatgt cacgcttaca ttcacgccct ccccccacat ccgctctaac   3660

cgaaaaggaa ggagttagac aacctgaagt ctaggtccct atttattttt ttatagttat   3720

gttagtatta agaacgttat ttatatttca aatttttctt ttttttctgt acagacgcgt   3780

gtacgcatgt aacattatac tgaaaacctt gcttgagaag gttttgggac gctcgaaggc   3840

tttaatttgc gtgacataac taattacatg acttgactga tttttcc                 3887
```

<210> SEQ ID NO 9
<211> LENGTH: 8963
<212> TYPE: DNA
<213> ORGANISM: Artificial Sequence
<220> FEATURE:
<223> OTHER INFORMATION: Codon optimized

<400> SEQUENCE: 9

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct ttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600

agagaacaat tgacccggtt attgcaagga aaatttcaag tcttgtaaaa gcatataaaa    660

atagttcagg cactccgaaa tacttggttg gcgtgtttcg taatcaacct aaggaggatg    720

ttttggctct ggtcaatgat tacggcattg atatcgtcca actgcatgga gatgagtcgt    780

ggcaagaata ccaagagttc ctcggtttgc cagttattaa aagactcgta tttccaaaag    840

actgcaacat actactcagt gcagcttcac agaaacctca ttcgtttatt cccttgtttg    900

attcagaagc aggtgggaca ggtgaacttt tggattggaa ctcgatttct gactgggttg    960

gaaggcaaga gagccccgaa agcttacatt ttatgttagc tggtggactg acgccagaaa   1020

atgttggtga tgcgcttaga ttaaatggcg ttattggtgt tgatgtaagc ggaggtgtgg   1080

agacaaatgg tgtaaaagac tctaacaaaa tagcaaattt cgtcaaaaat gctaagaaat   1140

aggttattac tgagtagtat ttatttaagt attgtttgtg cacttgccta tgcggtgtga   1200
```

```
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttacttg tcatcgtcat ctttgtagtc aatatcgtgg tctttatagt caccgtcatg   2220
atccttgtaa tcctttgatc tcttgtagac cttattcaag aaagctgtca aaacgtcggc   2280
tttaaaacct cttgattcat caacttgact aatctttgcc tttaagtctt tagcgatgga   2340
ttcttcgtat tcatggtaca attgttcaat cttcaaatca ttaaaaattt tcttacactt   2400
tgcttcagca actgagtcct tttaccgta gttttcatcc aaagtctttc tttgttcggc   2460
agatgctaat tccaaagcct tgttaataac ccaactgcac ttattgtctt gaatatctgt   2520
accgatttta cctatttgtt ctggagtacc gaaacagtct aagtagtcat cttggatttg   2580
gaagtattca cccaaaggta tcaaaacatc tcttgcttgc ttcaagtctt tttcatcagt   2640
aataccagct acgtacatag ccaaggcgac tggcaaatag aaggagtaat aagcagtttc   2700
aaaggtgacg atgaatgaat gtttcttcaa ggaaaacttt gacaagtcaa ctttatcttc   2760
aggtgcagtt atcaaatcca tcaattgacc caattctgtt tggaaagtaa cttcgtggaa   2820
taattcggta atatcgatgt agtacttttc gtttctgaaa tgtgacttca acaatttata   2880
gatagcggct tccaacataa aagcatcatt tatggctatt tcaccaactt ctggaacttt   2940
gtaccagcat ggttgacctc ttcttgttat agacttatcc atcatgtcat cggcaaccaa   3000
aaagtatgct tgcaacaatt caatacacca acccaagata gcgacctttt cgtattcttc   3060
ttgacctaat tgttcaacgg ttttgttaga caagatagca taagtatcaa ctacactcaa   3120
acctctattc aatttaccac ctggagtatt gtagtttaaa gagtgagcat accaatcgca   3180
ggcttcttta ggcataccat aagctaacaa actagcgttc aattcttcaa ctaactttgg   3240
gaatacgttc aagaatcttt ctcttcttat ttccttttct gaagccatag gacctggatt   3300
ttcttcaacg tcaccacatg ttaacaaaga acctctacct tcttcgaaat gactgaattg   3360
ttgtctcaaa actcttctca tgatcttgtt tgttgcagtt ctaggtaagg atgacaatgg   3420
gacaactcta gtaactttga ataatgggtt caatttcttt tgcaaaccca agttaaagga   3480
taatctcaat tggttcaaat caatggttgt gtcgtttgaa tccttcaata cgaaaaatat   3540
```

-continued

```
gaccaattgt tctggaccac cacccaaagg tggaacacca atagcagtgg tttcaaaaac   3600
tctgtcatct acttcattac agactctttc gatttcgata gaactaattt tgataccacc   3660
gatgttcata gtgtcatcgg ctctaccgtg tgcatggtag taaccgttag aggtcaattc   3720
gaaaatgtca ccatgtcttc tcaatacttc accattcaag gttggcatac ccttgaaata   3780
gacatcgtga tgattaccgt ttaacaatgt ttttgaggca ccaaacataa caggacctaa   3840
tgccaattca ccgatacctg gcttattttt aggcattggg taaccgttct tatctaatat   3900
gtacaaggtg caacccatac attgggatga aaaagaactt aaagattgag cttgcaaaaa   3960
tgaaccagca gaaaaagcac caccgatttc tgtaccacca cacatttcta taactggctt   4020
gtagttagct ctacccatta accacaaata ttcgtctaca ttagaggctt caccggatga   4080
agaaaagcat cttatggtgg accaatcgta acctgaaaca caatttgtgg atttccatga   4140
tcttacaata gatggtacga cacccaacat tgtgaccttt gcatcttgaa caaatttagc   4200
gaaaccagag actaaaggac taccgttgta caaggcaata gatgcaccat ttaacaaact   4260
agcataaacc aaccaaggac ccatcatcca acccaaatta gttggccata ctataacgtc   4320
acctttteta atatccaaat gagaccaacc atcagcagca gccttcaatg gggtggcttg   4380
tgtccaagga attgcttttg gttcacctgt agtaccactg gagaataaga tgttagtata   4440
agcatcaaca ggttgttctc tggcagtaaa ctcgcagttt ttaaactcct tggctctttc   4500
taaaaagtaa tcccaagata tgtcaccatc tctcaattct gcaccaatgt tagaaccact   4560
acaagggata actattgcca ttggggattt agcttcaact actcttgaat acaatggtat   4620
tctcttttta cctctgatga tgtgatcttg tgtgaaaatt gccttagctt tggataatct   4680
caatctagtt gagatttcag gggcggaaaa tgaatctgct atagagacaa ctacgtaacc   4740
agccaatact atggccaaat atataacaac agcatcaaca tgcattggca tatcgatggc   4800
tattgcacaa cctttttcta aacccatttc ttccaatgca taaccaacca accaaactct   4860
ctttctcaat tgatctaatg tcaacttatt caaaggcaag tcatcgttac cctcgtctct   4920
ccaaacgatc atagtatcgt tcaatttctt attggagttt acgttcaagc aatttttagc   4980
tgagttcaag taaccaccag gtaaccattc agaaccacct gggttgttga tgtcatctct   5040
tctcaagata cattctgggt ccttagagaa actaattttc atttcatcca tcaatactgt   5100
tctccaatag acttcagggt ttctaacaga aaattcttgg aagtgagaaa aagaagaaat   5160
tggatctttg tactttacac ccaaaaattc tttacctctc ttttccaaca aagcacccaa   5220
attagttgac ttgacttttt cagggtctgg aatccaagca ggtggggctg gaccgaaatc   5280
cttgtagcaa ccataaaaca acatttggtg taaggagaaa ggcaaatctg gtgacaagat   5340
atggttagcg atgttgatcc aagtttgagg ggttgcagca ccataattac aaacgatttc   5400
tgccaatcta ccatgtaatg tttctgctac ttctgaggtg atacccaatg cgatgaaatc   5460
tgaggcaacg actgaatcca aggacttata gtttttaccc atactagttc tagatccgtc   5520
gaaactaagt tcttggtgtt ttaaaactaa aaaaaagact aactataaaa gtagaattta   5580
agaagtttaa gaaatagatt tacagaatta caatcaatac ctaccgtctt tatatactta   5640
ttagtcaagt aggggaataa tttcagggaa ctggtttaaa cctttttttt cagcttttc    5700
caaatcagag agagcagaag gtaatagaag gtgtaagaaa atgagataga tacatgcgtg   5760
ggtcaattgc cttgtgtcat catttactcc aggcaggttg catcactcca ttgaggttgt   5820
gcccgttttt tgcctgtttg tgccctgttc tctgtagttg cgctaagaga atggacctat   5880
gaactgatgg ttggtgaaga aaacaatatt ttggtgctgg gattcttttt ttttctggat   5940
```

```
gccagcttaa aaagcgggct ccattatatt tagtggatgc caggaataaa cctgttcacc   6000
caagcaccat cagtgttata tattctgtgt aacccgcccc ctattttggc atgtacgggt   6060
tacagcagaa ttaaaaggct aatttttga ctaaataaag ttaggaaaat cactactatt   6120
aattatttac gtattctttg aaatggcagt attgataatg ataaactcga gagctccagc   6180
ttttgttccc tttagtgagg gttaattgcg cgcttggcgt aatcatggtc atagctgttt   6240
cctgtgtgaa attgttatcc gctcacaatt ccacacaaca taggagccgg aagcataaag   6300
tgtaaagcct ggggtgccta atgagtgagg taactcacat taattgcgtt gcgctcactg   6360
cccgctttcc agtcgggaaa cctgtcgtgc cagctgcatt aatgaatcgg ccaacgcgcg   6420
gggagaggcg gtttgcgtat tgggcgctct tccgcttcct cgctcactga ctcgctgcgc   6480
tcggtcgttc ggctgcggcg agcggtatca gctcactcaa aggcggtaat acggttatcc   6540
acagaatcag gggataacgc aggaaagaac atgtgagcaa aaggccagca aaaggccagg   6600
aaccgtaaaa aggccgcgtt gctggcgttt ttccataggc tccgcccccc tgacgagcat   6660
cacaaaaatc gacgctcaag tcagaggtgg cgaaacccga caggactata aagataccag   6720
gcgtttcccc ctggaagctc cctcgtgcgc tctcctgttc cgaccctgcc gcttaccgga   6780
tacctgtccg cctttctccc ttcgggaagc gtggcgcttt ctcatagctc acgctgtagg   6840
tatctcagtt cggtgtaggt cgttcgctcc aagctgggct gtgtgcacga accccccgtt   6900
cagcccgacc gctgcgcctt atccggtaac tatcgtcttg agtccaaccc ggtaagacac   6960
gacttatcgc cactggcagc agccactggt aacaggatta gcagagcgag gtatgtaggc   7020
ggtgctacag agttcttgaa gtggtggcct aactacggct acactagaag gacagtattt   7080
ggtatctgcg ctctgctgaa gccagttacc ttcggaaaaa gagttggtag ctcttgatcc   7140
ggcaaacaaa ccaccgctgg tagcggtggt ttttttgttt gcaagcagca gattacgcgc   7200
agaaaaaaag gatctcaaga agatcctttg atcttttcta cggggtctga cgctcagtgg   7260
aacgaaaact cacgttaagg gattttggtc atgagattat caaaaaggat cttcacctag   7320
atccttttaa attaaaaatg aagttttaaa tcaatctaaa gtatatatga gtaaacttgg   7380
tctgacagtt accaatgctt aatcagtgag gcacctatct cagcgatctg tctatttcgt   7440
tcatccatag ttgcctgact ccccgtcgtg tagataacta cgatacggga gggcttacca   7500
tctggcccca gtgctgcaat gataccgcga gacccacgct caccggctcc agatttatca   7560
gcaataaacc agccagccgg aagggccgag cgcagaagtg gtcctgcaac tttatccgcc   7620
tccatccagt ctattaattg ttgccgggaa gctagagtaa gtagttcgcc agttaatagt   7680
ttgcgcaacg ttgttgccat tgctacaggc atcgtggtgt cacgctcgtc gtttggtatg   7740
gcttcattca gctccggttc ccaacgatca aggcgagtta catgatcccc catgttgtgc   7800
aaaaaagcgg ttagctcctt cggtcctccg atcgttgtca gaagtaagtt ggccgcagtg   7860
ttatcactca tggttatggc agcactgcat aattctctta ctgtcatgcc atccgtaaga   7920
tgcttttctg tgactggtga gtactcaacc aagtcattct gagaatagtg tatgcggcga   7980
ccgagttgct cttgcccggc gtcaatacgg gataataccg cgccacatag cagaacttta   8040
aaagtgctca tcattggaaa acgttcttcg gggcgaaaac tctcaaggat cttaccgctg   8100
ttgagatcca gttcgatgta acccactcgt gcacccaact gatcttcagc atcttttact   8160
ttcaccagcg tttctgggtg agcaaaaaca ggaaggcaaa atgccgcaaa aaagggaata   8220
agggcgacac ggaaatgttg aatactcata ctcttccttt ttcaatatta ttgaagcatt   8280
```

```
tatcagggtt attgtctcat gagcggatac atatttgaat gtatttagaa aaataaacaa   8340

ataggggttc cgcgcacatt tccccgaaaa gtgccacctg ggtccttttc atcacgtgct   8400

ataaaaataa ttataattta aatttttttaa tataaatata taaattaaaa atagaaagta   8460

aaaaaagaaa ttaaagaaaa aatagttttt gttttccgaa gatgtaaaag actctagggg   8520

gatcgccaac aaatactacc ttttatcttg ctcttcctgc tctcaggtat taatgccgaa   8580

ttgtttcatc ttgtctgtgt agaagaccac acacgaaaat cctgtgattt tacattttac   8640

ttatcgttaa tcgaatgtat atctatttaa tctgcttttc ttgtctaata aatatatatg   8700

taaagtacgc tttttgttga aatttttttaa acctttgttt atttttttttt cttcattccg   8760

taactcttct accttcttta tttactttct aaaatccaaa tacaaaacat aaaaataaat   8820

aaacacagag taaattccca aattattcca tcattaaaag atacgaggcg cgtgtaagtt   8880

acaggcaagc gatccgtcct aagaaaccat tattatcatg acattaacct ataaaaatag   8940

gcgtatcacg aggccctttc gtc                                           8963
```

<210> SEQ ID NO 10
<211> LENGTH: 7163
<212> TYPE: DNA
<213> ORGANISM: Artificial Sequence
<220> FEATURE:
<223> OTHER INFORMATION: Codon optimized

<400> SEQUENCE: 10

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct tttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600

agagaacaat tgacccggtt attgcaagga aaatttcaag tcttgtaaaa gcatataaaa    660

atagttcagg cactccgaaa tacttggttg gcgtgtttcg taatcaacct aaggaggatg    720

ttttggctct ggtcaatgat tacggcattg atatcgtcca actgcatgga gatgagtcgt    780

ggcaagaata ccaagagttc ctcggtttgc cagttattaa aagactcgta tttccaaaag    840

actgcaacat actactcagt gcagcttcac agaaacctca ttcgtttatt cccttgtttg    900

attcagaagc aggtgggaca ggtgaacttt tggattggaa ctcgatttct gactgggttg    960

gaaggcaaga gagccccgaa agcttacatt ttatgttagc tggtggactg acgccagaaa   1020

atgttggtga tgcgcttaga ttaaatggcg ttattggtgt tgatgtaagc ggaggtgtgg   1080

agacaaatgg tgtaaaagac tctaacaaaa tagcaaattt cgtcaaaaat gctaagaaat   1140

aggttattac tgagtagtat ttatttaagt attgtttgtg cacttgccta tgcggtgtga   1200

aataccgcac agatgcgtaa ggagaaaata ccgcatcagg aaattgtaaa cgttaatatt   1260

ttgttaaaat tcgcgttaaa tttttgttaa atcagctcat tttttaacca ataggccgaa   1320

atcggcaaaa tcccttataa atcaaaagaa tagaccgaga tagggttgag tgttgttcca   1380
```

```
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttatgca tagtctggaa catcgtaagg gtactttctt ggggtgtaat cgaagatcaa   2220
caatttttcc cagaaggatc tgtaaacgtc accaaaacca acgtgagctg gatgaatgat   2280
gtaatcttgg atagtttcaa ctgattcgaa ggttacttcg acaatgtgtg tataaccttc   2340
ttctttcttt tgtgtaacgt ctttacccca gtatacatct ttcatagcag gtataatgtt   2400
gaccaaatta acgtaggtct tgaaaaattc ttccttttga gcttctgtga tttcatcttt   2460
aaacttcaat actatcaaat gcttgacggc cataggacct gggttttctt caacgtcacc   2520
acaagttaac aaggaacctc taccttcata tttaattggt actgatctga caactactct   2580
ttcgacggtc aaaccaggac cgaaaccaaa taagacaccc cattcaaaac cgtcaccagt   2640
agtagattta ccctcttcta atgatctctt tctcaattca tccattacga acaagacagt   2700
ggatgaagac atgttaccgt gttcagataa aacatgtcta ctatctacaa acttttcttt   2760
cttcaaatcc aatttttctt caaccttatc caaaatggct ttaccacctg gatgtgttat   2820
ccagaaaata gagttccaat ctgagatacc tataggagtg aatgcttcta tcaaacactt   2880
ttctatgttg ttagagatta acattggaac gtctttgtgc aaatcgaaga tcaaacctgc   2940
ttctcttata tgaccaccaa ttgtaccttc agaattaggc aagatggttt gacctgtact   3000
gactaattca aatattggtc tttcaccaac agattcgtca ggttctgcac caacaataac   3060
agcagcagca ccgtcaccga agatagcttg accaactaac aattccaagt cagaatcact   3120
tggacctcta aacaagcaag ccataatgtc gcaacaaaca gctaatactc tggcaccctt   3180
gttgttttct gcaatatcct tagcgattct caaaacagta ccaccaccgt agcaacctaa   3240
ttgatacatc atgactctct taacggatgg tgacaaacct aacaatttgg cacagtggta   3300
gtctgcacca ggcatatctg tagtagatgc acttgtaaaa atcaaatgag tgatctttga   3360
ctttggttga ccccattcct taatggcttt tgcacaagca tctttaccca atttaggaac   3420
ttcgacaact aacatgtctt gtctggcatc caatgtttgc atttcgtgtt ctaccaatct   3480
tggattttgc ttcaaatgtt cttcgttcaa gaagcagttt ctctttctga tcatagactt   3540
atcacatatt tttctaaact tttccttcaa ttgagtcatg tgttcactct tggtaactct   3600
gaagtaataa tcaggaaatt catcttggat caatatgttt tctgggttgg ctgtacctat   3660
ggctaatacg gaggcaggac cttcggctct caaatggttc atactagttc tagatccgtc   3720
```

```
gaaactaagt tcttggtgtt ttaaaactaa aaaaaagact aactataaaa gtagaattta   3780
agaagtttaa gaaatagatt tacagaatta caatcaatac ctaccgtctt tatatactta   3840
ttagtcaagt aggggaataa tttcagggaa ctggtttaaa cctttttttt cagctttttc   3900
caaatcagag agagcagaag gtaatagaag gtgtaagaaa atgagataga tacatgcgtg   3960
ggtcaattgc cttgtgtcat catttactcc aggcaggttg catcactcca ttgaggttgt   4020
gcccgttttt tgcctgtttg tgccctgttc tctgtagttg cgctaagaga atggacctat   4080
gaactgatgg ttggtgaaga aaacaatatt ttggtgctgg gattcttttt ttttctggat   4140
gccagcttaa aaagcgggct ccattatatt tagtggatgc caggaataaa cctgttcacc   4200
caagcaccat cagtgttata tattctgtgt aacccgcccc ctattttggc atgtacgggt   4260
tacagcagaa ttaaaaggct aatttttga ctaaataaag ttaggaaaat cactactatt   4320
aattatttac gtattctttg aaatggcagt attgataatg ataaactcga gagctccagc   4380
ttttgttccc tttagtgagg gttaattgcg cgcttggcgt aatcatggtc atagctgttt   4440
cctgtgtgaa attgttatcc gctcacaatt ccacacaaca taggagccgg aagcataaag   4500
tgtaaagcct ggggtgccta atgagtgagg taactcacat taattgcgtt gcgctcactg   4560
cccgctttcc agtcgggaaa cctgtcgtgc cagctgcatt aatgaatcgg ccaacgcgcg   4620
gggagaggcg gtttgcgtat tgggcgctct tccgcttcct cgctcactga ctcgctgcgc   4680
tcggtcgttc ggctgcggcg agcggtatca gctcactcaa aggcggtaat acggttatcc   4740
acagaatcag gggataacgc aggaaagaac atgtgagcaa aaggccagca aaaggccagg   4800
aaccgtaaaa aggccgcgtt gctggcgttt ttccataggc tccgcccccc tgacgagcat   4860
cacaaaaatc gacgctcaag tcagaggtgg cgaaacccga caggactata aagataccag   4920
gcgtttcccc ctggaagctc cctcgtgcgc tctcctgttc cgaccctgcc gcttaccgga   4980
tacctgtccg cctttctccc ttcgggaagc gtggcgcttt ctcatagctc acgctgtagg   5040
tatctcagtt cggtgtaggt cgttcgctcc aagctgggct gtgtgcacga accccccgtt   5100
cagcccgacc gctgcgcctt atccggtaac tatcgtcttg agtccaaccc ggtaagacac   5160
gacttatcgc cactggcagc agccactggt aacaggatta gcagagcgag gtatgtaggc   5220
ggtgctacag agttcttgaa gtggtggcct aactacggct acactagaag gacagtattt   5280
ggtatctgcg ctctgctgaa gccagttacc ttcggaaaaa gagttggtag ctcttgatcc   5340
ggcaaacaaa ccaccgctgg tagcggtggt ttttttgttt gcaagcagca gattacgcgc   5400
agaaaaaaag gatctcaaga agatcctttg atcttttcta cggggtctga cgctcagtgg   5460
aacgaaaact cacgttaagg gattttggtc atgagattat caaaaaggat cttcacctag   5520
atccttttaa attaaaaatg aagttttaaa tcaatctaaa gtatatatga gtaaacttgg   5580
tctgacagtt accaatgctt aatcagtgag gcacctatct cagcgatctg tctatttcgt   5640
tcatccatag ttgcctgact ccccgtcgtg tagataacta cgatacggga gggcttacca   5700
tctggcccca gtgctgcaat gataccgcga gacccacgct caccggctcc agatttatca   5760
gcaataaacc agccagccgg aagggccgag cgcagaagtg gtcctgcaac tttatccgcc   5820
tccatccagt ctattaattg ttgccgggaa gctagagtaa gtagttcgcc agttaatagt   5880
ttgcgcaacg ttgttgccat tgctacaggc atcgtggtgt cacgctcgtc gtttggtatg   5940
gcttcattca gctccggttc ccaacgatca aggcgagtta catgatcccc catgttgtgc   6000
aaaaaagcgg ttagctcctt cggtcctccg atcgttgtca gaagtaagtt ggccgcagtg   6060
ttatcactca tggttatggc agcactgcat aattctctta ctgtcatgcc atccgtaaga   6120
```

```
tgcttttctg tgactggtga gtactcaacc aagtcattct gagaatagtg tatgcggcga   6180

ccgagttgct cttgcccggc gtcaatacgg gataataccg cgccacatag cagaacttta   6240

aaagtgctca tcattggaaa acgttcttcg gggcgaaaac tctcaaggat cttaccgctg   6300

ttgagatcca gttcgatgta acccactcgt gcacccaact gatcttcagc atcttttact   6360

ttcaccagcg tttctgggtg agcaaaaaca ggaaggcaaa atgccgcaaa aaagggaata   6420

agggcgacac ggaaatgttg aatactcata ctcttccttt ttcaatatta ttgaagcatt   6480

tatcagggtt attgtctcat gagcggatac atatttgaat gtatttagaa aaataaacaa   6540

ataggggttc cgcgcacatt tccccgaaaa gtgccacctg ggtccttttc atcacgtgct   6600

ataaaaataa ttataattta aatttttttaa tataaatata taaattaaaa atagaaagta   6660

aaaaaagaaa ttaaagaaaa aatagttttt gttttccgaa gatgtaaaag actctagggg   6720

gatcgccaac aaatactacc ttttatcttg ctcttcctgc tctcaggtat taatgccgaa   6780

ttgtttcatc ttgtctgtgt agaagaccac acacgaaaat cctgtgattt tacattttac   6840

ttatcgttaa tcgaatgtat atctatttaa tctgcttttc ttgtctaata aatatatatg   6900

taaagtacgc tttttgttga aatttttttaa acctttgttt attttttttt cttcattccg   6960

taactcttct accttcttta tttactttct aaaatccaaa tacaaaacat aaaaataaat   7020

aaacacagag taaattccca aattattcca tcattaaaag atacgaggcg cgtgtaagtt   7080

acaggcaagc gatccgtcct aagaaaccat tattatcatg acattaacct ataaaaatag   7140

gcgtatcacg aggccctttc gtc                                           7163
```

```
<210> SEQ ID NO 11
<211> LENGTH: 8710
<212> TYPE: DNA
<213> ORGANISM: Artificial Sequence
<220> FEATURE:
<223> OTHER INFORMATION: Codon optimized

<400> SEQUENCE: 11

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

tttttttttt cccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctactg gcgcgtggag    840

taaaaaggtt tggatcagga tttgcgcctt tggatgaggc actttccaga gcggtggtag    900

atctttcgaa caggccgtac gcagttgtcg aacttggttt gcaaagggag aaagtaggag    960
```

-continued

```
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
cctttttttct ttttgctttt tcttttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc atttttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa agggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cggccgcaaa ttaaagcctt   2100
cgagcgtccc aaaaccttct caagcaaggt tttcagtata atgttacatg cgtacacgcg   2160
tctgtacaga aaaaaaagaa aaatttgaaa tataaataac gttcttaata ctaacataac   2220
tataaaaaaa taaataggga cctagacttc aggttgtcta actccttcct tttcggttag   2280
agcggatgtg gggggagggc gtgaatgtaa gcgtgacata actaattaca tgactcgagg   2340
tcgacttaca aatcttcttc acttattaat ttttgttcgt gtctatgtct aggtaaaggt   2400
ggaatggatt gttcgtttct aaagaagttg tttgggtcaa ccaatgtctt aacctttact   2460
aatctatcga aatttttacc gaagtatttt tcaccccaaa ttctagcttg ggtatagttg   2520
ttaggattct ttggatcgtt aataccgatg tccaaatctc tgtagttcaa atatgccaat   2580
ctagggtttt tagaaacgta tggagtcatg aagttataga tgtttctaat ccagtttaag   2640
tgcttttcgt tatcttcttg cttttcccat gaacaaatgt accacaattc gtataagata   2700
ccagctctat gaggaaatgg aatggcagat tcactgattt cgtccattat accaccgtat   2760
ggatacaagg cgtacatgcc tgcaccaata tcttcttcgt acaatttttc taagatttgg   2820
acgaaaactg attcaggtat tggcttttta acgtagtcta acttaatttt aaaggcaccg   2880
ttttgacctg cggatctatc caataatatt tctttgttga agttgtctgt atcgtagttg   2940
acaacacctg aataaaagat gatggtgtcg atccaagaca attgtctaca atcagttttc   3000
ttaataccta attctggaaa agacttattc atcaagtcta ctaaggaatc gacaccaccc   3060
aagaaaactg aagaaaagta tgtgtggata gcagtcttat ttttaccttg gttatcggtg   3120
atgtttcttg tgatgaaatg agtcatcaac aacaagtcct tatcgtactt gtatgcgatg   3180
ttttgccact tattgaccaa tttaactaat tcatggattt ccattatctt tttgactgag   3240
aacatagtag actttggtac tgcgactaat cttatcttcc aagcaactat gataccgaat   3300
gattctgcac caccacctct caaagcccaa aataagtctt cacccataga ctttctatcc   3360
```

```
aaaactttac cgtgaacatt taccaaatga gcgtcgatta tgttatcagc ggccaaaccg   3420
tagtttctca ttaaaggacc ataaccacca ccaccaaaat gaccacctgc gcaaactgtt   3480
ggacagtaac cagcagccaa tgataagttt tcattctttt cgttaaccca gtagtatact   3540
tcacccaatg ttgcaccagc ttcaacccaa gcagtttgtg agtgtacgtc tattttaatt   3600
gatctcatgt ttctcaaatc aacgataacg aatggaactt gggagatgta tgacatgcct   3660
tcactatcat gaccaccgga tctagttcta atttgcaaac caaccttttt agaacataag   3720
atagtacctt ggatgtgaga tacatgacta ggggttacaa tgaccaaagg ttttggagtg   3780
gtatcagaag tgaatctcaa attatggatt gtactgttca agacggacat gtacaatggg   3840
ttgttttgag tgtaaaccaa cttcaaattg gtggcgttat taggtatgta ttgtgagaag   3900
cacttcaaaa agtttctct tgggtttgcg atacttgttt ggatgttaaa ggaaaagaaa   3960
aagaagatga tcttgcatac gaaccaaaag gagaaagttg aacatttcat aggacctgga   4020
ttttcttcaa cgtcaccaca ggtcaacaaa gaacctctac cttcaataaa aacgtatacc   4080
aaatattcag cgtagtacaa tttccacata aactcgtaga atcttctacc tgcttcaggg   4140
tcataatttg tcaaagcgaa atctctagtt tgcaagatca accagaaagc caagatggca   4200
tgtgacaaca acataacgtt agaattaaag gcttgtggcc aaatgatacc tgccaaaatg   4260
gctgcgacgt aacttaacaa aacgataccg gagcagaaca aagtcaaatt tcttgaaccg   4320
tacttagaag ccaaggtact aataccgaac tttgtgtcac cttcaacgtc agaggcatcc   4380
ttgatcaagg ctaatgcaga acccatactt ttcatgaatg ccaacaaaaa tgtgaatgaa   4440
ggtctcaatt cgaatggcaa acctaaagca gctcttgaag cgtagtagaa ggtgaagttt   4500
gtgatgatat gagctaagaa attcaacaaa aaggcagtac tagggttttg tttccatcta   4560
aaaggtggta cggaatagac aataccaccg aagataccga aacagtaacc gaagatgtac   4620
aatggaccac ccttcatttt aattgtgatg atcaaaccga acaaggctac tatgatagac   4680
atgatccatg cagtattgac ggatatttca cctgaagcca aaggcaaatc tggtttgtta   4740
attctgtcga tgtgcaaatc gtatatttga ttaattgtag tggtgaatga agcgatgcac   4800
aagatggcaa ctaaaaagaa aaatgccttg aacatcaagg accatgaaat taagttagtg   4860
ttatgcaaca attctttacc gaataaaccg catgcacaag aagtaaaagc gattatggtg   4920
tatggtcttt gcaacttcca acatgcttta ccgaagttca aaatttttgt ggcaacagag   4980
tgattatcac tttcaggtgg ttcagtttga tttgtagttg cagctctgat agagttctta   5040
gctatagaca aactttcgga gcacttattt tgtaagtgga aggacttggt tgaacaatgt   5100
tttgatggaa agttgttgta agagtactta ataggtgtct ttggatgtct gtaacacaac   5160
aatgatgttt ttggattgtt gttgtgagga ttcaataagg tatgatagtt agtttggaag   5220
gagaaagtac agacggatga taaacccata ctagttctag atccgtcgaa actaagttct   5280
tggtgtttta aaactaaaaa aaagactaac tataaaagta gaatttaaga agtttaagaa   5340
atagatttac agaattacaa tcaataccta ccgtctttat atacttatta gtcaagtagg   5400
ggaataattt cagggaactg gtttaaacct tttttttcag ctttttccaa atcagagaga   5460
gcagaaggta atagaaggtg taagaaaatg agatagatac atgcgtgggt caattgcctt   5520
gtgtcatcat ttactccagg caggttgcat cactccattg aggttgtgcc cgtttttttgc  5580
ctgtttgtgc cctgttctct gtagttgcgc taagagaatg gacctatgaa ctgatggttg   5640
gtgaagaaaa caatattttg gtgctgggat tctttttttt tctggatgcc agcttaaaaa   5700
```

```
gcgggctcca ttatatttag tggatgccag gaataaacct gttcacccaa gcaccatcag   5760

tgttatatat tctgtgtaac ccgcccccta ttttggcatg tacgggttac agcagaatta   5820

aaaggctaat tttttgacta aataaagtta ggaaaatcac tactattaat tatttacgta   5880

ttctttgaaa tggcagtatt gataatgata aactcgagag ctccagcttt tgttcccttt   5940

agtgagggtt aattgcgcgc ttggcgtaat catggtcata gctgtttcct gtgtgaaatt   6000

gttatccgct cacaattcca cacaacatag gagccggaag cataaagtgt aaagcctggg   6060

gtgcctaatg agtgaggtaa ctcacattaa ttgcgttgcg ctcactgccc gctttccagt   6120

cgggaaacct gtcgtgccag ctgcattaat gaatcggcca acgcgcgggg agaggcggtt   6180

tgcgtattgg gcgctcttcc gcttcctcgc tcactgactc gctgcgctcg gtcgttcggc   6240

tgcggcgagc ggtatcagct cactcaaagg cggtaatacg gttatccaca gaatcagggg   6300

ataacgcagg aaagaacatg tgagcaaaag gccagcaaaa ggccaggaac cgtaaaaagg   6360

ccgcgttgct ggcgtttttc cataggctcc gcccccctga cgagcatcac aaaaatcgac   6420

gctcaagtca gaggtggcga aacccgacag gactataaag ataccaggcg tttccccctg   6480

gaagctccct cgtgcgctct cctgttccga ccctgccgct taccggatac ctgtccgcct   6540

ttctcccttc gggaagcgtg gcgctttctc atagctcacg ctgtaggtat ctcagttcgg   6600

tgtaggtcgt tcgctccaag ctgggctgtg tgcacgaacc ccccgttcag cccgaccgct   6660

gcgccttatc cggtaactat cgtcttgagt ccaacccggt aagacacgac ttatcgccac   6720

tggcagcagc cactggtaac aggattagca gagcgaggta tgtaggcggt gctacagagt   6780

tcttgaagtg gtggcctaac tacggctaca ctagaaggac agtatttggt atctgcgctc   6840

tgctgaagcc agttaccttc ggaaaaagag ttggtagctc ttgatccggc aaacaaacca   6900

ccgctggtag cggtggtttt tttgtttgca agcagcagat tacgcgcaga aaaaaaggat   6960

ctcaagaaga tcctttgatc ttttctacgg ggtctgacgc tcagtggaac gaaaactcac   7020

gttaagggat tttggtcatg agattatcaa aaaggatctt cacctagatc cttttaaatt   7080

aaaaatgaag ttttaaatca atctaaagta tatatgagta aacttggtct gacagttacc   7140

aatgcttaat cagtgaggca cctatctcag cgatctgtct atttcgttca tccatagttg   7200

cctgactccc cgtcgtgtag ataactacga tacgggaggg cttaccatct ggccccagtg   7260

ctgcaatgat accgcgagac ccacgctcac cggctccaga tttatcagca ataaaccagc   7320

cagccggaag ggccgagcgc agaagtggtc ctgcaacttt atccgcctcc atccagtcta   7380

ttaattgttg ccgggaagct agagtaagta gttcgccagt taatagtttg cgcaacgttg   7440

ttgccattgc tacaggcatc gtggtgtcac gctcgtcgtt tggtatggct tcattcagct   7500

ccggttccca acgatcaagg cgagttacat gatcccccat gttgtgcaaa aaagcggtta   7560

gctccttcgg tcctccgatc gttgtcagaa gtaagttggc cgcagtgtta tcactcatgg   7620

ttatggcagc actgcataat tctcttactg tcatgccatc cgtaagatgc ttttctgtga   7680

ctggtgagta ctcaaccaag tcattctgag aatagtgtat gcggcgaccg agttgctctt   7740

gcccggcgtc aatacgggat aataccgcgc cacatagcag aactttaaaa gtgctcatca   7800

ttggaaaacg ttcttcgggg cgaaaactct caaggatctt accgctgttg agatccagtt   7860

cgatgtaacc cactcgtgca cccaactgat cttcagcatc ttttactttc accagcgttt   7920

ctgggtgagc aaaaacagga aggcaaaatg ccgcaaaaaa gggaataagg gcgacacgga   7980

aatgttgaat actcatactc ttcctttttc aatattattg aagcatttat cagggttatt   8040

gtctcatgag cggatacata tttgaatgta tttagaaaaa taaacaaata ggggttccgc   8100
```

```
gcacatttcc ccgaaaagtg ccacctgggt ccttttcatc acgtgctata aaaataatta   8160
taatttaaat tttttaatat aaatatataa attaaaaata gaaagtaaaa aaagaaatta   8220
aagaaaaaat agtttttgtt ttccgaagat gtaaaagact ctagggggat cgccaacaaa   8280
tactaccttt tatcttgctc ttcctgctct caggtattaa tgccgaattg tttcatcttg   8340
tctgtgtaga agaccacaca cgaaaatcct gtgattttac attttactta tcgttaatcg   8400
aatgtatatc tatttaatct gcttttcttg tctaataaat atatatgtaa agtacgcttt   8460
ttgttgaaat tttttaaacc tttgtttatt tttttttctt cattccgtaa ctcttctacc   8520
ttctttattt actttctaaa atccaaatac aaaacataaa aataaataaa cacagagtaa   8580
attcccaaat tattccatca ttaaaagata cgaggcgcgt gtaagttaca ggcaagcgat   8640
ccgtcctaag aaaccattat tatcatgaca ttaacctata aaaataggcg tatcacgagg   8700
ccctttcgtc                                                          8710
```

<210> SEQ ID NO 12
<211> LENGTH: 9617
<212> TYPE: DNA
<213> ORGANISM: Artificial Sequence
<220> FEATURE:
<223> OTHER INFORMATION: Codon optimized

<400> SEQUENCE: 12

```
ttatcatgac attaacctat aaaaataggc gtatcacgag gccctttcgt ctcgcgcgtt     60
tcggtgatga cggtgaaaac ctctgacaca tgcagctccc ggagacggtc acagcttgtc    120
tgtaagcgga tgccgggagc agacaagccc gtcagggcgc gtcagcgggt gttggcgggt    180
gtcggggctg gcttaactat gcggcatcag agcagattgt actgagagtg caccacgctt    240
ttcaattcaa ttcatcattt ttttttattc ttttttttg atttcggttt ctttgaaatt    300
tttttgattc ggtaatctcc gaacagaagg aagaacgaag gaaggagcac agacttagat    360
tggtatatat acgcatatgt agtgttgaag aaacatgaaa ttgcccagta ttcttaaccc    420
aactgcacag aacaaaaacc tgcaggaaac gaagataaat catgtcgaaa gctacatata    480
aggaacgtgc tgctactcat cctagtcctg ttgctgccaa gctatttaat atcatgcacg    540
aaaagcaaac aaacttgtgt gcttcattgg atgttcgtac caccaaggaa ttactggagt    600
tagttgaagc attaggtccc aaaatttgtt tactaaaaac acatgtggat atcttgactg    660
atttttccat ggagggcaca gttaagccgc taaaggcatt atccgccaag tacaattttt    720
tactcttcga agacagaaaa tttgctgaca ttggtaatac agtcaaattg cagtactctg    780
cgggtgtata cagaatagca gaatgggcag acattacgaa tgcacacggt gtggtgggcc    840
caggtattgt tagcggtttg aagcaggcgg cagaagaagt aacaaaggaa cctagaggcc    900
ttttgatgtt agcagaattg tcatgcaagg gctccctatc tactggagaa tatactaagg    960
gtactgttga cattgcgaag agcgacaaag attttgttat cggctttatt gctcaaagag   1020
acatgggtgg aagagatgaa ggttacgatt ggttgattat gacacccggt gtgggtttag   1080
atgacaaggg agacgcattg ggtcaacagt atagaaccgt ggatgatgtg gtctctacag   1140
gatctgacat tattattgtt ggaagaggac tatttgcaaa gggaagggat gctaaggtag   1200
agggtgaacg ttacagaaaa gcaggctggg aagcatattt gagaagatgc ggccagcaaa   1260
actaaaaaac tgtattataa gtaaatgcat gtatactaaa ctcacaaatt agagcttcaa   1320
tttaattata tcagttatta ccctgcggtg tgaaataccg cacagatgcg taaggagaaa   1380
```

```
ataccgcatc aggaaattgt aaacgttaat attttgttaa aattcgcgtt aaatttttgt   1440
taaatcagct cattttttaa ccaataggcc gaaatcggca aaatccctta taaatcaaaa   1500
gaatagaccg agatagggtt gagtgttgtt ccagtttgga acaagagtcc actattaaag   1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga aggggggatg tgctgcaagg cgattaagtt gggtaacgcc agggttttcc   1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
cgcactgctc cgaacaataa agattctaca atactagctt ttatggttat gaagaggaaa   2220
aattggcagt aacctggccc cacaaacctt caaattaacg aatcaaatta acaaccatag   2280
gatgataatg cgattagttt tttagcctta tttctggggt aattaatcag cgaagcgatg   2340
atttttgatc tattaacaga tatataaatg gaaaagctgc ataaccactt taactaatac   2400
tttcaacatt ttcagtttgt attacttctt attcaaatgt cataaaagta tcaacaaaaa   2460
attgttaata tacctctata ctttaacgtc aaggagaaaa aaccccggat tctagaacta   2520
gtggatcccc catcatgaac catttgagag ccgaaggtcc tgcctccgta ttagccatag   2580
gtacagccaa cccagaaaac atattgatcc aagatgaatt tcctgattat tacttcagag   2640
ttaccaagag tgaacacatg actcaattga aggaaaagtt tagaaaaata tgtgataagt   2700
ctatgatcag aaagagaaac tgcttcttga acgaagaaca tttgaagcaa aatccaagat   2760
tggtagaaca cgaaatgcaa acattggatg ccagacaaga catgttagtt gtcgaagttc   2820
ctaaattggg taaagatgct tgtgcaaaag ccattaagga atggggtcaa ccaaagtcaa   2880
agatcactca tttgattttt acaagtgcat ctactacaga tatgcctggt gcagactacc   2940
actgtgccaa attgttaggt ttgtcaccat ccgttaagag agtcatgatg tatcaattag   3000
gttgctacgg tggtggtact gttttgagaa tcgctaagga tattgcagaa aacaacaagg   3060
gtgccagagt attagctgtt tgttgcgaca ttatggcttg cttgtttaga ggtccaagtg   3120
attctgactt ggaattgtta gttggtcaag ctatcttcgg tgacggtgct gctgctgtta   3180
ttgttggtgc agaacctgac gaatctgttg gtgaaagacc aatatttgaa ttagtcagta   3240
caggtcaaac catcttgcct aattctgaag gtacaattgg tggtcatata agagaagcag   3300
gtttgatctt cgatttgcac aaagacgttc caatgttaat ctctaacaac atagaaaagt   3360
gtttgataga agcattcact cctataggta tctcagattg gaactctatt ttctggataa   3420
cacatccagg tggtaaagcc attttggata aggttgaaga aaaattggat ttgaagaaag   3480
aaaagtttgt agatagtaga catgttttat ctgaacacgg taacatgtct tcatccactg   3540
tcttgttcgt aatggatgaa ttgagaaaga gatcattaga agagggtaaa tctactactg   3600
gtgacggttt tgaatggggt gtcttatttg gtttcggtcc tggtttgacc gtcgaaagag   3660
tagttgtcag atcagtacca attaaatatg aaggtagagg ttccttgtta acttgtggtg   3720
acgttgaaga aaacccaggt cctatggccg tcaagcattt gatagtattg aagtttaaag   3780
```

```
atgaaatcac agaagctcaa aaggaagaat ttttcaagac ctacgttaat ttggtcaaca   3840
ttatacctgc tatgaaagat gtatactggg gtaaagacgt tacacaaaag aaagaagaag   3900
gttatacaca cattgtcgaa gtaaccttcg aatcagttga aactatccaa gattacatca   3960
ttcatccagc tcacgttggt tttggtgacg tttacagatc cttctgggaa aaattgttga   4020
tcttcgatta caccccaaga aagttaaagc caaaataatg ataacgagaa taatatcaag   4080
aataccttag aacaacatcg acaacaacaa caggcatttt cggatatgag tcacgtggag   4140
tattccagaa ttacaaaatt ttttcaagaa caaccactgg agggatatac ccttttctct   4200
cacaggtctg cgccatgggt ttatcatccg tctgtacttt ctccttccaa actaactatc   4260
ataccttatt gaatcctcac aacaacaatc caaaaacatc attgttgtgt tacagacatc   4320
caaagacacc tattaagtac tcttacaaca actttccatc aaaacattgt tcaaccaagt   4380
ccttccactt acaaaataag tgctccgaaa gtttgtctat agctaagaac tctatcagag   4440
ctgcaactac aaatcaaact gaaccacctg aaagtgataa tcactctgtt gccacaaaaa   4500
ttttgaactt cggtaaagca tgttggaagt tgcaaagacc atacaccata atcgctttta   4560
cttcttgtgc atgcggttta ttcggtaaag aattgttgca taacactaac ttaatttcat   4620
ggtccttgat gttcaaggca tttttctttt tagttgccat cttgtgcatc gcttcattca   4680
ccactacaat taatcaaata tacgatttgc acatcgacag aattaacaaa ccagatttgc   4740
ctttggcttc aggtgaaata tccgtcaata ctgcatggat catgtctatc atagtagcct   4800
tgttcggttt gatcatcaca attaaaatga agggtggtcc attgtacatc ttcggttact   4860
gtttcggtat cttcggtggt attgtctatt ccgtaccacc ttttagatgg aaacaaaacc   4920
ctagtactgc ctttttgttg aatttcttag ctcatatcat cacaaacttc accttctact   4980
acgcttcaag agctgcttta ggtttgccat tcgaattgag accttcattc acatttttgt   5040
tggcattcat gaaaagtatg ggttctgcat tagccttgat caaggatgcc tctgacgttg   5100
aaggtgacac aaagttcggt attagtacct tggcttctaa gtacggttca agaaatttga   5160
ctttgttctg ctccggtatc gttttgttaa gttacgtcgc agccattttg gcaggtatca   5220
tttggccaca agcctttaat tctaacgtta tgttgttgtc acatgccatc ttggctttct   5280
ggttgatctt gcaaactaga gatttcgctt tgacaaatta tgaccctgaa gcaggtagaa   5340
gattctacga gtttatgtgg aaattgtact acgctgaata tttggtatac gtttttattg   5400
aaggtagagg ttctttgttg acctgtggtg acgttgaaga aaatccaggt cctatgaaat   5460
gttcaacttt ctccttttgg ttcgtatgca agatcatctt ctttttcttt tcctttaaca   5520
tccaaacaag tatcgcaaac ccaagagaaa actttttgaa gtgcttctca caatacatac   5580
ctaataacgc caccaatttg aagttggttt acactcaaaa caacccattg tacatgtccg   5640
tcttgaacag tacaatccat aatttgagat tcacttctga taccactcca aaacctttgg   5700
tcattgtaac ccctagtcat gtatctcaca tccaaggtac tatcttatgt tctaaaaagg   5760
ttggtttgca aattagaact agatccggtg gtcatgatag tgaaggcatg tcatacatct   5820
cccaagttcc attcgttatc gttgatttga gaaacatgag atcaattaaa atagacgtac   5880
actcacaaac tgcttgggtt gaagctggtg caacattggg tgaagtatac tactgggtta   5940
acgaaaagaa tgaaaactta tcattggctg ctggttactg tccaacagtt tgcgcaggtg   6000
gtcattttgg tggtggtggt tatggtcctt taatgagaaa ctacggtttg gccgctgata   6060
acataatcga cgctcatttg gtaaatgttc acggtaaagt tttggataga aagtctatgg   6120
```

```
gtgaagactt attttgggct ttgagaggtg gtggtgcaga atcattcggt atcatagttg   6180
cttggaagat aagattagtc gcagtaccaa agtctactat gttctcagtc aaaaagataa   6240
tggaaatcca tgaattagtt aaattggtca ataagtggca aaacatcgca tacaagtacg   6300
ataaggactt gttgttgatg actcatttca tcacaagaaa catcaccgat aaccaaggta   6360
aaaataagac tgctatccac acatactttt cttcagtttt cttgggtggt gtcgattcct   6420
tagtagactt gatgaataag tcttttccag aattaggtat taagaaaact gattgtagac   6480
aattgtcttg gatcgacacc atcatctttt attcaggtgt tgtcaactac gatacagaca   6540
acttcaacaa agaaatatta ttggatagat ccgcaggtca aaacggtgcc tttaaaatta   6600
agttagacta cgttaaaaag ccaatacctg aatcagtttt cgtccaaatc ttagaaaaat   6660
tgtacgaaga agatattggt gcaggcatgt acgccttgta tccatacggt ggtataatgg   6720
acgaaatcag tgaatctgcc attccatttc ctcatagagc tggtatctta tacgaattgt   6780
ggtacatttg ttcatgggaa aagcaagaag ataacgaaaa gcacttaaac tggattagaa   6840
acatctataa cttcatgact ccatacgttt ctaaaaaccc tagattggca tatttgaact   6900
acagagattt ggacatcggt attaacgatc caaagaatcc taacaactat acccaagcta   6960
gaatttgggg tgaaaaatac ttcggtaaaa atttcgatag attagtaaag gttaagacat   7020
tggttgaccc aaacaacttc tttagaaacg aacaatccat tccaccttta cctagacata   7080
gacactgatg ggctgcagga attcgatatc aagcttatcg ataccgtcga cctcgagtca   7140
tgtaattagt tatgtcacgc ttacattcac gccctccccc cacatccgct ctaaccgaaa   7200
aggaaggagt tagacaacct gaagtctagg tccctattta tttttttata gttatgttag   7260
tattaagaac gttatttata tttcaaattt ttcttttttt tctgtacaga cgcgtgtacg   7320
catgtaacat tatactgaaa accttgcttg agaaggtttt gggacgctcg aaggctttaa   7380
tttgcggccg gtacccagct tttgttccct ttagtgaggg ttaattccga gcttggcgta   7440
atcatggtca tagctgtttc ctgtgtgaaa ttgttatccg ctcacaattc cacacaacat   7500
aggagccgga agcataaagt gtaaagcctg gggtgcctaa tgagtgaggt aactcacatt   7560
aattgcgttg cgctcactgc ccgctttcca gtcgggaaac ctgtcgtgcc agctgcatta   7620
atgaatcggc caacgcgcgg ggagaggcgg tttgcgtatt gggcgctctt ccgcttcctc   7680
gctcactgac tcgctgcgct cggtcgttcg gctgcggcga gcggtatcag ctcactcaaa   7740
ggcggtaata cggttatcca cagaatcagg ggataacgca ggaaagaaca tgtgagcaaa   7800
aggccagcaa aaggccagga accgtaaaaa ggccgcgttg ctggcgtttt tccataggct   7860
ccgcccccct gacgagcatc acaaaaatcg acgctcaagt cagaggtggc gaaacccgac   7920
aggactataa agataccagg cgtttccccc tggaagctcc ctcgtgcgct ctcctgttcc   7980
gaccctgccg cttaccggat acctgtccgc ctttctccct tcgggaagcg tggcgctttc   8040
tcaatgctca cgctgtaggt atctcagttc ggtgtaggtc gttcgctcca agctgggctg   8100
tgtgcacgaa ccccccgttc agcccgaccg ctgcgcctta tccggtaact atcgtcttga   8160
gtccaacccg gtaagacacg acttatcgcc actggcagca gccactggta acaggattag   8220
cagagcgagg tatgtaggcg gtgctacaga gttcttgaag tggtggccta actacggcta   8280
cactagaagg acagtatttg gtatctgcgc tctgctgaag ccagttacct tcggaaaaag   8340
agttggtagc tcttgatccg gcaaacaaac caccgctggt agcggtggtt tttttgtttg   8400
caagcagcag attacgcgca gaaaaaaagg atctcaagaa gatcctttga tcttttctac   8460
ggggtctgac gctcagtgga acgaaaactc acgttaaggg attttggtca tgagattatc   8520
```

```
aaaaaggatc ttcacctaga tccttttaaa ttaaaaatga agttttaaat caatctaaag   8580

tatatatgag taaacttggt ctgacagtta ccaatgctta atcagtgagg cacctatctc   8640

agcgatctgt ctatttcgtt catccatagt tgcctgactg cccgtcgtgt agataactac   8700

gatacgggag ggcttaccat ctggccccag tgctgcaatg ataccgcgag acccacgctc   8760

accggctcca gatttatcag caataaacca gccagccgga agggccgagc gcagaagtgg   8820

tcctgcaact ttatccgcct ccatccagtc tattaattgt tgccgggaag ctagagtaag   8880

tagttcgcca gttaatagtt tgcgcaacgt tgttgccatt gctacaggca tcgtggtgtc   8940

acgctcgtcg tttggtatgg cttcattcag ctccggttcc caacgatcaa ggcgagttac   9000

atgatccccc atgttgtgaa aaaaagcggt tagctccttc ggtcctccga tcgttgtcag   9060

aagtaagttg gccgcagtgt tatcactcat ggttatggca gcactgcata attctcttac   9120

tgtcatgcca tccgtaagat gcttttctgt gactggtgag tactcaacca agtcattctg   9180

agaatagtgt atgcggcgac cgagttgctc ttgcccggcg tcaatacggg ataataccgc   9240

gccacatagc agaactttaa aagtgctcat cattggaaaa cgttcttcgg ggcgaaaact   9300

ctcaaggatc ttaccgctgt tgagatccag ttcgatgtaa cccactcgtg cacccaactg   9360

atcttcagca tcttttactt tcaccagcgt ttctgggtga gcaaaaacag gaaggcaaaa   9420

tgccgcaaaa aagggaataa gggcgacacg gaaatgttga atactcatac tcttcctttt   9480

tcaatattat tgaagcattt atcagggtta ttgtctcatg agcggataca tatttgaatg   9540

tatttagaaa aataaacaaa taggggttcc gcgcacattt ccccgaaaag tgccacctga   9600

cgtctaagaa accatta                                                  9617
```

<210> SEQ ID NO 13
<211> LENGTH: 7879
<212> TYPE: DNA
<213> ORGANISM: Artificial Sequence
<220> FEATURE:
<223> OTHER INFORMATION: Codon optimized

<400> SEQUENCE: 13

```
aacctataaa aataggcgta tcacgaggcc ctttcgtctc gcgcgtttcg gtgatgacgg     60

tgaaaacctc tgacacatgc agctcccgga gacggtcaca gcttgtctgt aagcggatgc    120

cgggagcaga caagcccgtc agggcgcgtc agcgggtgtt ggcgggtgtc ggggctggct    180

taactatgcg gcatcagagc agattgtact gagagtgcac cacgcttttc aattcaattc    240

atcatttttt ttttattctt ttttttgatt tcggtttctt tgaaattttt ttgattcggt    300

aatctccgaa cagaaggaag aacgaaggaa ggagcacaga cttagattgg tatatatacg    360

catatgtagt gttgaagaaa catgaaattg cccagtattc ttaacccaac tgcacagaac    420

aaaaacctgc aggaaacgaa gataaatcat gtcgaaagct acatataagg aacgtgctgc    480

tactcatcct agtcctgttg ctgccaagct atttaatatc atgcacgaaa agcaaacaaa    540

cttgtgtgct tcattggatg ttcgtaccac caaggaatta ctggagttag ttgaagcatt    600

aggtcccaaa atttgtttac taaaaacaca tgtggatatc ttgactgatt tttccatgga    660

gggcacagtt aagccgctaa aggcattatc cgccaagtac aatttttac tcttcgaaga    720

cagaaaattt gctgacattg gtaatacagt caaattgcag tactctgcgg gtgtatacag    780

aatagcagaa tgggcagaca ttacgaatgc acacggtgtg gtgggcccag gtattgttag    840

cggtttgaag caggcggcag aagaagtaac aaaggaacct agaggccttt tgatgttagc    900
```

```
agaattgtca tgcaagggct ccctatctac tggagaatat actaagggta ctgttgacat    960
tgcgaagagc gacaaagatt ttgttatcgg ctttattgct caaagagaca tgggtggaag   1020
agatgaaggt tacgattggt tgattatgac acccggtgtg ggtttagatg acaagggaga   1080
cgcattgggt caacagtata gaaccgtgga tgatgtggtc tctacaggat ctgacattat   1140
tattgttgga agaggactat ttgcaaaggg aagggatgct aaggtagagg gtgaacgtta   1200
cagaaaagca ggctgggaag catatttgag aagatgcggc cagcaaaact aaaaaactgt   1260
attataagta aatgcatgta tactaaactc acaaattaga gcttcaattt aattatatca   1320
gttattaccc tgcggtgtga aataccgcac agatgcgtaa ggagaaaata ccgcatcagg   1380
aaattgtaaa cgttaatatt ttgttaaaat tcgcgttaaa tttttgttaa atcagctcat   1440
tttttaacca ataggccgaa atcggcaaaa tcccttataa atcaaaagaa tagaccgaga   1500
tagggttgag tgttgttcca gtttggaaca agagtccact attaaagaac gtggactcca   1560
acgtcaaagg gcgaaaaacc gtctatcagg gcgatggccc actacgtgaa ccatcaccct   1620
aatcaagttt tttggggtcg aggtgccgta aagcactaaa tcggaaccct aaagggagcc   1680
cccgatttag agcttgacgg ggaaagccgg cgaacgtggc gagaaaggaa gggaagaaag   1740
cgaaaggagc gggcgctagg gcgctggcaa gtgtagcggt cacgctgcgc gtaaccacca   1800
cacccgccgc gcttaatgcg ccgctacagg gcgcgtcgcg ccattcgcca ttcaggctgc   1860
gcaactgttg ggaagggcga tcggtgcggg cctcttcgct attacgccag ctggcgaagg   1920
ggggatgtgc tgcaaggcga ttaagttggg taacgccagg gttttcccag tcacgacgtt   1980
gtaaaacgac ggccagtgaa ttgtaatacg actcactata gggcgaattg gagctctagt   2040
acggattaga agccgccgag cgggcgacag ccctccgacg gaagactctc ctccgtgcgt   2100
cctcgtcttc accggtcgcg ttcctgaaac gcagatgtgc ctcgcgccgc actgctccga   2160
acaataaaga ttctacaata ctagctttta tggttatgaa gaggaaaaat tggcagtaac   2220
ctggccccac aaaccttcaa attaacgaat caaattaaca accataggat gataatgcga   2280
ttagtttttt agccttattt ctggggtaat taatcagcga agcgatgatt tttgatctat   2340
taacagatat ataaatggaa aagctgcata accactttaa ctaatacttt caacattttc   2400
agtttgtatt acttcttatt caaatgtcat aaaagtatca acaaaaaatt gttaatatac   2460
ctctatactt taacgtcaag gagaaaaaac cccggattct agaactagtg gatcatgaac   2520
catttgagag ccgaaggtcc tgcctccgta ttagccatag gtacagccaa cccagaaaac   2580
atattgatcc aagatgaatt tcctgattat tacttcagag ttaccaagag tgaacacatg   2640
actcaattga aggaaaagtt tagaaaaata tgtgataagt ctatgatcag aaagagaaac   2700
tgcttcttga acgaagaaca tttgaagcaa aatccaagat tggtagaaca cgaaatgcaa   2760
acattggatg ccagacaaga catgttagtt gtcgaagttc ctaaattggg taaagatgct   2820
tgtgcaaaag ccattaagga atggggtcaa ccaaagtcaa agatcactca tttgattttt   2880
acaagtgcat ctactacaga tatgcctggt gcagactacc actgtgccaa attgttaggt   2940
ttgtcaccat ccgttaagag agtcatgatg tatcaattag gttgctacgg tggtggtact   3000
gttttgagaa tcgctaagga tattgcagaa aacaacaagg gtgccagagt attagctgtt   3060
tgttgcgaca ttatggcttg cttgtttaga ggtccaagtg attctgactt ggaattgtta   3120
gttggtcaag ctatcttcgg tgacggtgct gctgctgtta ttgttggtgc agaacctgac   3180
gaatctgttg gtgaaagacc aatatttgaa ttagtcagta caggtcaaac catcttgcct   3240
aattctgaag gtacaattgg tggtcatata agagaagcag gtttgatctt cgatttgcac   3300
```

-continued aaagacgttc caatgttaat ctctaacaac atagaaaagt gtttgataga agcattcact 3360
cctataggta tctcagattg gaactctatt ttctggataa cacatccagg tggtaaagcc 3420
attttggata aggttgaaga aaaattggat ttgaagaaag aaaagtttgt agatagtaga 3480
catgttttat ctgaacacgg taacatgtct tcatccactg tcttgttcgt aatggatgaa 3540
ttgagaaaga gatcattaga agagggtaaa tctactactg gtgacggttt tgaatggggt 3600
gtcttatttg gtttcggtcc tggtttgacc gtcgaaagag tagttgtcag atcagtacca 3660
attaaatatg aaggtagagg ttccttgtta acttgtggtg acgttgaaga aaacccaggt 3720
cctatggccg tcaagcattt gatagtattg aagtttaaag atgaaatcac agaagctcaa 3780
aaggaagaat ttttcaagac ctacgttaat ttggtcaaca ttatacctgc tatgaaagat 3840
gtatactggg gtaaagacgt tacacaaaag aaagaagaag gttatacaca cattgtcgaa 3900
gtaaccttcg aatcagttga aactatccaa gattacatca ttcatccagc tcacgttggt 3960
tttggtgacg tttacagatc cttctgggaa aaattgttga tcttcgatta caccccaaga 4020
aagtgataac gagaataata tcaagaatac cttagaacaa catcgacaac aacaacaggc 4080
attttcggat atgagtcacg tggagtattc cagaattaca aaattttttc aagaacaacc 4140
actggaggga tataccettt tctctcacag gtctgcgcca tgggtttatc atccgtctgt 4200
actttctcct tccaaactaa ctatcatacc ttattgaatc ctcacaacaa caatccaaaa 4260
acatcattgt tgtgttacag acatccaaag acacctatta agtactctta caacaacttt 4320
ccatcaaaac attgttcaac caagtccttc cacttacaaa ataagtgctc cgaaagtttg 4380
tctatagcta agaactctat cagagctgca actacaaatc aaactgaacc acctgaaagt 4440
gataatcact ctgttgccac aaaaattttg aacttcggta aagcatgttg gaagttgcaa 4500
agaccataca ccataatcgc ttttacttct tgtgcatgcg gtttattcgg taaagaattg 4560
ttgcataaca ctaacttaat ttcatggtcc ttgatgttca aggcattttt ctttttagtt 4620
gccatcttgt gcatcgcttc attcaccact acaattaatc aaatatacga tttgcacatc 4680
gacagaatta acaaaccaga tttgcctttg gcttcaggtg aaatatccgt caatactgca 4740
tggatcatgt ctatcatagt agccttgttc ggtttgatca tcacaattaa aatgaagggt 4800
ggtccattgt acatcttcgg ttactgtttc ggtatcttcg gtggtattgt ctattccgta 4860
ccacctttta gatggaaaca aaaccctagt actgcctttt tgttgaattt cttagctcat 4920
atcatcacaa acttcacctt ctactacgct tcaagagctg ctttaggttt gccattcgaa 4980
ttgagacctt cattcacatt tttgttggca ttcatgaaaa gtatgggttc tgcattagcc 5040
ttgatcaagg atgcctctga cgttgaaggt gacacaaagt tcggtattag taccttggct 5100
tctaagtacg gttcaagaaa tttgactttg ttctgctccg gtatcgtttt gttaagttac 5160
gtcgcagcca ttttggcagg tatcatttgg ccacaagcct ttaattctaa cgttatgttg 5220
ttgtcacatg ccatcttggc tttctggttg atcttgcaaa ctagagattt cgctttgaca 5280
aattatgacc ctgaagcagg tagaagattc tacgagttta tgtggaaatt gtactacgct 5340
gaatatttgg tatacgtttt tatttaacga taccgtcgac ctcgagtcat gtaattagtt 5400
atgtcacgct tacattcacg ccctccccc acatccgctc taaccgaaaa ggaaggagtt 5460
agacaacctg aagtctaggt ccctatttat ttttttatag ttatgttagt attaagaacg 5520
ttatttatat ttcaaatttt tctttttttt ctgtacagac gcgtgtacgc atgtaacatt 5580
atactgaaaa ccttgcttga gaaggttttg ggacgctcga aggctttaat ttgcggccgg 5640

```
tacccagctt ttgttccctt tagtgagggt taattccgag cttggcgtaa tcatggtcat   5700
agctgtttcc tgtgtgaaat tgttatccgc tcacaattcc acacaacata ggagccggaa   5760
gcataaagtg taaagcctgg ggtgcctaat gagtgaggta actcacatta attgcgttgc   5820
gctcactgcc cgctttccag tcgggaaacc tgtcgtgcca gctgcattaa tgaatcggcc   5880
aacgcgcggg gagaggcggt ttgcgtattg ggcgctcttc cgcttcctcg ctcactgact   5940
cgctgcgctc ggtcgttcgg ctgcggcgag cggtatcagc tcactcaaag gcggtaatac   6000
ggttatccac agaatcaggg gataacgcag gaaagaacat gtgagcaaaa ggccagcaaa   6060
aggccaggaa ccgtaaaaag gccgcgttgc tggcgttttt ccataggctc ggcccccctg   6120
acgagcatca caaaaatcga cgctcaagtc agaggtggcg aaacccgaca ggactataaa   6180
gataccaggc gttcccccct ggaagctccc tcgtgcgctc tcctgttccg accctgccgc   6240
ttaccggata cctgtccgcc tttctccctt cgggaagcgt ggcgctttct caatgctcac   6300
gctgtaggta tctcagttcg gtgtaggtcg ttcgctccaa gctgggctgt gtgcacgaac   6360
cccccgttca gcccgaccgc tgcgccttat ccggtaacta tcgtcttgag tccaacccgg   6420
taagacacga cttatcgcca ctggcagcag ccactggtaa caggattagc agagcgaggt   6480
atgtaggcgg tgctacagag ttcttgaagt ggtggcctaa ctacggctac actagaagga   6540
cagtatttgg tatctgcgct ctgctgaagc cagttacctt cggaaaaaga gttggtagct   6600
cttgatccgg caaacaaacc accgctggta gcggtggttt ttttgtttgc aagcagcaga   6660
ttacgcgcag aaaaaaagga tctcaagaag atcctttgat cttttctacg gggtctgacg   6720
ctcagtggaa cgaaaactca cgttaaggga ttttggtcat gagattatca aaaaggatct   6780
tcacctagat ccttttaaat taaaaatgaa gttttaaatc aatctaaagt atatatgagt   6840
aaacttggtc tgacagttac caatgcttaa tcagtgaggc acctatctca gcgatctgtc   6900
tatttcgttc atccatagtt gcctgactgc ccgtcgtgta gataactacg atacgggagg   6960
gcttaccatc tggccccagt gctgcaatga taccgcgaga cccacgctca ccggctccag   7020
atttatcagc aataaaccag ccagccggaa gggccgagcg cagaagtggt cctgcaactt   7080
tatccgcctc catccagtct attaattgtt gccgggaagc tagagtaagt agttcgccag   7140
ttaatagttt gcgcaacgtt gttgccattg ctacaggcat cgtggtgtca cgctcgtcgt   7200
ttggtatggc ttcattcagc tccggttccc aacgatcaag gcgagttaca tgatccccca   7260
tgttgtgaaa aaaagcggtt agctccttcg gtcctccgat cgttgtcaga agtaagttgg   7320
ccgcagtgtt atcactcatg gttatggcag cactgcataa ttctcttact gtcatgccat   7380
ccgtaagatg cttttctgtg actggtgagt actcaaccaa gtcattctga gaatagtgta   7440
tgcggcgacc gagttgctct tgcccggcgt caatacggga taataccgcg ccacatagca   7500
gaactttaaa agtgctcatc attggaaaac gttcttcggg gcgaaaactc tcaaggatct   7560
taccgctgtt gagatccagt tcgatgtaac ccactcgtgc acccaactga tcttcagcat   7620
cttttacttt caccagcgtt tctgggtgag caaaaacagg aaggcaaaat gccgcaaaaa   7680
agggaataag ggcgacacgg aaatgttgaa tactcatact cttccttttt caatattatt   7740
gaagcattta tcagggttat tgtctcatga gcggatacat atttgaatgt atttagaaaa   7800
ataaacaaat aggggttccg cgcacatttc cccgaaaagt gccacctgac gtctaagaaa   7860
ccattattat catgacatt                                                 7879
```

<210> SEQ ID NO 14
<211> LENGTH: 3353

```
<212> TYPE: DNA
<213> ORGANISM: Artificial Sequence
<220> FEATURE:
<223> OTHER INFORMATION: Codon optimized

<400> SEQUENCE: 14

actagtatgg gtaaaaacta taagtccttg gattcagtcg ttgcctcaga tttcatcgca     60

ttgggtatca cctcagaagt agcagaaaca ttacatggta gattggcaga aatcgtttgt    120

aattatggtg ctgcaacccc tcaaacttgg atcaacatcg ctaaccatat cttgtcacca    180

gatttgcctt tctccttaca ccaaatgttg ttttatggtt gctacaagga tttcggtcca    240

gccccacctg cttggattcc agaccctgaa aaagtcaagt caactaattt gggtgctttg    300

ttggaaaaga gaggtaaaga atttttgggt gtaaagtaca aagatccaat ttcttctttt    360

tctcacttcc aagaattttc tgttagaaac cctgaagtct attggagaac agtattgatg    420

gatgaaatga aaattagttt ctctaaggac ccagaatgta tcttgagaag agatgacatc    480

aacaacccag gtggttctga atggttacct ggtggttact tgaactcagc taaaaattgc    540

ttgaacgtaa actccaataa gaaattgaac gatactatga tcgtttggag agacgagggt    600

aacgatgact tgcctttgaa taagttgaca ttagatcaat tgagaaagag agtttggttg    660

gttggttatg cattggaaga aatgggttta gaaaaaggtt gtgcaatagc catcgatatg    720

ccaatgcatg ttgatgctgt tgttatatat ttggccatag tattggctgg ttacgtagtt    780

gtctctatag cagattcatt ttccgcccct gaaatctcaa ctagattgag attatccaaa    840

gctaaggcaa ttttcacaca agatcacatc atcagaggta aaaagagaat accattgtat    900

tcaagagtag ttgaagctaa atccccaatg gcaatagtta tcccttgtag tggttctaac    960

attggtgcag aattgagaga tggtgacata tcttgggatt actttttaga aagagccaag   1020

gagtttaaaa actgcgagtt tactgccaga gaacaacctg ttgatgctta tactaacatc   1080

ttattctcca gtggtactac aggtgaacca aaagcaattc cttggacaca agccacccca   1140

ttgaaggctg ctgctgatgg ttggtctcat ttggatatta gaaaaggtga cgttatagta   1200

tggccaacta atttgggttg gatgatgggt ccttggttgg tttatgctag tttgttaaat   1260

ggtgcatcta ttgccttgta caacggtagt cctttagtct ctggtttcgc taaatttgtt   1320

caagatgcaa aggtcacaat gttgggtgtc gtaccatcta ttgtaagatc atggaaatcc   1380

acaaattgtg tttcaggtta cgattggtcc accataagat gcttttcttc atccggtgaa   1440

gcctctaatg tagacgaata tttgtggtta atgggtagag ctaactacaa gccagttata   1500

gaaatgtgtg gtggtacaga aatcggtggt gctttttctg ctggttcatt tttgcaagct   1560

caatctttaa gttctttttc atcccaatgt atgggttgca ccttgtacat attagataag   1620

aacggttacc caatgcctaa aaataagcca ggtatcggtg aattggcatt aggtcctgtt   1680

atgtttggtg cctcaaaaac attgttaaac ggtaatcatc acgatgtcta tttcaagggt   1740

atgccaacct tgaatggtga agtattgaga agacatggtg acattttcga attgacctct   1800

aacggttact accatgcaca cggtagagcc gatgacacta tgaacatcgg tggtatcaaa   1860

attagttcta tcgaaatcga aagagtctgt aatgaagtag atgacagagt tttttgaaacc   1920

actgctattg gtgttccacc tttgggtggt ggtccagaac aattggtcat atttttcgta   1980

ttgaaggatt caaacgacac aaccattgat ttgaaccaat tgagattatc ctttaacttg   2040

ggtttgcaaa agaaattgaa cccattattc aaagttacta gagttgtccc attgtcatcc   2100

ttacctagaa ctgcaacaaa caagatcatg agaagagttt tgagacaaca attcagtcat   2160
```

```
ttcgaagaag gtagaggttc tttgttaaca tgtggtgacg ttgaagaaaa tccaggtcct   2220
atggcttcag aaaaggaaat aagaagagaa agattcttga acgtattccc aaagttagtt   2280
gaagaattga acgctagttt gttagcttat ggtatgccta aagaagcctg cgattggtat   2340
gctcactctt taaactacaa tactccaggt ggtaaattga atagaggttt gagtgtagtt   2400
gatacttatg ctatcttgtc taacaaaacc gttgaacaat taggtcaaga agaatacgaa   2460
aaggtcgcta tcttgggttg gtgtattgaa ttgttgcaag catacttttt ggttgccgat   2520
gacatgatgg ataagtctat aacaagaaga ggtcaaccat gctggtacaa agttccagaa   2580
gttggtgaaa tagccataaa tgatgctttt atgttggaag ccgctatcta taaattgttg   2640
aagtcacatt tcagaaacga aaagtactac atcgatatta ccgaattatt ccacgaagtt   2700
actttccaaa cagaattggg tcaattgatg gatttgataa ctgcacctga agataaagtt   2760
gacttgtcaa agttttcctt gaagaaacat tcattcatcg tcacctttga aactgcttat   2820
tactccttct atttgccagt cgccttggct atgtacgtag ctggtattac tgatgaaaaa   2880
gacttgaagc aagcaagaga tgttttgata cctttgggtg aatacttcca aatccaagat   2940
gactacttag actgtttcgg tactccagaa caaataggta aaatcggtac agatattcaa   3000
gacaataagt gcagttgggt tattaacaag gctttggaat tagcatctgc cgaacaaaga   3060
aagactttgg atgaaaacta cggtaaaaag gactcagttg ctgaagcaaa gtgtaagaaa   3120
atttttaatg atttgaagat tgaacaattg taccatgaat acgaagaatc catcgctaaa   3180
gacttaaagg caaagattag tcaagttgat gaatcaagag gttttaaagc cgacgttttg   3240
acagctttct tgaataaggt ctacaagaga tcaaaggatt acaaggatca tgacggtgac   3300
tataaagacc acgatattga ctacaaagat gacgatgaca agtaagcggc cgc          3353
```

<210> SEQ ID NO 15
<211> LENGTH: 1553
<212> TYPE: DNA
<213> ORGANISM: Artificial Sequence
<220> FEATURE:
<223> OTHER INFORMATION: Codon optimized

<400> SEQUENCE: 15

```
actagtatga accatttgag agccgaaggt cctgcctccg tattagccat aggtacagcc     60
aacccagaaa acatattgat ccaagatgaa tttcctgatt attacttcag agttaccaag    120
agtgaacaca tgactcaatt gaaggaaaag tttagaaaaa tatgtgataa gtctatgatc    180
agaaagagaa actgcttctt gaacgaagaa catttgaagc aaaatccaag attggtagaa    240
cacgaaatgc aaacattgga tgccagacaa gacatgttag ttgtcgaagt tcctaaattg    300
ggtaaagatg cttgtgcaaa agccattaag gaatggggtc aaccaaagtc aaagatcact    360
catttgattt ttacaagtgc atctactaca gatatgcctg gtgcagacta ccactgtgcc    420
aaattgttag gtttgtcacc atccgttaag agagtcatga tgtatcaatt aggttgctac    480
ggtggtggta ctgttttgag aatcgctaag gatattgcag aaaacaacaa gggtgccaga    540
gtattagctg tttgttgcga cattatggct tgcttgttta gaggtccaag tgattctgac    600
ttggaattgt tagttggtca agctatcttc ggtgacggtg ctgctgctgt tattgttggt    660
gcagaacctg acgaatctgt tggtgaaaga ccaatatttg aattagtcag tacaggtcaa    720
accatcttgc ctaattctga aggtacaatt ggtggtcata taagagaagc aggtttgatc    780
ttcgatttgc acaaagacgt tccaatgtta atctctaaca acatagaaaa gtgtttgata    840
gaagcattca ctcctatagg tatctcagat tggaactcta ttttctggat aacacatcca    900
```

ggtggtaaag ccattttgga taaggttgaa gaaaaattgg atttgaagaa agaaaagttt 960
gtagatagta gacatgtttt atctgaacac ggtaacatgt cttcatccac tgtcttgttc 1020
gtaatggatg aattgagaaa gagatcatta gaagagggta aatctactac tggtgacggt 1080
tttgaatggg gtgtcttatt tggtttcggt cctggtttga ccgtcgaaag agtagttgtc 1140
agatcagtac caattaaata tgaaggtaga ggttccttgt taacttgtgg tgacgttgaa 1200
gaaaacccag gtcctatggc cgtcaagcat ttgatagtat tgaagtttaa agatgaaatc 1260
acagaagctc aaaaggaaga atttttcaag acctacgtta atttggtcaa cattatacct 1320
gctatgaaag atgtatactg ggtaaagac gttacacaaa agaaagaaga aggttataca 1380
cacattgtcg aagtaacctt cgaatcagtt gaaactatcc aagattacat cattcatcca 1440
gctcacgttg gttttggtga cgtttacaga tccttctggg aaaaattgtt gatcttcgat 1500
tacaccccaa gaaagtaccc ttacgatgtt ccagactatg cataagcggc cgc 1553

<210> SEQ ID NO 16
<211> LENGTH: 2918
<212> TYPE: DNA
<213> ORGANISM: Artificial Sequence
<220> FEATURE:
<223> OTHER INFORMATION: Codon optimized

<400> SEQUENCE: 16
actagtatgg gtttatcatc cgtctgtact ttctccttcc aaactaacta tcatacctta 60
ttgaatcctc acaacaacaa tccaaaaaca tcattgttgt gttacagaca tccaaagaca 120
cctattaagt actcttacaa caactttcca tcaaaacatt gttcaaccaa gtccttccac 180
ttacaaaata agtgctccga aagtttgtct atagctaaga actctatcag agctgcaact 240
acaaatcaaa ctgaaccacc tgaaagtgat aatcactctg ttgccacaaa aattttgaac 300
ttcggtaaag catgttggaa gttgcaaaga ccatacacca taatcgcttt tacttcttgt 360
gcatgcggtt tattcggtaa agaattgttg cataacacta acttaatttc atggtccttg 420
atgttcaagg catttttctt tttagttgcc atcttgtgca tcgcttcatt caccactaca 480
attaatcaaa tatacgattt gcacatcgac agaattaaca aaccagattt gcctttggct 540
tcaggtgaaa tatccgtcaa tactgcatgg atcatgtcta tcatagtagc cttgttcggt 600
ttgatcatca caattaaaat gaagggtggt ccattgtaca tcttcggtta ctgtttcggt 660
atcttcggtg gtattgtcta ttccgtacca ccttttagat ggaaacaaaa ccctagtact 720
gcctttttgt tgaatttctt agctcatatc atcacaaact tcaccttcta ctacgcttca 780
agagctgctt taggtttgcc attcgaattg agaccttcat tcacattttt gttggcattc 840
atgaaaagta tgggttctgc attagccttg atcaaggatg cctctgacgt tgaaggtgac 900
acaaagttcg gtattagtac cttggcttct aagtacggtt caagaaattt gactttgttc 960
tgctccggta tcgttttgtt aagttacgtc gcagccattt tggcaggtat catttggcca 1020
caagccttta attctaacgt tatgttgttg tcacatgcca tcttggcttt ctggttgatc 1080
ttgcaaacta gagatttcgc tttgacaaat tatgaccctg aagcaggtag aagattctac 1140
gagtttatgt ggaaattgta ctacgctgaa tatttggtat acgtttttat tgaaggtaga 1200
ggttctttgt tgacctgtgg tgacgttgaa gaaaatccag gtcctatgaa atgttcaact 1260
ttctcctttt ggttcgtatg caagatcatc ttcttttttct tttcctttaa catccaaaca 1320
agtatcgcaa acccaagaga aaactttttg aagtgcttct cacaatacat acctaataac 1380

```
gccaccaatt tgaagttggt ttacactcaa aacaacccat tgtacatgtc cgtcttgaac   1440

agtacaatcc ataatttgag attcacttct gataccactc caaaaccttt ggtcattgta   1500

acccctagtc atgtatctca catccaaggt actatcttat gttctaaaaa ggttggtttg   1560

caaattagaa ctagatccgg tggtcatgat agtgaaggca tgtcatacat ctcccaagtt   1620

ccattcgtta tcgttgattt gagaaacatg agatcaatta aaatagacgt acactcacaa   1680

actgcttggg ttgaagctgg tgcaacattg ggtgaagtat actactgggt taacgaaaag   1740

aatgaaaact tatcattggc tgctggttac tgtccaacag tttgcgcagg tggtcatttt   1800

ggtggtggtg gttatggtcc tttaatgaga aactacggtt tggccgctga taacataatc   1860

gacgctcatt tggtaaatgt tcacggtaaa gttttggata gaaagtctat gggtgaagac   1920

ttattttggg ctttgagagg tggtggtgca gaatcattcg gtatcatagt tgcttggaag   1980

ataagattag tcgcagtacc aaagtctact atgttctcag tcaaaaagat aatggaaatc   2040

catgaattag ttaaattggt caataagtgg caaaacatcg catacaagta cgataaggac   2100

ttgttgttga tgactcattt catcacaaga aacatcaccg ataaccaagg taaaaataag   2160

actgctatcc acacatactt ttcttcagtt ttcttgggtg gtgtcgattc cttagtagac   2220

ttgatgaata agtcttttcc agaattaggt attaagaaaa ctgattgtag acaattgtct   2280

tggatcgaca ccatcatctt ttattcaggt gttgtcaact acgatacaga caacttcaac   2340

aaagaaatat tattggatag atccgcaggt caaaacggtg cctttaaaat taagttagac   2400

tacgttaaaa agccaatacc tgaatcagtt ttcgtccaaa tcttagaaaa attgtacgaa   2460

gaagatattg gtgcaggcat gtacgccttg tatccatacg gtggtataat ggacgaaatc   2520

agtgaatctg ccattccatt tcctcataga gctggtatct tatacgaatt gtggtacatt   2580

tgttcatggg aaaagcaaga agataacgaa aagcacttaa actggattag aaacatctat   2640

aacttcatga ctccatacgt ttctaaaaac cctagattgg catatttgaa ctacagagat   2700

ttggacatcg gtattaacga tccaaagaat cctaacaact atacccaagc tagaatttgg   2760

ggtgaaaaat acttcggtaa aaatttcgat agattagtaa aggttaagac attggttgac   2820

ccaaacaact tctttagaaa cgaacaatcc attccacctt tacctagaca tagacacgaa   2880

caaaaattaa taagtgaaga agatttgtaa gcggccgc                          2918
```

<210> SEQ ID NO 17
<211> LENGTH: 167
<212> TYPE: DNA
<213> ORGANISM: Artificial Sequence
<220> FEATURE:
<223> OTHER INFORMATION: Codon optimized

<400> SEQUENCE: 17

```
agccaaaata atgataacga gaataatatc aagaatacct tagaacaaca tcgacaacaa     60

caacaggcat tttcggatat gagtcacgtg gagtattcca gaattacaaa atttttttcaa   120

gaacaaccac tggagggata taccctttc tctcacaggt ctgcgcc                  167
```

<210> SEQ ID NO 18
<211> LENGTH: 1518
<212> TYPE: DNA
<213> ORGANISM: Artificial Sequence
<220> FEATURE:
<223> OTHER INFORMATION: Codon optimized

<400> SEQUENCE: 18

```
atggtttcca atcacttgtt tgacgcaatg agagccgctg cccctggtaa cgccccttc     60
```

ataagaatag ataatactag aacttggaca tacgatgacg cctttgcttt atctggtaga 120
atagcatcag ctatggatgc tttgggtatc agaccaggtg acagagtcgc agttcaagta 180
gaaaaatccg ctgaagcatt gatcttgtat ttggcttgtt tgagaagtgg tgcagtttat 240
ttgccattga atactgccta cacattagct gaattggatt acttcatagg tgacgcagaa 300
cctagattgg ttgtagtcgc ctcttcagcc agagctggtg tagaaacaat tgctaaacca 360
agaggtgcaa tagtcgaaac cttagatgct gctggttctg gtagtttgtt agatttggcc 420
agagacgaac ctgctgattt tgttgacgct tcaagatcag ccgatgactt agccgctatt 480
ttgtacacct ctggtactac aggtagatca aagggtgcta tgttgactca tggtaatttg 540
ttgtcaaacg cattaacctt gagagatttc tggagagtta ctgccggtga cagattaatc 600
cacgctttgc caatttttca tactcacggt ttattcgttg ctaccaacgt aactttgtta 660
gcaggtgcct ccatgttctt gttgagtaag ttcgatccag aagaaatatt atctttgatg 720
cctcaagcta ctatgttgat gggtgtccca acattctacg ttagattgtt acaatcacct 780
agattagata agcaagctgt tgcaaacatc agattgttta tatccggtag tgctccattg 840
ttagcagaaa cccatactga atttcaagca agaacaggtc acgccatttt agaaagatac 900
ggtatgacag aaaccaatat gaacacttct aacccttatg aaggtaaaag aatagctggt 960
acagttggtt ttccattgcc tgatgtcaca gttagagtaa ccgacccagc cactggttta 1020
gctttgccac ctgaacaaac tggtatgatc gaaattaaag gtccaaacgt ttttaagggt 1080
tactggagaa tgcctgaaaa gactgctgct gagtttactg ctgatggttt ctttatctct 1140
ggtgacttag gtaaaattga tagagacggt tatgtccata ttgttggtcg tggtaaagat 1200
ttggttatat ccggtggtta taacatctac cctaaggaag tagaaggtga aatagatcaa 1260
atcgaaggtg ttgtagaatc agctgtaata ggtgtcccac atcctgattt tggtgaaggt 1320
gttacagcag tcgttgtaag aaaaccaggt gctgcattag atgaaaaggc aattgtttct 1380
gccttacaag acagattggc tagatacaag caaccaaaga gaataatctt cgcagaagat 1440
ttgcctagaa atactatggg taaagtacaa aagaacatct tgagacaaca atacgccgac 1500
ttatacacca gaacctga 1518

<210> SEQ ID NO 19
<211> LENGTH: 2092
<212> TYPE: DNA
<213> ORGANISM: Artificial Sequence
<220> FEATURE:
<223> OTHER INFORMATION: Codon optimized

<400> SEQUENCE: 19
actagtatgg gtttatcatc cgtctgtact ttctccttcc aaactaacta tcatacctta 60
ttgaatcctc acaacaacaa tccaaaaaca tcattgttgt gttacagaca tccaaagaca 120
cctattaagt actcttacaa caactttcca tcaaaacatt gttcaaccaa gtccttccac 180
ttacaaaata agtgctccga aagtttgtct atagctaaga actctatcag agctgcaact 240
acaaatcaaa ctgaaccacc tgaaagtgat aatcactctg ttgccacaaa aattttgaac 300
ttcggtaaag catgttggaa gttgcaaaga ccatacacca taatcgcttt tacttcttgt 360
gcatgcggtt tattcggtaa agaattgttg cataacacta acttaatttc atggtcctat 420
gaactgctcc gcattctctt tctggttcgt ctgtaaaata atcttcttct tcttgtcctt 480
caacatccaa atctccatcg caaatccaca agaaaacttt ttgaagtgtt tctccgaata 540

```
catcccaaac aaccctgcta acccaaagtt tatatatact caacatgatc aattgtacat    600

gtccgttttg aacagtacca tccaaaattt gagattcact tctgacacta caccaaaacc    660

tttagtcatt gttacacctt ccaatgttag tcacattcaa gcttctatat tgtgctctaa    720

gaaagtaggt ttgcaaatca gaactagatc aggtggtcat gatgcagaag gcatgtctta    780

catctcacaa gttccattcg ttgtagtcga tttgagaaat atgcattcca taaagatcga    840

cgttcacagt caaacagcat gggtagaagc aggtgccacc ttgggtgaag tttactactg    900

gatcaacgaa aagaatgaaa acttttcttt ccctggtggt tactgtccaa cagtaggtgt    960

cggtggtcac ttttctggtg gtggttatgg tgcattgatg agaaactacg gtttagctgc   1020

agataatatt atagacgccc atttggttaa cgtagatggt aaagttttgg acagaaagtc   1080

tatgggtgaa gatttgtttt gggccataag aggtggtggt ggtgaaaatt tcggtatcat   1140

tgccgcttgg aaaattaagt tagtcgctgt tccttccaaa agtactattt tctctgtcaa   1200

aaagaacatg gaaatccacg gtttggttaa gttgtttaat aagtggcaaa acatcgctta   1260

caagtacgat aaggacttgg ttttgatgac ccatttcatc actaaaaata ttacagataa   1320

ccatggtaaa aataagacca ctgttcacgg ttatttttct tcaattttcc atggtggtgt   1380

agattctttg gttgatttga tgaataagtc attcccagaa ttgggtatta aaaagacaga   1440

ttgcaaggaa ttttcttgga tagacacaac catcttctat tcaggtgttg taaacttcaa   1500

caccgctaac ttcaaaaagg aaatcttgtt ggatagatcc gctggtaaaa agaccgcttt   1560

ttctattaaa ttggactacg ttaagaaacc aatccctgaa actgcaatgg tcaagatatt   1620

ggaaaagttg tacgaagaag atgtaggtgt cggcatgtac gttttgtatc catacggtgg   1680

tattatggaa gaaatatctg aatcagccat accatttcct cacagagctg gtatcatgta   1740

tgaattatgg tacacagcct catgggaaaa gcaagaagat aacgaaaagc atatcaactg   1800

ggtcagatcc gtttacaact tcactacacc ttacgttagt caaaacccaa gattggcata   1860

tttgaactac agagatttgg acttaggtaa aactaaccct gaatctccaa ataactatac   1920

acaagcaaga atttggggtg aaaagtactt tggtaaaaat ttcaacagat tagttaaagt   1980

aaagactaaa gccgacccta acaacttttt cagaaacgaa caatccatcc cacctttgcc   2040

acctcaccac cacgaacaaa aattaataag tgaagaagat ttgtaagtcg ac           2092
```

<210> SEQ ID NO 20
<211> LENGTH: 7904
<212> TYPE: DNA
<213> ORGANISM: Artificial Sequence
<220> FEATURE:
<223> OTHER INFORMATION: Codon optimized

<400> SEQUENCE: 20

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatcga ctacgtcgta aggccgtttc tgacagagta aaattcttga gggaactttc    240

accattatgg gaaatggttc aagaaggtat tgacttaaac tccatcaaat ggtcaggtca    300

ttgagtgttt tttatttgtt gtattttttt ttttttagag aaaatcctcc aatatcaaat    360

taggaatcgt agtttcatga ttttctgtta cacctaactt tttgtgtggt gccctcctcc    420

ttgtcaatat taatgttaaa gtgcaattct ttttccttat cacgttgagc cattagtatc    480

aatttgctta cctgtattcc tttactatcc tcctttttct ccttcttgat aaatgtatgt    540
```

```
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140
acagtttttc tccataatct tgaagaggcc aaaacattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg atttttagta aaccttgttc aggtctaaca   1500
ctaccggtac cccatttagg accacccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacatagg ggcagacatt agaatggtat atccttgaaa tatatatata   1800
tattgctgaa atgtaaaagg taagaaaagt tagaaagtaa gacgattgct aaccacctat   1860
tggaaaaaac aataggtcct taaataatat tgtcaacttc aagtattgtg atgcaagcat   1920
ttagtcatga acgcttctct attctatatg aaaagccggt tccggcctct cacctttcct   1980
ttttctccca atttttcagt tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca tttttaataa ggcaataata ttaggtatgt ggatatacta   2400
gaagttctcc tcgagggtcg atatgcggtg tgaaataccg cacagatgcg taaggagaaa   2460
ataccgcatc aggaaattgt aaacgttaat attttgttaa aattcgcgtt aaatttttgt   2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gcccccgatt tagagcttga cggggaaagc cggcgaacgt ggcgagaaag   2820
gaagggaaga aagcgaaagg agcgggcgct agggcgctgg caagtgtagc ggtcacgctg   2880
```

```
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aggggggatg tgctgcaagg cgattaagtt gggtaacgcc agggttttcc   3060
cagtcacgac gttgtaaaac gacggccagt gaattgtaat acgactcact atagggcgaa   3120
ttggagctct agtacggatt agaagccgcc gagcgggcga cagccctccg acggaagact   3180
ctcctccgtg cgtcctcgtc ttcaccggtc gcgttcctga aacgcagatg tgcctcgcgc   3240
cgcactgctc cgaacaataa agattctaca atactagctt ttatggttat gaagaggaaa   3300
aattggcagt aacctggccc cacaaacctt caaattaacg aatcaaatta acaaccatag   3360
gatgataatg cgattagttt tttagcctta tttctggggt aattaatcag cgaagcgatg   3420
atttttgatc tattaacaga tatataaatg gaaaagctgc ataaccactt taactaatac   3480
tttcaacatt ttcagtttgt attacttctt attcaaatgt cataaaagta tcaacaaaaa   3540
attgttaata tacctctata ctttaacgtc aaggagaaaa aaccccggat tctagaacta   3600
gtggatcccc catcacaagt ttgtacaaaa aagctgaacg agaaacgtaa aatgatataa   3660
atatcaatat attaaattag attttgcata aaaaacagac tacataatac tgtaaaacac   3720
aacatatcca gtcactatgg cggccgcatt aggcacccca ggctttacac tttatgcttc   3780
cggctcgtat aatgtgtgga ttttgagtta ggatccgtcg agattttcag gagctaagga   3840
agctaaaatg gagaaaaaaa tcactggata taccaccgtt gatatatccc aatggcatcg   3900
taaagaacat tttgaggcat ttcagtcagt tgctcaatgt acctataacc agaccgttca   3960
gctggatatt acggcctttt taaagaccgt aaagaaaaat aagcacaagt tttatccggc   4020
ctttattcac attcttgccc gcctgatgaa tgctcatccg gaattccgta tggcaatgaa   4080
agacggtgag ctggtgatat gggatagtgt tcacccttgt tacaccgttt tccatgagca   4140
aactgaaacg ttttcatcgc tctggagtga ataccacgac gatttccggc agtttctaca   4200
catatattcg caagatgtgg cgtgttacgg tgaaaacctg gcctatttcc ctaaagggtt   4260
tattgagaat atgtttttcg tctcagccaa tccctgggtg agtttcacca gttttgattt   4320
aaacgtggcc aatatggaca acttcttcgc ccccgttttc accatgggca aatattatac   4380
gcaaggcgac aaggtgctga tgccgctggc gattcaggtt catcatgccg tctgtgatgg   4440
cttccatgtc ggcagaatgc ttaatgaatt acaacagtac tgcgatgagt ggcagggcgg   4500
ggcgtaaacg ccgcgtggat ccggcttact aaaagccaga taacagtatg cgtatttgcg   4560
cgctgatttt tgcggtataa gaatatatac tgatatgtat acccgaagta tgtcaaaaag   4620
aggtatgcta tgaagcagcg tattacagtg acagttgaca gcgacagcta tcagttgctc   4680
aaggcatata tgatgtcaat atctccggtc tggtaagcac aaccatgcag aatgaagccc   4740
gtcgtctgcg tgccgaacgc tggaaagcgg aaaatcagga agggatggct gaggtcgccc   4800
ggtttattga aatgaacggc tcttttgctg acgagaacag gggctggtga aatgcagttt   4860
aaggtttaca cctataaaag agagagccgt tatcgtctgt ttgtggatgt acagagtgat   4920
attattgaca cgcccgggcg acggatggtg atccccctgg ccagtgcacg tctgctgtca   4980
gataaagtct cccgtgaact ttacccggtg gtgcatatcg gggatgaaag ctggcgcatg   5040
atgaccaccg atatggccag tgtgccggtc tccgttatcg gggaagaagt ggctgatctc   5100
agccaccgcg aaaatgacat caaaaacgcc attaacctga tgttctgggg aatataaatg   5160
tcaggctccc ttatacacag ccagtctgca ggtcgaccat agtgactgga tatgttgtgt   5220
tttacagtat tatgtagtct gtttttttatg caaaatctaa tttaatatat tgatatttat   5280
```

```
atcattttac gtttctcgtt cagctttctt gtacaaagtg gtgatgggct gcaggaattc   5340
gatatcaagc ttatcgatac cgtcgacctc gagtcatgta attagttatg tcacgcttac   5400
attcacgccc tccccccaca tccgctctaa ccgaaaagga aggagttaga caacctgaag   5460
tctaggtccc tatttatttt tttatagtta tgttagtatt aagaacgtta tttatatttc   5520
aaatttttct ttttttctg tacagacgcg tgtacgcatg taacattata ctgaaaacct   5580
tgcttgagaa ggttttggga cgctcgaagg ctttaatttg cggccggtac ccagcttttg   5640
ttccctttag tgagggttaa ttccgagctt ggcgtaatca tggtcatagc tgtttcctgt   5700
gtgaaattgt tatccgctca caattccaca caacatagga gccggaagca taaagtgtaa   5760
agcctggggt gcctaatgag tgaggtaact cacattaatt gcgttgcgct cactgcccgc   5820
tttccagtcg ggaaacctgt cgtgccagct gcattaatga atcggccaac gcgcggggag   5880
aggcggtttg cgtattgggc gctcttccgc ttcctcgctc actgactcgc tgcgctcggt   5940
cgttcggctg cggcgagcgg tatcagctca ctcaaaggcg gtaatacggt tatccacaga   6000
atcaggggat aacgcaggaa agaacatgtg agcaaaaggc cagcaaaagg ccaggaaccg   6060
taaaaaggcc gcgttgctgg cgtttttcca taggctcggc ccccctgacg agcatcacaa   6120
aaatcgacgc tcaagtcaga ggtggcgaaa cccgacagga ctataaagat accaggcgtt   6180
ccccctgga agctccctcg tgcgctctcc tgttccgacc ctgccgctta ccggatacct   6240
gtccgccttt ctcccttcgg gaagcgtggc gctttctcaa tgctcacgct gtaggtatct   6300
cagttcggtg taggtcgttc gctccaagct gggctgtgtg cacgaacccc ccgttcagcc   6360
cgaccgctgc gccttatccg gtaactatcg tcttgagtcc aacccggtaa gacacgactt   6420
atcgccactg gcagcagcca ctggtaacag gattagcaga gcgaggtatg taggcggtgc   6480
tacagagttc ttgaagtggt ggcctaacta cggctacact agaaggacag tatttggtat   6540
ctgcgctctg ctgaagccag ttaccttcgg aaaaagagtt ggtagctctt gatccggcaa   6600
acaaaccacc gctggtagcg gtggtttttt tgtttgcaag cagcagatta cgcgcagaaa   6660
aaaaggatct caagaagatc ctttgatctt ttctacgggg tctgacgctc agtggaacga   6720
aaactcacgt taagggattt tggtcatgag attatcaaaa aggatcttca cctagatcct   6780
tttaaattaa aaatgaagtt ttaaatcaat ctaaagtata tatgagtaaa cttggtctga   6840
cagttaccaa tgcttaatca gtgaggcacc tatctcagcg atctgtctat ttcgttcatc   6900
catagttgcc tgactgcccg tcgtgtagat aactacgata cgggagggct taccatctgg   6960
ccccagtgct gcaatgatac cgcgagaccc acgctcaccg gctccagatt tatcagcaat   7020
aaaccagcca gccggaaggg ccgagcgcag aagtggtcct gcaactttat ccgcctccat   7080
ccagtctatt aattgttgcc gggaagctag agtaagtagt tcgccagtta atagtttgcg   7140
caacgttgtt gccattgcta caggcatcgt ggtgtcacgc tcgtcgtttg gtatggcttc   7200
attcagctcc ggttcccaac gatcaaggcg agttacatga tcccccatgt tgtgaaaaaa   7260
agcggttagc tccttcggtc ctccgatcgt tgtcagaagt aagttggccg cagtgttatc   7320
actcatggtt atggcagcac tgcataattc tcttactgtc atgccatccg taagatgctt   7380
ttctgtgact ggtgagtact caaccaagtc attctgagaa tagtgtatgc ggcgaccgag   7440
ttgctcttgc ccggcgtcaa tacgggataa taccgcgcca catagcagaa ctttaaaagt   7500
gctcatcatt ggaaaacgtt cttcggggcg aaaactctca aggatcttac cgctgttgag   7560
atccagttcg atgtaaccca ctcgtgcacc caactgatct tcagcatctt ttactttcac   7620
```

```
cagcgtttct gggtgagcaa aaacaggaag gcaaaatgcc gcaaaaaagg gaataagggc   7680

gacacggaaa tgttgaatac tcatactctt cctttttcaa tattattgaa gcatttatca   7740

gggttattgt ctcatgagcg gatacatatt tgaatgtatt tagaaaaata aacaaatagg   7800

ggttccgcgc acatttcccc gaaaagtgcc acctgacgtc taagaaacca ttattatcat   7860

gacattaacc tataaaaata ggcgtatcac gaggcccttt cgtc                     7904
```

<210> SEQ ID NO 21
<211> LENGTH: 6773
<212> TYPE: DNA
<213> ORGANISM: Artificial Sequence
<220> FEATURE:
<223> OTHER INFORMATION: Codon optimized

<400> SEQUENCE: 21

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accacgcttt tcaattcaat tcatcatttt tttttattc tttttttga tttcggtttc     240

tttgaaattt ttttgattcg gtaatctccg aacagaagga agaacgaagg aaggagcaca    300

gacttagatt ggtatatata cgcatatgta gtgttgaaga aacatgaaat tgcccagtat    360

tcttaaccca actgcacaga acaaaaacct gcaggaaacg aagataaatc atgtcgaaag    420

ctacatataa ggaacgtgct gctactcatc ctagtcctgt tgctgccaag ctatttaata    480

tcatgcacga aaagcaaaca aacttgtgtg cttcattgga tgttcgtacc accaaggaat    540

tactggagtt agttgaagca ttaggtccca aaatttgttt actaaaaaca catgtggata    600

tcttgactga tttttccatg gagggcacag ttaagccgct aaaggcatta tccgccaagt    660

acaatttttt actcttcgaa gacagaaaat ttgctgacat tggtaataca gtcaaattgc    720

agtactctgc gggtgtatac agaatagcag aatgggcaga cattacgaat gcacacggtg    780

tggtgggccc aggtattgtt agcggtttga agcaggcggc agaagaagta acaaaggaac    840

ctagaggcct tttgatgtta gcagaattgt catgcaaggg ctccctatct actggagaat    900

atactaaggg tactgttgac attgcgaaga gcgacaaaga ttttgttatc ggctttattg    960

ctcaaagaga catgggtgga agagatgaag gttacgattg gttgattatg acacccggtg   1020

tgggtttaga tgacaaggga gacgcattgg gtcaacagta tagaaccgtg gatgatgtgg   1080

tctctacagg atctgacatt attattgttg gaagaggact atttgcaaag ggaagggatg   1140

ctaaggtaga gggtgaacgt tacagaaaag caggctggga agcatatttg agaagatgcg   1200

gccagcaaaa ctaaaaaact gtattataag taaatgcatg tatactaaac tcacaaatta   1260

gagcttcaat ttaattatat cagttattac cctgcggtgt gaaataccgc acagatgcgt   1320

aaggagaaaa taccgcatca ggaaattgta aacgttaata ttttgttaaa attcgcgtta   1380

aatttttgtt aaatcagctc atttttaac caataggccg aaatcggcaa aatcccttat    1440

aaatcaaaag aatagaccga gatagggttg agtgttgttc cagtttggaa caagagtcca   1500

ctattaaaga acgtggactc caacgtcaaa gggcgaaaaa ccgtctatca gggcgatggc   1560

ccactacgtg aaccatcacc ctaatcaagt tttttggggt cgaggtgccg taaagcacta   1620

aatcggaacc ctaaagggag cccccgattt agagcttgac ggggaaagcc ggcgaacgtg   1680

gcgagaaagg aagggaagaa agcgaaagga gcgggcgcta gggcgctggc aagtgtagcg   1740

gtcacgctgc gcgtaaccac cacacccgcc gcgcttaatg cgccgctaca gggcgcgtcg   1800
```

```
cgccattcgc cattcaggct gcgcaactgt tgggaagggc gatcggtgcg ggcctcttcg   1860
ctattacgcc agctggcgaa gggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcacaagtt tgtacaaaaa agctgaacga gaaacgtaaa   2520
atgatataaa tatcaatata ttaaattaga ttttgcataa aaaacagact acataatact   2580
gtaaaacaca acatatccag tcactatggc ggccgcatta ggcaccccag gctttacact   2640
ttatgcttcc ggctcgtata atgtgtggat tttgagttag gatccgtcga gattttcagg   2700
agctaaggaa gctaaaatgg agaaaaaaat cactggatat accaccgttg atatatccca   2760
atggcatcgt aaagaacatt ttgaggcatt tcagtcagtt gctcaatgta cctataacca   2820
gaccgttcag ctggatatta cggccttttt aaagaccgta aagaaaaata agcacaagtt   2880
ttatccggcc tttattcaca ttcttgcccg cctgatgaat gctcatccgg aattccgtat   2940
ggcaatgaaa gacggtgagc tggtgatatg ggatagtgtt cacccttgtt acaccgtttt   3000
ccatgagcaa actgaaacgt tttcatcgct ctggagtgaa taccacgacg atttccggca   3060
gtttctacac atatattcgc aagatgtggc gtgttacggt gaaaacctgg cctatttccc   3120
taaagggttt attgagaata tgtttttcgt ctcagccaat ccctgggtga gtttcaccag   3180
ttttgattta aacgtggcca atatggacaa cttcttcgcc cccgttttca ccatgggcaa   3240
atattatacg caaggcgaca aggtgctgat gccgctggcg attcaggttc atcatgccgt   3300
ctgtgatggc ttccatgtcg gcagaatgct taatgaatta caacagtact gcgatgagtg   3360
gcagggcggg gcgtaaacgc cgcgtggatc cggcttacta aaagccagat aacagtatgc   3420
gtatttgcgc gctgattttt gcggtataag aatatatact gatatgtata cccgaagtat   3480
gtcaaaaaga ggtatgctat gaagcagcgt attacagtga cagttgacag cgacagctat   3540
cagttgctca aggcatatat gatgtcaata tctccggtct ggtaagcaca accatgcaga   3600
atgaagcccg tcgtctgcgt gccgaacgct ggaaagcgga aaatcaggaa gggatggctg   3660
aggtcgcccg gtttattgaa atgaacggct cttttgctga cgagaacagg ggctggtgaa   3720
atgcagttta aggtttacac ctataaaaga gagagccgtt atcgtctgtt tgtggatgta   3780
cagagtgata ttattgacac gcccgggcga cggatggtga tccccctggc cagtgcacgt   3840
ctgctgtcag ataaagtctc ccgtgaactt tacccggtgg tgcatatcgg ggatgaaagc   3900
tggcgcatga tgaccaccga tatggccagt gtgccggtct ccgttatcgg ggaagaagtg   3960
gctgatctca gccaccgcga aaatgacatc aaaaacgcca ttaacctgat gttctgggga   4020
atataaatgt caggctccct tatacacagc cagtctgcag gtcgaccata gtgactggat   4080
atgttgtgtt ttacagtatt atgtagtctg ttttttatgc aaaatctaat ttaatatatt   4140
```

```
gatatttata tcattttacg tttctcgttc agctttcttg tacaaagtgg tgatgggctg   4200
caggaattcg atatcaagct tatcgatacc gtcgacctcg agtcatgtaa ttagttatgt   4260
cacgcttaca ttcacgccct ccccccacat ccgctctaac cgaaaaggaa ggagttagac   4320
aacctgaagt ctaggtccct atttattttt ttatagttat gttagtatta agaacgttat   4380
ttatatttca aatttttctt ttttttctgt acagacgcgt gtacgcatgt aacattatac   4440
tgaaaacctt gcttgagaag gttttgggac gctcgaaggc tttaatttgc ggccggtacc   4500
cagcttttgt tccctttagt gagggttaat tccgagcttg gcgtaatcat ggtcatagct   4560
gtttcctgtg tgaaattgtt atccgctcac aattccacac aacataggag ccggaagcat   4620
aaagtgtaaa gcctggggtg cctaatgagt gaggtaactc acattaattg cgttgcgctc   4680
actgcccgct ttccagtcgg gaaacctgtc gtgccagctg cattaatgaa tcggccaacg   4740
cgcggggaga ggcggtttgc gtattgggcg ctcttccgct tcctcgctca ctgactcgct   4800
gcgctcggtc gttcggctgc ggcgagcggt atcagctcac tcaaaggcgg taatacggtt   4860
atccacagaa tcaggggata acgcaggaaa gaacatgtga gcaaaaggcc agcaaaaggc   4920
caggaaccgt aaaaaggccg cgttgctggc gtttttccat aggctcggcc cccctgacga   4980
gcatcacaaa aatcgacgct caagtcagag gtggcgaaac ccgacaggac tataaagata   5040
ccaggcgttc ccccctggaa gctccctcgt gcgctctcct gttccgaccc tgccgcttac   5100
cggatacctg tccgcctttc tcccttcggg aagcgtggcg ctttctcaat gctcacgctg   5160
taggtatctc agttcggtgt aggtcgttcg ctccaagctg ggctgtgtgc acgaaccccc   5220
cgttcagccc gaccgctgcg ccttatccgg taactatcgt cttgagtcca acccggtaag   5280
acacgactta tcgccactgg cagcagccac tggtaacagg attagcagag cgaggtatgt   5340
aggcggtgct acagagttct tgaagtggtg gcctaactac ggctacacta gaaggacagt   5400
atttggtatc tgcgctctgc tgaagccagt taccttcgga aaaagagttg gtagctcttg   5460
atccggcaaa caaaccaccg ctggtagcgg tggttttttt gtttgcaagc agcagattac   5520
gcgcagaaaa aaaggatctc aagaagatcc tttgatcttt tctacggggt ctgacgctca   5580
gtggaacgaa aactcacgtt aagggatttt ggtcatgaga ttatcaaaaa ggatcttcac   5640
ctagatcctt ttaaattaaa aatgaagttt taaatcaatc taaagtatat atgagtaaac   5700
ttggtctgac agttaccaat gcttaatcag tgaggcacct atctcagcga tctgtctatt   5760
tcgttcatcc atagttgcct gactgcccgt cgtgtagata actacgatac gggagggctt   5820
accatctggc cccagtgctg caatgatacc gcgagaccca cgctcaccgg ctccagattt   5880
atcagcaata aaccagccag ccggaagggc cgagcgcaga agtggtcctg caactttatc   5940
cgcctccatc cagtctatta attgttgccg ggaagctaga gtaagtagtt cgccagttaa   6000
tagtttgcgc aacgttgttg ccattgctac aggcatcgtg gtgtcacgct cgtcgtttgg   6060
tatggcttca ttcagctccg gttcccaacg atcaaggcga gttacatgat cccccatgtt   6120
gtgaaaaaaa gcggttagct ccttcggtcc tccgatcgtt gtcagaagta agttggccgc   6180
agtgttatca ctcatggtta tggcagcact gcataattct cttactgtca tgccatccgt   6240
aagatgcttt tctgtgactg gtgagtactc aaccaagtca ttctgagaat agtgtatgcg   6300
gcgaccgagt tgctcttgcc cggcgtcaat acgggataat accgcgccac atagcagaac   6360
tttaaaagtg ctcatcattg gaaaacgttc ttcggggcga aaactctcaa ggatcttacc   6420
gctgttgaga tccagttcga tgtaacccac tcgtgcaccc aactgatctt cagcatcttt   6480
tactttcacc agcgtttctg ggtgagcaaa aacaggaagg caaaatgccg caaaaaaggg   6540
```

```
aataagggcg acacggaaat gttgaatact catactcttc ctttttcaat attattgaag   6600

catttatcag ggttattgtc tcatgagcgg atacatattt gaatgtattt agaaaaataa   6660

acaaataggg gttccgcgca catttccccg aaaagtgcca cctgacgtct aagaaaccat   6720

tattatcatg acattaacct ataaaaatag gcgtatcacg aggccctttc gtc          6773
```

<210> SEQ ID NO 22
<211> LENGTH: 7690
<212> TYPE: DNA
<213> ORGANISM: Artificial Sequence
<220> FEATURE:
<223> OTHER INFORMATION: Codon optimized

<400> SEQUENCE: 22

```
ttatcatgac attaacctat aaaaataggc gtatcacgag gccctttcgt ctcgcgcgtt     60

tcggtgatga cggtgaaaac ctctgacaca tgcagctccc ggagacggtc acagcttgtc    120

tgtaagcgga tgccgggagc agacaagccc gtcagggcgc gtcagcgggt gttggcgggt    180

gtcggggctg gcttaactat gcggcatcag agcagattgt actgagagtg caccacgctt    240

ttcaattcaa ttcatcattt ttttttattc ttttttttg atttcggttt ctttgaaatt    300

tttttgattc ggtaatctcc gaacagaagg aagaacgaag gaaggagcac agacttagat    360

tggtatatat acgcatatgt agtgttgaag aaacatgaaa ttgcccagta ttcttaaccc    420

aactgcacag aacaaaaacc tgcaggaaac gaagataaat catgtcgaaa gctacatata    480

aggaacgtgc tgctactcat cctagtcctg ttgctgccaa gctatttaat atcatgcacg    540

aaaagcaaac aaacttgtgt gcttcattgg atgttcgtac caccaaggaa ttactggagt    600

tagttgaagc attaggtccc aaaatttgtt tactaaaaac acatgtggat atcttgactg    660

atttttccat ggagggcaca gttaagccgc taaaggcatt atccgccaag tacaattttt    720

tactcttcga agacagaaaa tttgctgaca ttggtaatac agtcaaattg cagtactctg    780

cgggtgtata cagaatagca gaatgggcag acattacgaa tgcacacggt gtggtgggcc    840

caggtattgt tagcggtttg aagcaggcgg cagaagaagt aacaaaggaa cctagaggcc    900

ttttgatgtt agcagaattg tcatgcaagg gctccctatc tactggagaa tatactaagg    960

gtactgttga cattgcgaag agcgacaaag attttgttat cggctttatt gctcaaagag   1020

acatgggtgg aagagatgaa ggttacgatt ggttgattat gacacccggt gtgggtttag   1080

atgacaaggg agacgcattg ggtcaacagt atagaaccgt ggatgatgtg gtctctacag   1140

gatctgacat tattattgtt ggaagaggac tatttgcaaa gggaagggat gctaaggtag   1200

agggtgaacg ttacagaaaa gcaggctggg aagcatattt gagaagatgc ggccagcaaa   1260

actaaaaaac tgtattataa gtaaatgcat gtatactaaa ctcacaaatt agagcttcaa   1320

tttaattata tcagttatta ccctgcggtg tgaaataccg cacagatgcg taaggagaaa   1380

ataccgcatc aggaaattgt aaacgttaat attttgttaa aattcgcgtt aaatttttgt   1440

taaatcagct cattttttaa ccaataggcc gaaatcggca aaatccctta taaatcaaaa   1500

gaatagaccg agatagggtt gagtgttgtt ccagtttgga acaagagtcc actattaaag   1560

aacgtggact ccaacgtcaa agggcgaaaa accgtctatc agggcgatgg cccactacgt   1620

gaaccatcac cctaatcaag ttttttgggg tcgaggtgcc gtaaagcact aaatcggaac   1680

cctaaaggga gcccccgatt tagagcttga cggggaaagc cggcgaacgt ggcgagaaag   1740

gaagggaaga aagcgaaagg agcgggcgct agggcgctgg caagtgtagc ggtcacgctg   1800
```

```
cgcgtaacca ccacacccgc cgcgcttaat gcgccgctac agggcgcgtc gcgccattcg   1860

ccattcaggc tgcgcaactg ttgggaaggg cgatcggtgc gggcctcttc gctattacgc   1920

cagctggcga aggggggatg tgctgcaagg cgattaagtt gggtaacgcc agggttttcc   1980

cagtcacgac gttgtaaaac gacggccagt gaattgtaat acgactcact atagggcgaa   2040

ttggagctct agtacggatt agaagccgcc gagcgggcga cagccctccg acggaagact   2100

ctcctccgtg cgtcctcgtc ttcaccggtc gcgttcctga aacgcagatg tgcctcgcgc   2160

cgcactgctc cgaacaataa agattctaca atactagctt ttatggttat gaagaggaaa   2220

aattggcagt aacctggccc cacaaacctt caaattaacg aatcaaatta acaaccatag   2280

gatgataatg cgattagttt tttagcctta tttctggggt aattaatcag cgaagcgatg   2340

atttttgatc tattaacaga tatataaatg gaaaagctgc ataaccactt taactaatac   2400

tttcaacatt ttcagtttgt attacttctt attcaaatgt cataaaagta tcaacaaaaa   2460

attgttaata tacctctata ctttaacgtc aaggagaaaa aaccccggat tctagaacta   2520

gtggatcccc catcatggtt tccaatcact tgtttgacgc aatgagagcc gctgcccctg   2580

gtaacgcccc tttcataaga atagataata ctagaacttg gacatacgat gacgcctttg   2640

ctttatctgg tagaatagca tcagctatgg atgctttggg tatcagacca ggtgacagag   2700

tcgcagttca agtagaaaaa tccgctgaag cattgatctt gtatttggct tgtttgagaa   2760

gtggtgcagt ttatttgcca ttgaatactg cctacacatt agctgaattg gattacttca   2820

taggtgacgc agaacctaga ttggttgtag tcgcctcttc agccagagct ggtgtagaaa   2880

caattgctaa accaagaggt gcaatagtcg aaaccttaga tgctgctggt tctggtagtt   2940

tgttagattt ggccagagac gaacctgctg attttgttga cgcttcaaga tcagccgatg   3000

acttagccgc tattttgtac acctctggta ctacaggtag atcaaagggt gctatgttga   3060

ctcatggtaa tttgttgtca aacgcattaa ccttgagaga tttctggaga gttactgccg   3120

gtgacagatt aatccacgct ttgccaattt ttcatactca cggtttattc gttgctacca   3180

acgtaacttt gttagcaggt gcctccatgt tcttgttgag taagttcgat ccagaagaaa   3240

tattatcttt gatgcctcaa gctactatgt tgatgggtgt cccaacattc tacgttagat   3300

tgttacaatc acctagatta gataagcaag ctgttgcaaa catcagattg tttatatccg   3360

gtagtgctcc attgttagca gaaacccata ctgaatttca agcaagaaca ggtcacgcca   3420

ttttagaaag atacggtatg acagaaacca atatgaacac ttctaaccct tatgaaggta   3480

aaagaatagc tggtacagtt ggttttccat tgcctgatgt cacagttaga gtaaccgacc   3540

cagccactgg tttagctttg ccacctgaac aaactggtat gatcgaaatt aaaggtccaa   3600

acgtttttaa gggttactgg agaatgcctg aaaagactgc tgctgagttt actgctgatg   3660

gtttctttat ctctggtgac ttaggtaaaa ttgatagaga cggttatgtc catattgttg   3720

gtcgtggtaa agatttggtt atatccggtg gttataacat ctaccctaag gaagtagaag   3780

gtgaaataga tcaaatcgaa ggtgttgtag aatcagctgt aataggtgtc ccacatcctg   3840

attttggtga aggtgttaca gcagtcgttg taagaaaacc aggtgctgca ttagatgaaa   3900

aggcaattgt ttctgcctta caagacagat tggctagata caagcaacca aagagaataa   3960

tcttcgcaga agatttgcct agaaatacta tgggtaaagt acaaaagaac atcttgagac   4020

aacaatacgc cgacttatac accagaaccg aaggtagagg ttctttgtta acatgtggtg   4080

acgttgaaga aaatccaggt cctatggctt cagaaaagga aataagaaga gaaagattct   4140

tgaacgtatt cccaaagtta gttgaagaat tgaacgctag tttgttagct tatggtatgc   4200
```

```
ctaaagaagc ctgcgattgg tatgctcact ctttaaacta caatactcca ggtggtaaat   4260
tgaatagagg tttgagtgta gttgatactt atgctatctt gtctaacaaa accgttgaac   4320
aattaggtca agaagaatac gaaaaggtcg ctatcttggg ttggtgtatt gaattgttgc   4380
aagcatactt tttggttgcc gatgacatga tggataagtc tataacaaga agaggtcaac   4440
catgctggta caaagttcca gaagttggtg aaatagccat aaatgatgct tttatgttgg   4500
aagccgctat ctataaattg ttgaagtcac atttcagaaa cgaaaagtac tacatcgata   4560
ttaccgaatt attccacgaa gttactttcc aaacagaatt gggtcaattg atggatttga   4620
taactgcacc tgaagataaa gttgacttgt caaagttttc cttgaagaaa cattcattca   4680
tcgtcacctt tgaaactgct tattactcct tctatttgcc agtcgccttg gctatgtacg   4740
tagctggtat tactgatgaa aaagacttga agcaagcaag agatgttttg atacctttgg   4800
gtgaatactt ccaaatccaa gatgactact tagactgttt cggtactcca gaacaaatag   4860
gtaaaatcgg tacagatatt caagacaata agtgcagttg ggttattaac aaggctttgg   4920
aattagcatc tgccgaacaa agaaagactt tggatgaaaa ctacggtaaa aaggactcag   4980
ttgctgaagc aaagtgtaag aaaattttta atgatttgaa gattgaacaa ttgtaccatg   5040
aatacgaaga atccatcgct aaagacttaa aggcaaagat tagtcaagtt gatgaatcaa   5100
gaggttttaa agccgacgtt ttgacagctt tcttgaataa ggtctacaag agatcaaagt   5160
gatgggctgc aggaattcga tatcaagctt atcgataccg tcgacctcga gtcatgtaat   5220
tagttatgtc acgcttacat tcacgccctc cccccacatc cgctctaacc gaaaaggaag   5280
gagttagaca acctgaagtc taggtcccta tttatttttt tatagttatg ttagtattaa   5340
gaacgttatt tatatttcaa atttttcttt tttttctgta cagacgcgtg tacgcatgta   5400
acattatact gaaaaccttg cttgagaagg ttttgggacg ctcgaaggct ttaatttgcg   5460
gccggtaccc agcttttgtt ccctttagtg agggttaatt ccgagcttgg cgtaatcatg   5520
gtcatagctg tttcctgtgt gaaattgtta tccgctcaca attccacaca acataggagc   5580
cggaagcata aagtgtaaag cctggggtgc ctaatgagtg aggtaactca cattaattgc   5640
gttgcgctca ctgcccgctt tccagtcggg aaacctgtcg tgccagctgc attaatgaat   5700
cggccaacgc gcggggagag gcggtttgcg tattgggcgc tcttccgctt cctcgctcac   5760
tgactcgctg cgctcggtcg ttcggctgcg gcgagcggta tcagctcact caaaggcggt   5820
aatacggtta tccacagaat caggggataa cgcaggaaag aacatgtgag caaaaggcca   5880
gcaaaaggcc aggaaccgta aaaaggccgc gttgctggcg tttttccata ggctcggccc   5940
ccctgacgag catcacaaaa atcgacgctc aagtcagagg tggcgaaacc cgacaggact   6000
ataaagatac caggcgttcc cccctggaag ctccctcgtg cgctctcctg ttccgaccct   6060
gccgcttacc ggatacctgt ccgcctttct cccttcggga agcgtggcgc tttctcaatg   6120
ctcacgctgt aggtatctca gttcggtgta ggtcgttcgc tccaagctgg gctgtgtgca   6180
cgaacccccc gttcagcccg accgctgcgc cttatccggt aactatcgtc ttgagtccaa   6240
cccggtaaga cacgacttat cgccactggc agcagccact ggtaacagga ttagcagagc   6300
gaggtatgta ggcggtgcta cagagttctt gaagtggtgg cctaactacg gctacactag   6360
aaggacagta tttggtatct gcgctctgct gaagccagtt accttcggaa aaagagttgg   6420
tagctcttga tccggcaaac aaaccaccgc tggtagcggt ggtttttttg tttgcaagca   6480
gcagattacg cgcagaaaaa aaggatctca agaagatcct ttgatctttt ctacggggtc   6540
```

```
tgacgctcag tggaacgaaa actcacgtta agggattttg gtcatgagat tatcaaaaag   6600

gatcttcacc tagatccttt taaattaaaa atgaagtttt aaatcaatct aaagtatata   6660

tgagtaaact tggtctgaca gttaccaatg cttaatcagt gaggcaccta tctcagcgat   6720

ctgtctattt cgttcatcca tagttgcctg actgcccgtc gtgtagataa ctacgatacg   6780

ggagggctta ccatctggcc ccagtgctgc aatgataccg cgagacccac gctcaccggc   6840

tccagattta tcagcaataa accagccagc cggaagggcc gagcgcagaa gtggtcctgc   6900

aactttatcc gcctccatcc agtctattaa ttgttgccgg gaagctagag taagtagttc   6960

gccagttaat agtttgcgca acgttgttgc cattgctaca ggcatcgtgg tgtcacgctc   7020

gtcgtttggt atggcttcat tcagctccgg ttcccaacga tcaaggcgag ttacatgatc   7080

ccccatgttg tgaaaaaaag cggttagctc cttcggtcct ccgatcgttg tcagaagtaa   7140

gttggccgca gtgttatcac tcatggttat ggcagcactg cataattctc ttactgtcat   7200

gccatccgta agatgctttt ctgtgactgg tgagtactca accaagtcat tctgagaata   7260

gtgtatgcgg cgaccgagtt gctcttgccc ggcgtcaata cgggataata ccgcgccaca   7320

tagcagaact ttaaaagtgc tcatcattgg aaaacgttct tcggggcgaa aactctcaag   7380

gatcttaccg ctgttgagat ccagttcgat gtaacccact cgtgcaccca actgatcttc   7440

agcatctttt actttcacca gcgtttctgg gtgagcaaaa acaggaaggc aaaatgccgc   7500

aaaaaaggga ataagggcga cacggaaatg ttgaatactc atactcttcc tttttcaata   7560

ttattgaagc atttatcagg gttattgtct catgagcgga tacatatttg aatgtattta   7620

gaaaaataaa caaatagggg ttccgcgcac atttccccga aaagtgccac ctgacgtcta   7680

agaaaccatt                                                          7690
```

<210> SEQ ID NO 23
<211> LENGTH: 2163
<212> TYPE: DNA
<213> ORGANISM: Artificial Sequence
<220> FEATURE:
<223> OTHER INFORMATION: Codon optimized

<400> SEQUENCE: 23

```
atgggtaaaa actataagtc cttggattca gtcgttgcct cagatttcat cgcattgggt     60

atcacctcag aagtagcaga aacattacat ggtagattgg cagaaatcgt ttgtaattat    120

ggtgctgcaa cccctcaaac ttggatcaac atcgctaacc atatcttgtc accagatttg    180

cctttctcct tacaccaaat gttgttttat ggttgctaca aggatttcgg tccagcccca    240

cctgcttgga ttccagaccc tgaaaaagtc aagtcaacta atttgggtgc tttgttggaa    300

aagagaggta aagaattttt gggtgtaaag tacaaagatc caatttcttc tttttctcac    360

ttccaagaat tttctgttag aaaccctgaa gtctattgga gaacagtatt gatggatgaa    420

atgaaaatta gtttctctaa ggacccagaa tgtatcttga gaagagatga catcaacaac    480

ccaggtggtt ctgaatggtt acctggtggt tacttgaact cagctaaaaa ttgcttgaac    540

gtaaactcca ataagaaatt gaacgatact atgatcgttt ggagagacga gggtaacgat    600

gacttgcctt tgaataagtt gacattagat caattgagaa agagagtttg gttggttggt    660

tatgcattgg aagaaatggg tttagaaaaa ggttgtgcaa tagccatcga tatgccaatg    720

catgttgatg ctgttgttat atatttggcc atagtattgg ctggttacgt agttgtctct    780

atagcagatt cattttccgc ccctgaaatc tcaactagat tgagattatc caaagctaag    840

gcaattttca cacaagatca catcatcaga ggtaaaaaga gaataccatt gtattcaaga    900
```

```
gtagttgaag ctaaatcccc aatggcaata gttatccctt gtagtggttc taacattggt    960

gcagaattga gagatggtga catatcttgg gattactttt tagaaagagc caaggagttt   1020

aaaaactgcg agtttactgc cagagaacaa cctgttgatg cttatactaa catcttattc   1080

tccagtggta ctacaggtga accaaaagca attccttgga cacaagccac cccattgaag   1140

gctgctgctg atggttggtc tcatttggat attagaaaag gtgacgttat agtatggcca   1200

actaatttgg gttggatgat gggtccttgg ttggtttatg ctagtttgtt aaatggtgca   1260

tctattgcct tgtacaacgg tagtccttta gtctctggtt tcgctaaatt tgttcaagat   1320

gcaaaggtca caatgttggg tgtcgtacca tctattgtaa gatcatggaa atccacaaat   1380

tgtgtttcag gttacgattg gtccaccata agatgctttt cttcatccgg tgaagcctct   1440

aatgtagacg aatatttgtg gttaatgggt agagctaact acaagccagt tatagaaatg   1500

tgtggtggta cagaaatcgg tggtgctttt tctgctggtt catttttgca agctcaatct   1560

ttaagttctt tttcatccca atgtatgggt tgcaccttgt acatattaga taagaacggt   1620

tacccaatgc ctaaaaataa gccaggtatc ggtgaattgg cattaggtcc tgttatgttt   1680

ggtgcctcaa aaacattgtt aaacggtaat catcacgatg tctatttcaa gggtatgcca   1740

accttgaatg gtgaagtatt gagaagacat ggtgacattt tcgaattgac ctctaacggt   1800

tactaccatg cacacggtag agccgatgac actatgaaca tcggtggtat caaaattagt   1860

tctatcgaaa tcgaaagagt ctgtaatgaa gtagatgaca gagtttttga aaccactgct   1920

attggtgttc cacctttggg tggtggtcca gaacaattgg tcatattttt cgtattgaag   1980

gattcaaacg acacaaccat tgatttgaac caattgagat tatcctttaa cttgggtttg   2040

caaaagaaat tgaacccatt attcaaagtt actagagttg tcccattgtc atccttacct   2100

agaactgcaa caaacaagat catgagaaga gttttgagac aacaattcag tcatttcgaa   2160

tga                                                                 2163
```

<210> SEQ ID NO 24
<211> LENGTH: 1059
<212> TYPE: DNA
<213> ORGANISM: Artificial Sequence
<220> FEATURE:
<223> OTHER INFORMATION: Codon optimized

<400> SEQUENCE: 24

```
atggcttcag aaaaggaaat aagaagagaa agattcttga acgtattccc aaagttagtt     60

gaagaattga acgctagttt gttagcttat ggtatgccta aagaagcctg cgattggtat    120

gctcactctt taaactacaa tactccaggt ggtaaattga atagaggttt gagtgtagtt    180

gatacttatg ctatcttgtc taacaaaacc gttgaacaat taggtcaaga agaatacgaa    240

aaggtcgcta tcttgggttg gtgtattgaa ttgttgcaag catacttttt ggttgccgat    300

gacatgatgg ataagtctat aacaagaaga ggtcaaccat gctggtacaa agttccagaa    360

gttggtgaaa tagccataaa tgatgctttt atgttggaag ccgctatcta taaattgttg    420

aagtcacatt tcagaaacga aaagtactac atcgatatta ccgaattatt ccacgaagtt    480

actttccaaa cagaattggg tcaattgatg gatttgataa ctgcacctga agataaagtt    540

gacttgtcaa agttttcctt gaagaaacat tcattcatcg tcacctttga aactgcttat    600

tactccttct atttgccagt cgccttggct atgtacgtag ctggtattac tgatgaaaaa    660

gacttgaagc aagcaagaga tgttttgata cctttgggtg aatacttcca aatccaagat    720
```

```
gactacttag actgtttcgg tactccagaa caaataggta aaatcggtac agatattcaa    780

gacaataagt gcagttgggt tattaacaag gctttggaat tagcatctgc cgaacaaaga    840

aagactttgg atgaaaacta cggtaaaaag gactcagttg ctgaagcaaa gtgtaagaaa    900

atttttaatg atttgaagat tgaacaattg taccatgaat acgaagaatc catcgctaaa    960

gacttaaagg caaagattag tcaagttgat gaatcaagag gttttaaagc cgacgttttg   1020

acagctttct tgaataaggt ctacaagaga tcaaagtag                         1059
```

```
<210> SEQ ID NO 25
<211> LENGTH: 1158
<212> TYPE: DNA
<213> ORGANISM: Artificial Sequence
<220> FEATURE:
<223> OTHER INFORMATION: Codon optimized

<400> SEQUENCE: 25

atgaaccatt tgagagccga aggtcctgcc tccgtattag ccataggtac agccaaccca     60

gaaaacatat tgatccaaga tgaatttcct gattattact tcagagttac caagagtgaa    120

cacatgactc aattgaagga aaagtttaga aaaatatgtg ataagtctat gatcagaaag    180

agaaactgct tcttgaacga agaacatttg aagcaaaatc caagattggt agaacacgaa    240

atgcaaacat tggatgccag acaagacatg ttagttgtcg aagttcctaa attgggtaaa    300

gatgcttgtg caaaagccat taaggaatgg ggtcaaccaa agtcaaagat cactcatttg    360

atttttacaa gtgcatctac tacagatatg cctggtgcag actaccactg tgccaaattg    420

ttaggtttgt caccatccgt taagagagtc atgatgtatc aattaggttg ctacggtggt    480

ggtactgttt tgagaatcgc taaggatatt gcagaaaaca acaagggtgc cagagtatta    540

gctgtttgtt gcgacattat ggcttgcttg tttagaggtc caagtgattc tgacttggaa    600

ttgttagttg gtcaagctat cttcggtgac ggtgctgctg ctgttattgt tggtgcagaa    660

cctgacgaat ctgttggtga aagaccaata tttgaattag tcagtacagg tcaaaccatc    720

ttgcctaatt ctgaaggtac aattggtggt catataagag aagcaggttt gatcttcgat    780

ttgcacaaag acgttccaat gttaatctct aacaacatag aaaagtgttt gatagaagca    840

ttcactccta taggtatctc agattggaac tctattttct ggataacaca tccaggtggt    900

aaagccattt tggataaggt tgaagaaaaa ttggatttga agaaagaaaa gtttgtagat    960

agtagacatg ttttatctga acacggtaac atgtcttcat ccactgtctt gttcgtaatg   1020

gatgaattga gaaagagatc attagaagag ggtaaatcta ctactggtga cggttttgaa   1080

tggggtgtct tatttggttt cggtcctggt ttgaccgtcg aaagagtagt tgtcagatca   1140

gtaccaatta aatattag                                                 1158
```

```
<210> SEQ ID NO 26
<211> LENGTH: 315
<212> TYPE: DNA
<213> ORGANISM: Artificial Sequence
<220> FEATURE:
<223> OTHER INFORMATION: Codon optimized

<400> SEQUENCE: 26

atggccgtca agcatttgat agtattgaag tttaaagatg aaatcacaga agctcaaaag     60

gaagaatttt tcaagaccta cgttaatttg gtcaacatta tacctgctat gaaagatgta    120

tactggggta aagacgttac acaaaagaaa gaagaaggtt atacacacat tgtcgaagta    180

accttcgaat cagttgaaac tatccaagat tacatcattc atccagctca cgttggtttt    240
```

ggtgacgttt acagatcctt ctgggaaaaa ttgttgatct tcgattacac cccaagaaag 300
ttaaagccaa aataa 315

<210> SEQ ID NO 27
<211> LENGTH: 1188
<212> TYPE: DNA
<213> ORGANISM: Artificial Sequence
<220> FEATURE:
<223> OTHER INFORMATION: Codon optimized

<400> SEQUENCE: 27
atgggtttat catccgtctg tactttctcc ttccaaacta actatcatac cttattgaat 60
cctcacaaca acaatccaaa aacatcattg ttgtgttaca gacatccaaa gacacctatt 120
aagtactctt acaacaactt tccatcaaaa cattgttcaa ccaagtcctt ccacttacaa 180
aataagtgct ccgaaagttt gtctatagct aagaactcta tcagagctgc aactacaaat 240
caaactgaac cacctgaaag tgataatcac tctgttgcca caaaaatttt gaacttcggt 300
aaagcatgtt ggaagttgca aagaccatac accataatcg cttttacttc ttgtgcatgc 360
ggtttattcg gtaaagaatt gttgcataac actaacttaa tttcatggtc cttgatgttc 420
aaggcatttt tctttttagt tgccatcttg tgcatcgctt cattcaccac tacaattaat 480
caaatatacg atttgcacat cgacagaatt aacaaaccag atttgccttt ggcttcaggt 540
gaaatatccg tcaatactgc atggatcatg tctatcatag tagccttgtt cggtttgatc 600
atcacaatta aaatgaaggg tggtccattg tacatcttcg gttactgttt cggtatcttc 660
ggtggtattg tctattccgt accacctttt agatggaaac aaaaccctag tactgccttt 720
ttgttgaatt tcttagctca tatcatcaca aacttcacct tctactacgc ttcaagagct 780
gctttaggtt tgccattcga attgagacct tcattcacat ttttgttggc attcatgaaa 840
agtatgggtt ctgcattagc cttgatcaag gatgcctctg acgttgaagg tgacacaaag 900
ttcggtatta gtaccttggc ttctaagtac ggttcaagaa atttgacttt gttctgctcc 960
ggtatcgttt tgttaagtta cgtcgcagcc attttggcag gtatcatttg gccacaagcc 1020
tttaattcta acgttatgtt gttgtcacat gccatcttgg ctttctggtt gatcttgcaa 1080
actagagatt tcgctttgac aaattatgac cctgaagcag gtagaagatt ctacgagttt 1140
atgtggaaat tgtactacgc tgaatatttg gtatacgttt ttatttag 1188

<210> SEQ ID NO 28
<211> LENGTH: 1635
<212> TYPE: DNA
<213> ORGANISM: Artificial Sequence
<220> FEATURE:
<223> OTHER INFORMATION: Codon optimized

<400> SEQUENCE: 28
atgaaatgtt caactttctc cttttggttc gtatgcaaga tcatcttctt tttcttttcc 60
tttaacatcc aaacaagtat cgcaaaccca agagaaaact tttgaagtg cttctcacaa 120 tacataccta ataacgccac caatttgaag ttggtttaca ctcaaaacaa cccattgtac 180
atgtccgtct tgaacagtac aatccataat ttgagattca cttctgatac cactccaaaa 240
cctttggtca ttgtaacccc tagtcatgta tctcacatcc aaggtactat cttatgttct 300
aaaaaggttg gtttgcaaat tagaactaga tccggtggtc atgatagtga aggcatgtca 360
tacatctccc aagttccatt cgttatcgtt gatttgagaa acatgagatc aattaaaata 420

```
gacgtacact cacaaactgc ttgggttgaa gctggtgcaa cattgggtga agtatactac    480

tgggttaacg aaaagaatga aaacttatca ttggctgctg gttactgtcc aacagtttgc    540

gcaggtggtc attttggtgg tggtggttat ggtcctttaa tgagaaacta cggtttggcc    600

gctgataaca taatcgacgc tcatttggta aatgttcacg gtaaagtttt ggatagaaag    660

tctatgggtg aagacttatt ttgggctttg agaggtggtg gtgcagaatc attcggtatc    720

atagttgctt ggaagataag attagtcgca gtaccaaagt ctactatgtt ctcagtcaaa    780

aagataatgg aaatccatga attagttaaa ttggtcaata agtggcaaaa catcgcatac    840

aagtacgata aggacttgtt gttgatgact catttcatca caagaaacat caccgataac    900

caaggtaaaa ataagactgc tatccacaca tacttttctt cagttttctt gggtggtgtc    960

gattccttag tagacttgat gaataagtct tttccagaat taggtattaa gaaaactgat   1020

tgtagacaat tgtcttggat cgacaccatc atcttttatt caggtgttgt caactacgat   1080

acagacaact tcaacaaaga aatattattg gatagatccg caggtcaaaa cggtgccttt   1140

aaaattaagt tagactacgt taaaaagcca atacctgaat cagttttcgt ccaaatctta   1200

gaaaaattgt acgaagaaga tattggtgca ggcatgtacg ccttgtatcc atacggtggt   1260

ataatggacg aaatcagtga atctgccatt ccatttcctc atagagctgg tatcttatac   1320

gaattgtggt acatttgttc atgggaaaag caagaagata acgaaaagca cttaaactgg   1380

attagaaaca tctataactt catgactcca tacgtttcta aaaaccctag attggcatat   1440

ttgaactaca gagatttgga catcggtatt aacgatccaa agaatcctaa caactatacc   1500

caagctagaa tttggggtga aaaatacttc ggtaaaaatt tcgatagatt agtaaaggtt   1560

aagacattgg ttgacccaaa caacttcttt agaaacgaac aatccattcc acctttacct   1620

agacatagac actga                                                    1635
```

<210> SEQ ID NO 29
<211> LENGTH: 1638
<212> TYPE: DNA
<213> ORGANISM: Artificial Sequence
<220> FEATURE:
<223> OTHER INFORMATION: Codon optimized

<400> SEQUENCE: 29

```
atgaactgct ccgcattctc tttctggttc gtctgtaaaa taatcttctt cttcttgtcc     60

ttcaacatcc aaatctccat cgcaaatcca caagaaaact tttgaagtg tttctccgaa    120

tacatcccaa acaaccctgc taacccaaag tttatatata ctcaacatga tcaattgtac    180

atgtccgttt tgaacagtac catccaaaat ttgagattca cttctgacac tacaccaaaa    240

cctttagtca ttgttacacc ttccaatgtt agtcacattc aagcttctat attgtgctct    300

aagaaagtag gtttgcaaat cagaactaga tcaggtggtc atgatgcaga aggcatgtct    360

tacatctcac aagttccatt cgttgtagtc gatttgagaa atatgcattc cataaagatc    420

gacgttcaca gtcaaacagc atgggtagaa gcaggtgcca ccttgggtga agtttactac    480

tggatcaacg aaaagaatga aaacttttct ttccctggtg gttactgtcc aacagtaggt    540

gtcggtggtc acttttctgg tggtggttat ggtgcattga tgagaaacta cggtttagct    600

gcagataata ttatagacgc ccatttggtt aacgtagatg gtaaagtttt ggacagaaag    660

tctatgggtg aagatttgtt ttgggccata agaggtggtg gtggtgaaaa tttcggtatc    720

attgccgctt ggaaaattaa gttagtcgct gttccttcca aagtactat tttctctgtc    780

aaaaagaaca tggaaatcca cggtttggtt aagttgttta ataagtggca aaacatcgct    840
```

```
tacaagtacg ataaggactt ggttttgatg acccatttca tcactaaaaa tattacagat    900

aaccatggta aaaataagac cactgttcac ggttattttt cttcaatttt ccatggtggt    960

gtagattctt tggttgattt gatgaataag tcattcccag aattgggtat taaaaagaca   1020

gattgcaagg aattttcttg gatagacaca accatcttct attcaggtgt tgtaaacttc   1080

aacaccgcta acttcaaaaa ggaaatcttg ttggatagat ccgctggtaa aaagaccgct   1140

ttttctatta aattggacta cgttaagaaa ccaatccctg aaactgcaat ggtcaagata   1200

ttggaaaagt tgtacgaaga agatgtaggt gtcggcatgt acgttttgta tccatacggt   1260

ggtattatgg aagaaatatc tgaatcagcc ataccatttc ctcacagagc tggtatcatg   1320

tatgaattat ggtacacagc ctcatgggaa aagcaagaag ataacgaaaa gcatatcaac   1380

tgggtcagat ccgtttacaa cttcactaca ccttacgtta gtcaaaaccc aagattggca   1440

tatttgaact acagagattt ggacttaggt aaaactaacc ctgaatctcc aaataactat   1500

acacaagcaa gaatttgggg tgaaaagtac tttggtaaaa atttcaacag attagttaaa   1560

gtaaagacta aagccgaccc taacaacttt ttcagaaacg aacaatccat cccacctttg   1620

ccacctcacc accactaa                                                 1638
```

```
<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30

aggaaacgaa gataaatctc gagtttatca ttatcaatac tg                        42


<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31

ggaaaaatca gtcaaggcaa attaaagcct tcgagcg                              37


<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32

gatgggggat ccactagttc tagaatc                                         27


<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33

tgatgggctg caggaattcg atatc                                           25


<210> SEQ ID NO 34
```

<211> LENGTH: 38
<212> TYPE: DNA
<213> ORGANISM: Artificial Sequence
<220> FEATURE:
<223> OTHER INFORMATION: Primer

<400> SEQUENCE: 34
gaactagtgg atcccccatc atgaaccatt tgagagcc 38

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
tattttggct ttaactttct tggggtgtaa tc 32

<210> SEQ ID NO 36
<211> LENGTH: 43
<212> TYPE: DNA
<213> ORGANISM: Artificial Sequence
<220> FEATURE:
<223> OTHER INFORMATION: Primer

<400> SEQUENCE: 36
agaaagttaa agccaaaata atgataacga gaataatatc aag 43

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ataaacccat ggcgcagacc tgtgagag 28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
ggtctgcgcc atgggtttat catccgtc 28

<210> SEQ ID NO 39
<211> LENGTH: 41
<212> TYPE: DNA
<213> ORGANISM: Artificial Sequence
<220> FEATURE:
<223> OTHER INFORMATION: Primer

<400> SEQUENCE: 39
cgaattcctg cagcccatca gtgtctatgt ctaggtaaag g 41

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
tgatgggctg caggaattcg atatc 25

<210> SEQ ID NO 41
<211> LENGTH: 27
<212> TYPE: DNA
<213> ORGANISM: Artificial Sequence
<220> FEATURE:
<223> OTHER INFORMATION: Primer

<400> SEQUENCE: 41
gatgggggat ccactagttc tagaatc 27

<210> SEQ ID NO 42
<211> LENGTH: 33
<212> TYPE: DNA
<213> ORGANISM: Artificial Sequence
<220> FEATURE:
<223> OTHER INFORMATION: Primer

<400> SEQUENCE: 42
caccagaacc gaaggtagag gttctttgtt aac 33

<210> SEQ ID NO 43
<211> LENGTH: 45
<212> TYPE: DNA
<213> ORGANISM: Artificial Sequence
<220> FEATURE:
<223> OTHER INFORMATION: Primer

<400> SEQUENCE: 43
cgaattcctg cagcccatca ctttgatctc ttgtagacct tattc 45

<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44
gaactagtgg atcccccatc atggtttcca atcacttgtt tg 42

<210> SEQ ID NO 45
<211> LENGTH: 29
<212> TYPE: DNA
<213> ORGANISM: Artificial Sequence
<220> FEATURE:
<223> OTHER INFORMATION: Primer

<400> SEQUENCE: 45
ctctaccttc ggttctggtg tataagtcg 29

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
gatccactag ttctagaatc cg 22

<210> SEQ ID NO 47
<211> LENGTH: 35
<212> TYPE: DNA
<213> ORGANISM: Artificial Sequence

```
<220> FEATURE:
<223> OTHER INFORMATION: Primer

<400> SEQUENCE: 47

tctagaacta gtggatcatg aaccatttga gagcc                              35


<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48

tcgttatcac tttcttgggg tgtaatcg                                      28


<210> SEQ ID NO 49
<211> LENGTH: 36
<212> TYPE: DNA
<213> ORGANISM: Artificial Sequence
<220> FEATURE:
<223> OTHER INFORMATION: Primer

<400> SEQUENCE: 49

ccaagaaagt gataacgaga ataatatcaa gaatac                             36


<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50

aggtcgacgg tatcgttaaa taaaaacgta taccaaatat tcag                    44


<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51

cgataccgtc gacctcga                                                 18


<210> SEQ ID NO 52
<211> LENGTH: 32
<212> TYPE: DNA
<213> ORGANISM: Artificial Sequence
<220> FEATURE:
<223> OTHER INFORMATION: Primer

<400> SEQUENCE: 52

ggttaaacta gtatgggtaa aaactataag tc                                 32


<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53

gtgcccgtcg actcattcga aatgactgaa ttg                                33
```

PRODUCTION OF TETRAHYDROCANNABINOLIC ACID IN YEAST

CROSS-REFERENCE TO RELATED APPLICATIONS

This patent application is a continuation of U.S. Non-Provisional patent application Ser. No. 15/815,651, filed on Nov. 16, 2017 titled "Production of Cannabidiolic Acid in Yeast," now U.S. Pat. No. 10,093,949, issued on Oct. 9, 2018, which is a continuation of U.S. Non-Provisional patent application Ser. No. 14/795,816, filed on Jul. 9, 2015, titled "Production of Cannabinoids in Yeast," now U.S. Pat. No. 9,822,384, issued on Nov. 21, 2017, which in turn claims the benefit and priority of U.S. Provisional Patent Application Ser. No. 62/024,099, filed Jul. 14, 2014, titled "Terpenophenolic Production in Microorganisms." All of the aforementioned disclosures are hereby incorporated by reference herein in their entireties including all references and appendices cited therein.

REFERENCE TO SEQUENCE LISTINGS

The present application is filed with sequence listing(s) attached hereto and incorporated by reference, including Appendix 1B titled "Sequence IDs".

FIELD OF THE INVENTION

This invention relates to molecular biology, and more specifically to the transformation of yeast cells and the production of cannabinoids.

SUMMARY OF THE INVENTION

Exemplary embodiments provided herein include genetically engineering microorganisms, such as yeast or bacteria, to produce cannabinoids by inserting genes that produce the appropriate enzymes for the metabolic production of a desired compound.

DETAILED DESCRIPTION OF EXEMPLARY EMBODIMENTS

Figure 1:
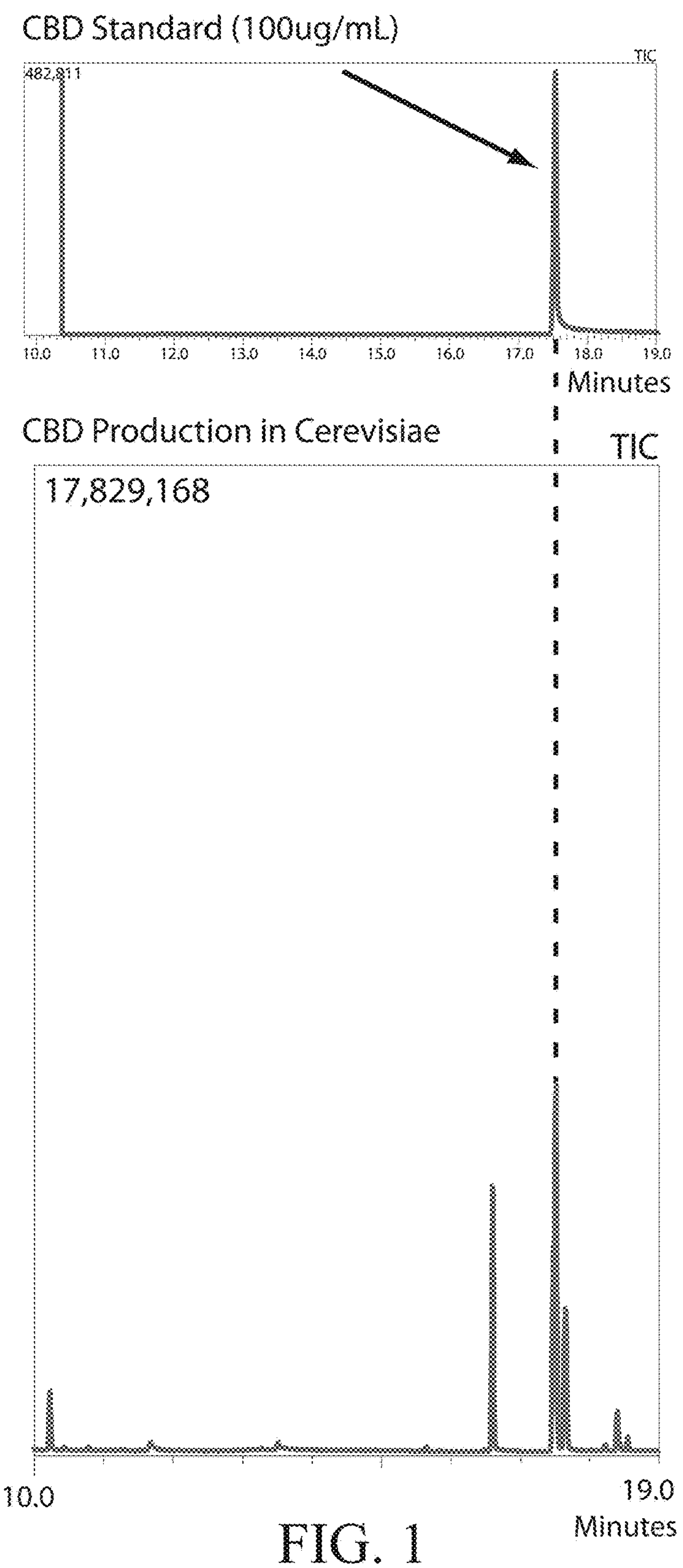
FIG. 1 shows exemplary experimental data achieved in connection with Example 1 of Appendix 1A titled "Additional Examples" for cannabidiol ("CBD")/cannabidiolic acid ("CBDA") production in *S. cerevisiae.*

The present application relates to the field of cannabinoid production in yeasts. Cannabinoids are a general class of chemicals that act on cannabinoid receptors and other target molecules to modulate a wide range of physiological behavior such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *Cannabis sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *Cannabis sativa*. In this method, the plant *Cannabis sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *Cannabis sativa*. All of these methods typically involve placing the plant, *Cannabis sativa* that contains the cannabinoids, into a chemical solution that selectively solubilizes the cannabinoids into this solution. There are various chemical solutions used to do this such as hexane, cold water extraction methods, $CO_2$ extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *Cannabis sativa*. Since there are numerous cannabinoids produced by *Cannabis sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *Cannabis sativa* extracts produces a mixture of cannabinoids and not a highly pure single pharmaceutical compound. Since many cannabinoids are similar in structure it is difficult to purify these mixtures to a high level resulting in cannabinoid contamination of the end product.

Disclosed herein are strategies for creating cannabinoids in microorganisms such as yeast and methods to produce various cannabinoids in yeast from a simple sugar source. The general methods involve genetically engineering yeast to produce various cannabinoids, where the main carbon source available to the yeast is a sugar (glucose, galactose, fructose, sucrose, honey, molasses, raw sugar, etc.). Genetic engineering of the microorganism involves inserting various genes that produce the appropriate enzymes and/or altering the natural metabolic pathway in the microorganism to achieve the production of a desired compound. Through genetic engineering of microorganisms these metabolic pathways can be introduced into these microorganisms and the same metabolic products that are produced in the plant *Cannabis sativa* can be produced by the microorganisms. The benefit of this method is that once the microorganism is produced, the production of the cannabinoid is low cost and reliable, only a specific cannabinoid is produced or a subset is produced, depending on the organism. The purification of the cannabinoid is straight forward since there is only a single cannabinoid or a selected few cannabinoids present in the microorganism. The process is a sustainable process which is more environmentally friendly than synthetic production.

FIG. 1 shows exemplary experimental data achieved in connection with Example 1 of Appendix 1A titled "Additional Examples" for cannabidiol ("CBD")/cannabidiolic acid ("CBDA") production in *S. cerevisiae.*

FIG. 1 shows gas chromatography—mass spectrometry of cannabidiol (CBD) produced in *S. cerevisiae*. After processing the yeast cells, as described in Example 1 of Appendix 1A, the whole cell ethyl acetate extract is analyzed for the presences of CBD. The samples were prepared in a way similar to that shown in Appendix A1 except that no MSTFA derivatization was used in this sample (therefore CBDA turns into CBD upon heating), the oven protocol was also slightly different than that shown in Appendix 1A. Initially, a standard CBD solution is run (100 ug/mL; TOP). After running the standard the inventors determined the run time of 17.5 minutes. After running the standard the inventors repeated the GC-MS experiment with their whole cell extract (BOTTOM). At a run time of 17.5 minutes, the inventors saw the same peak as in the standard. Mass spectrometry analysis of the peaks showed identical mass for the two samples (standard and extract) indicating the presence of CBD in their whole cell extract.

Figure 2:
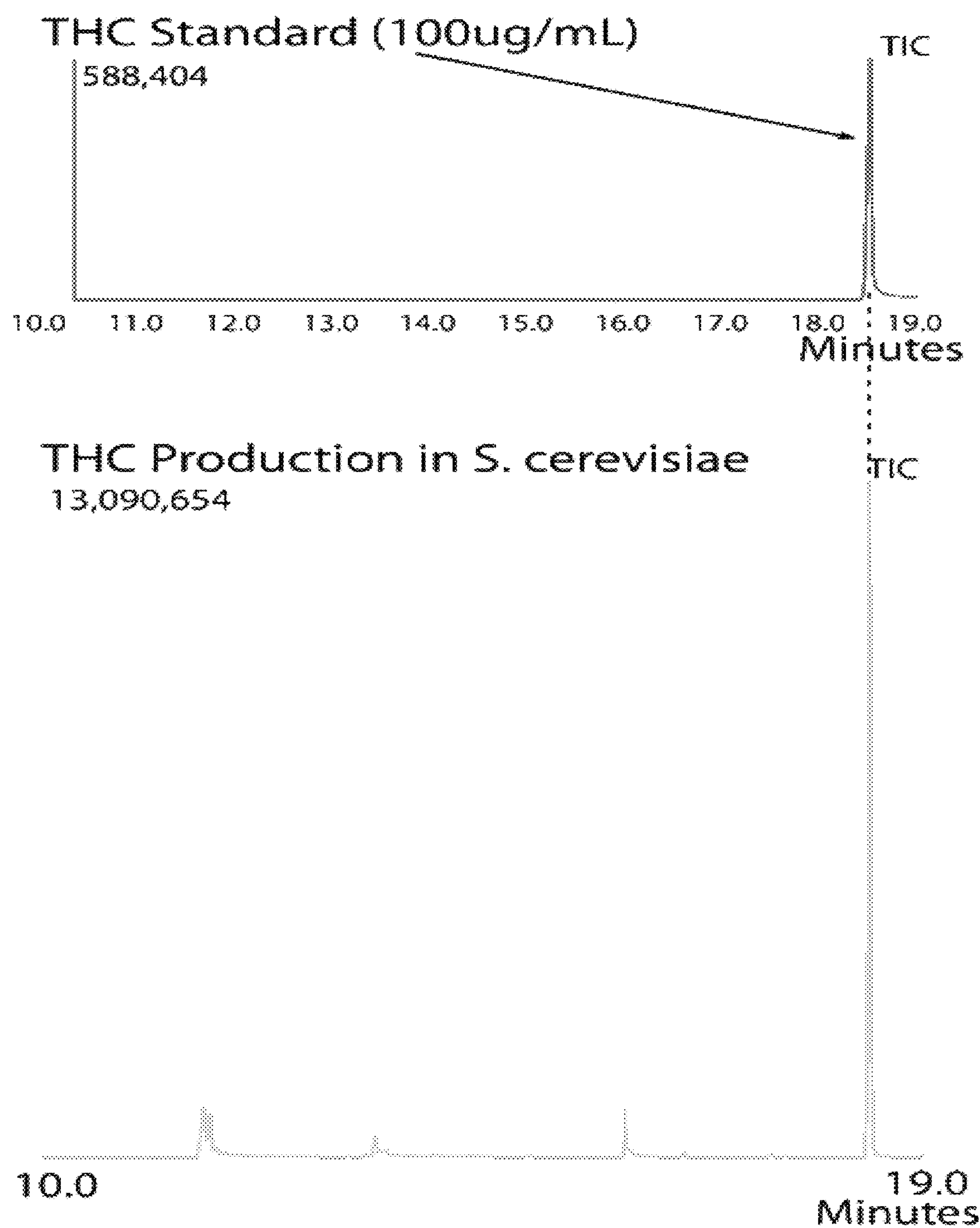
FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae.*

FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae.*

FIG. 2 shows gas chromatography—mass spectrometry of tetrahydrocannabinol (THC) produced in *S. cerevisiae*. After processing the yeast cells, as described in Example 2 of Appendix 1A, the whole cell ethyl acetate extract was analyzed for the presences of THC. The samples were prepared in a way similar to that shown in Appendix 1A except that no MSTFA derivatization was used in this sample (therefore THCA turns into THC upon heating), the oven protocol was also slightly different than that shown in Appendix 1A. Initially, a standard CBD solution was run (100 ug/mL; TOP). After running the standard the inventors determined the run time of 18.5 minutes. After running the standard the inventors repeated the GC-MS experiment with their whole cell extract (BOTTOM). At a run time of 18.5 minutes, the inventors saw the same peak as in the standard. Mass spectrometry analysis of the peaks showed identical mass for the two samples (standard and extract) indicating the presence of THC in their whole cell extract.

Figure 3:
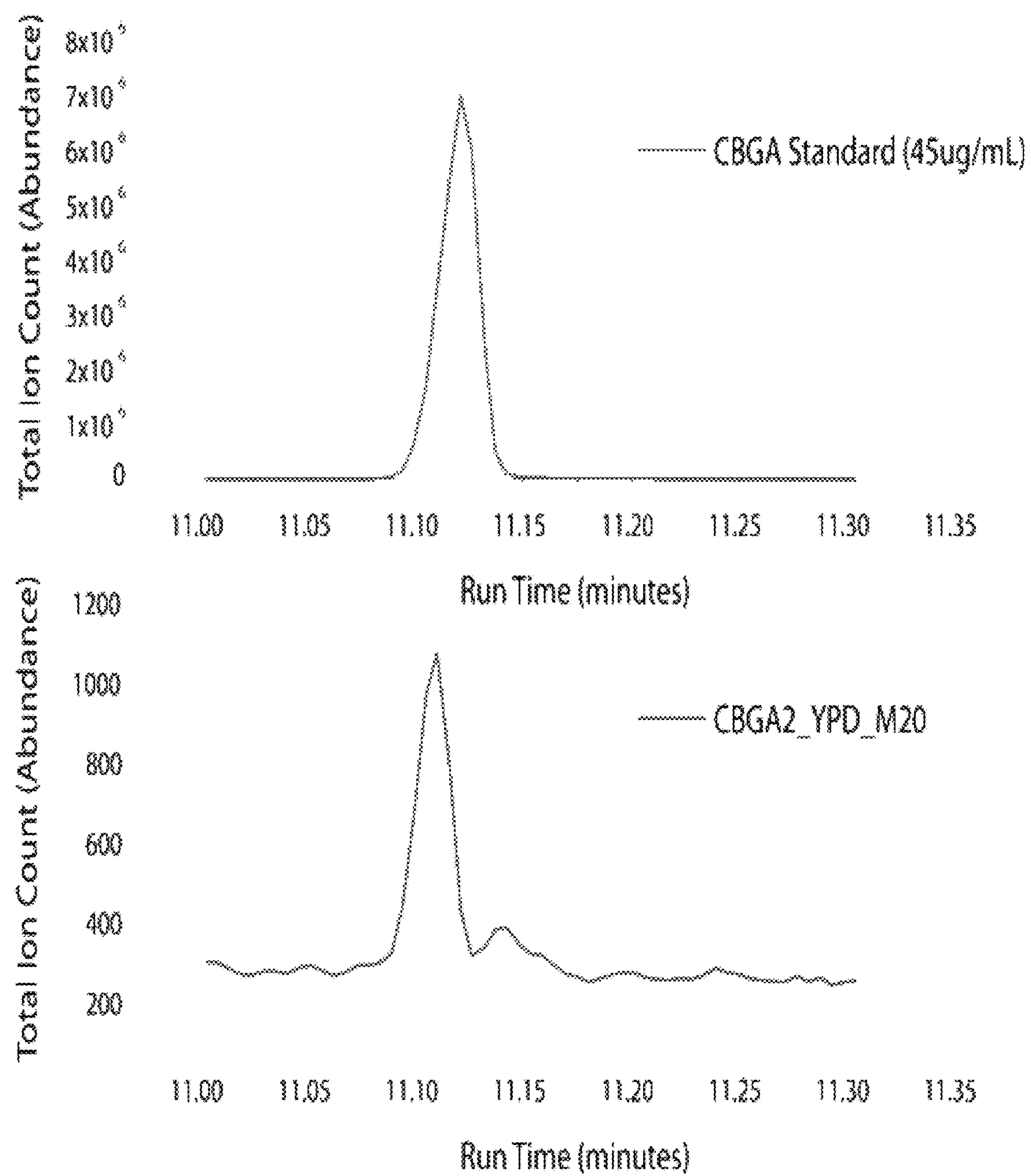
FIG. 3 shows exemplary experimental data achieved in connection with Example 3 of Appendix 1A titled "Additional Examples" for cannabigerol ("CBG")/cannabigerolic acid ("CBGA") production in *S. cerevisiae.*

FIG. 3 shows exemplary experimental data achieved in connection with Example 3 of Appendix 1A titled "Additional Examples" for cannabigerol ("CBG")/cannabigerolic acid ("CBGA") production in *S. cerevisiae.*

FIG. 3 shows gas chromatography—mass spectrometry of cannabigerolic acid (CBGA) produced in *S. cerevisiae*. After processing the yeast cells, as described in Example 3 of Appendix 1A, the whole cell ethyl acetate extract was analyzed for the presences of CBGA. The samples were prepared in a way as described in Appendix 1A, but the oven protocol was also slightly different than that shown in Appendix 1A. Initially, a standard CBGA solution was run (45 ug/mL; TOP). After running the standard, the inventors determined the run time of 11.1 minutes. After running the standard, the inventors repeated the GC-MS experiment with their whole cell extract (BOTTOM). At a run time of 11.1 minutes, the inventors saw the same peak as in the standard. Mass spectrometry analysis of the peaks showed identical mass for the two samples (standard and extract) indicating the presence of CBGA in their whole cell extract.

Figure 4:
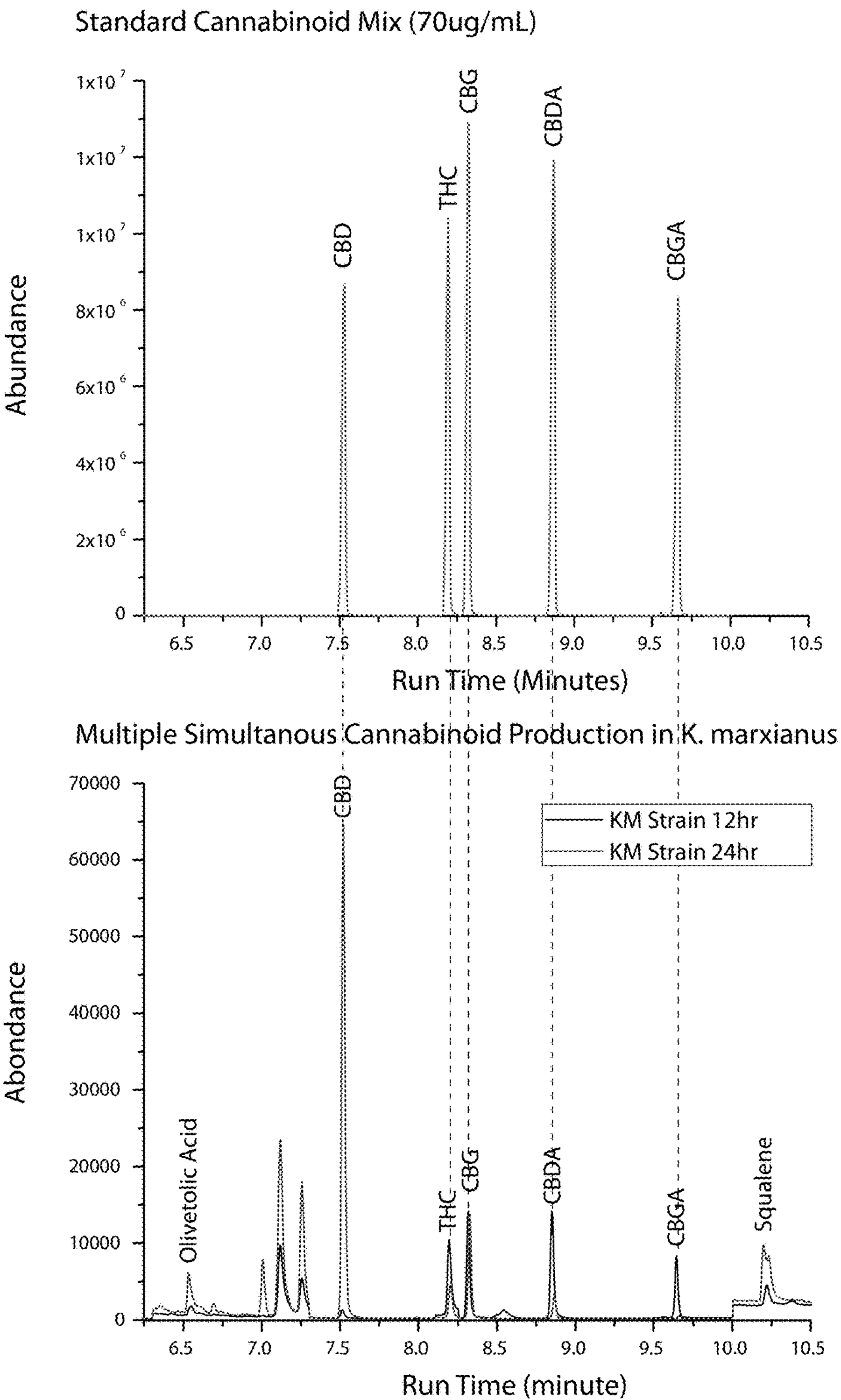
FIG. 4 shows exemplary experimental data achieved in connection with Example 4 of Appendix 1A titled "Additional Examples" for CBGA, CBDA, CBD, CBG and THC production in *K. marxianus.*

FIG. 4 shows exemplary experimental data achieved in connection with Example 4 of Appendix 1A titled "Additional Examples" for CBGA, CBDA, CBD, CBG and THC production in *K. marxianus.*

FIG. 4 shows gas chromatography—mass spectrometry of cannabinoid production (CBGA, CBDA, CBD, CBG, THC) produced in *K. marxianus*. After processing the yeast cells, as described in Example 4 of Appendix 1A, the whole cell ethyl acetate extract was analyzed for the presence of cannabinoids. The samples were prepared in a way as described in Appendix 1A, but the oven protocol was also slightly different than that shown in Appendix 1A. Initially, a standard solution containing CBD, CBG, THC, CBDA, and CBGA was run (70 ug/mL each; TOP). After running the standard, the inventors determined the run time for each compounds. After running the standard, the inventors repeated the GC-MS experiment with their whole cell extract (BOTTOM). At each run time the inventors saw the same peaks as in the standard. Mass spectrometry analysis of the peaks showed identical mass for the two samples (standard and extract) indicating the presence of cannabinoids in their whole cell extract.

Figure 5:
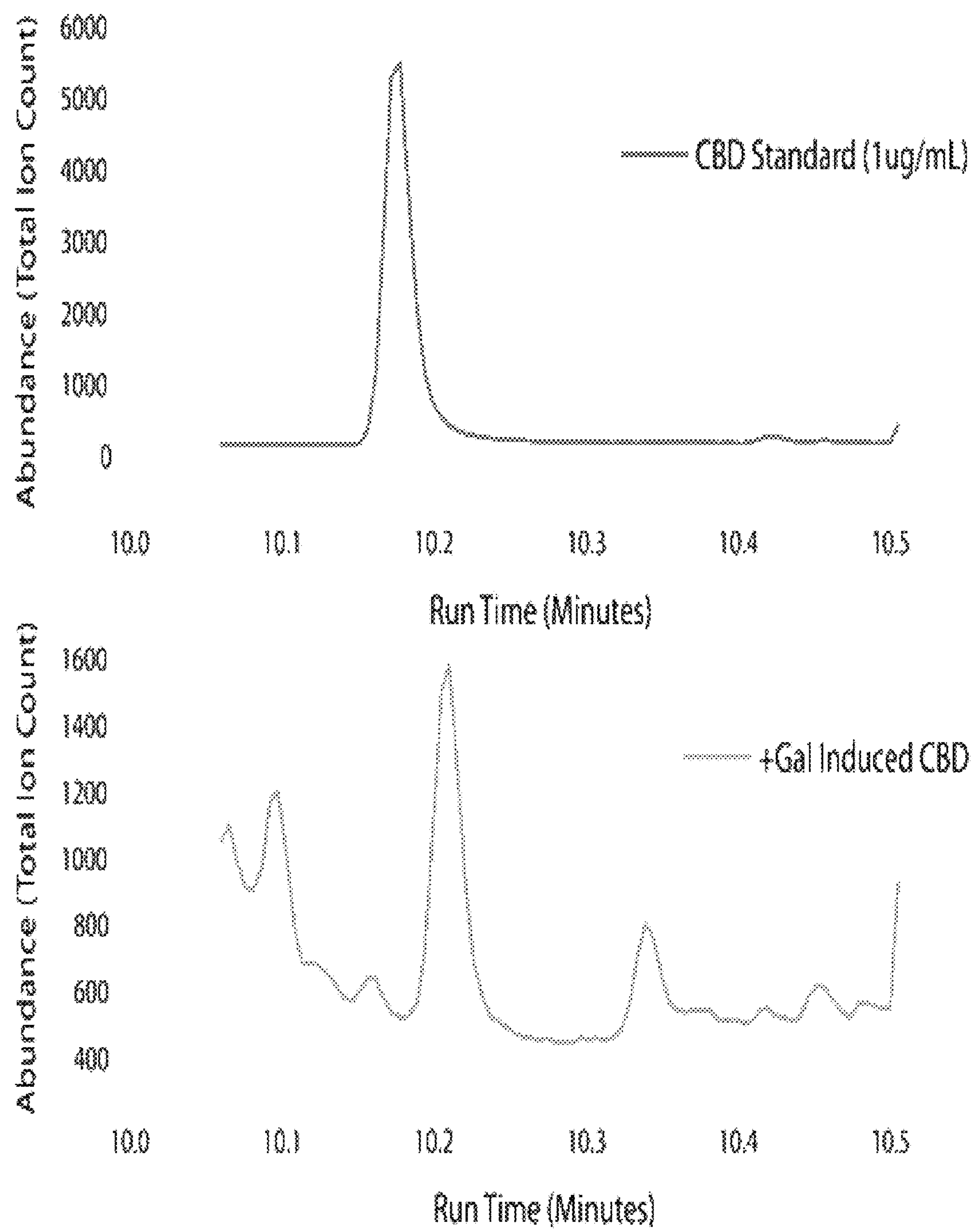
FIG. 5 show exemplary experimental data achieved in connection with Example 5 of Appendix 1A titled "Additional Examples" for galactose induced CBD production in *S. cerevisiae.*

FIG. 5 show exemplary experimental data achieved in connection with Example 5 of Appendix 1A titled "Additional Examples" for galactose induced CBD production in *S. cerevisiae.*

FIG. 5 shows gas chromatography—mass spectrometry of induced cannabidiol (CBD) production in *S. cerevisiae*. After processing yeast cells, as described in Example 5 of Appendix 1A, the whole cell ethyl acetate extract was analyzed for the presences of CBD. The samples were prepared in a way as described in Appendix 1A. Initially, a standard solution containing CBD was run (1 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Figure 6:
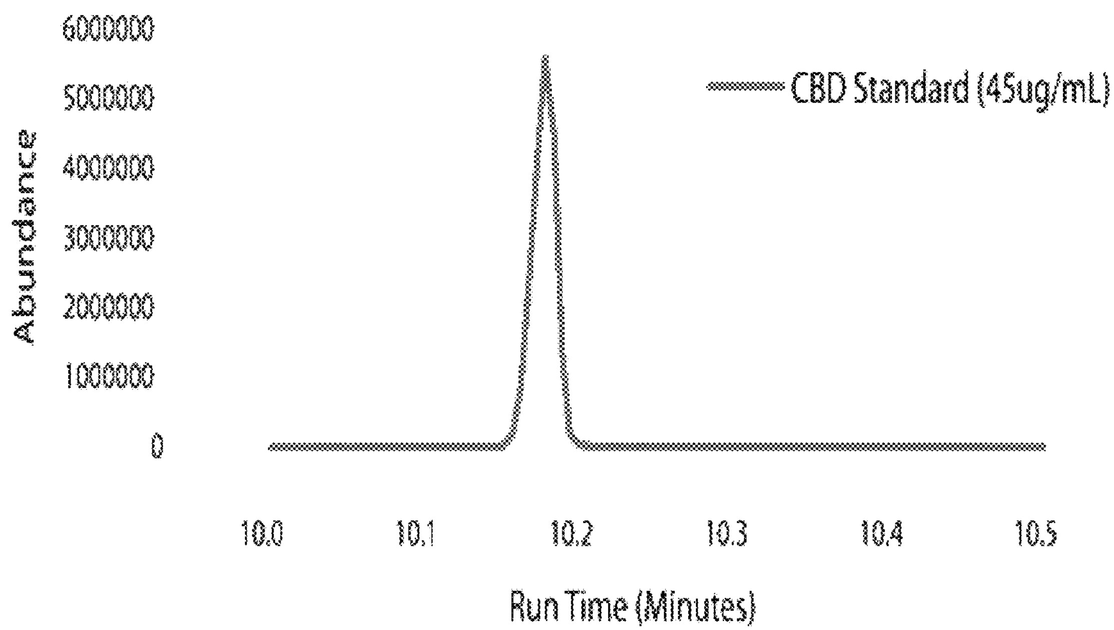
FIG. 6 shows exemplary experimental data achieved in connection with Example 6 of Appendix 1A titled "Additional Examples" for secretion of CBD into media by *S. cerevisiae.*
Figure 6:
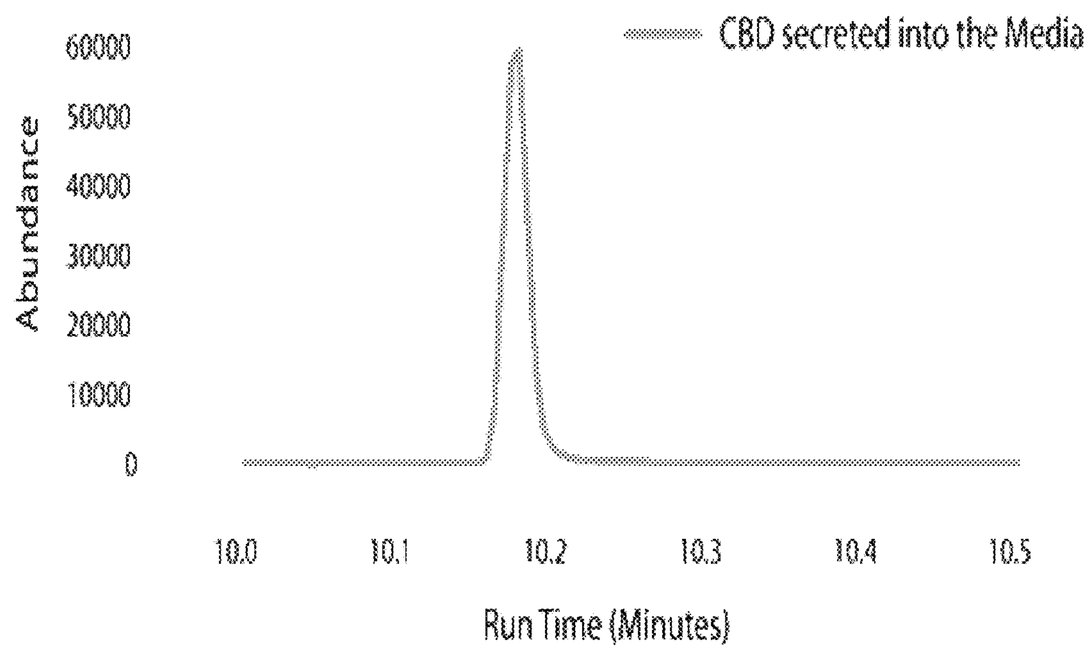

FIG. 6 shows exemplary experimental data achieved in connection with Example 6 of Appendix 1A titled "Additional Examples" for secretion of CBD into media by *S. cerevisiae.*

FIG. 6 shows gas chromatography—mass spectrometry of induced cannabidiol production (CBD) produced in *S. cerevisiae* and secreted into the media. After processing the growth media, as described in Example 6 of Appendix 1A, the media ethyl acetate extract was analyzed for the presence of CBD. The samples were prepared in a way as described in Appendix 1A. Initially, a standard solution containing CBD was run (45 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Biosynthetic Production of Cannabidiolic Acid (CBDA) in *S. cerevisiae.*

Through genetic engineering the inventors have reconstituted the cannabidiolic acid (CBDA) metabolic pathway found in *Cannabis sativa* into *S. cerevisiae* (a species of yeast).

Producing CBGA is an initial step in producing many cannabinoids from *Cannabis sativa* in *S. cerevisiae*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Figure 7:
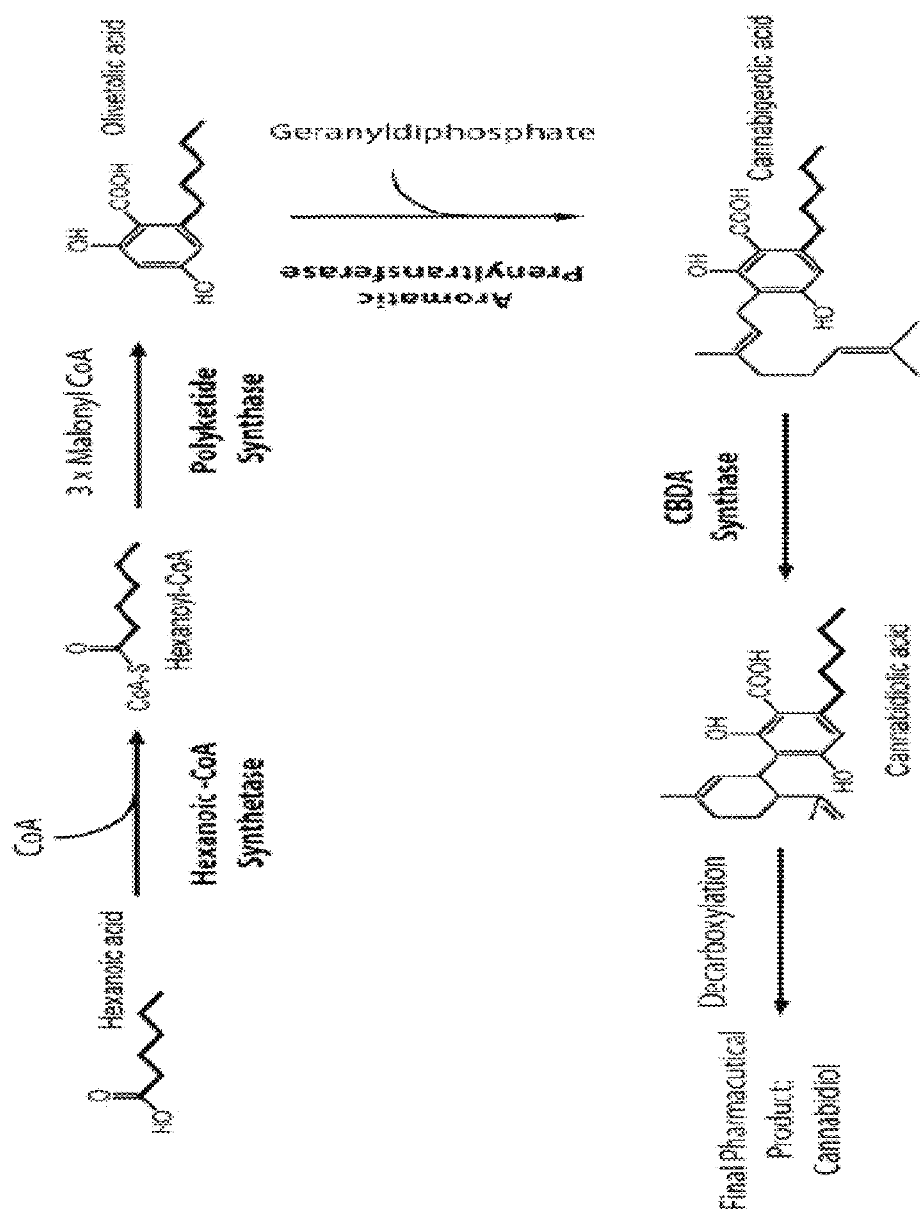
FIG. 7 shows an exemplary metabolic pathway for the production of cannabinoids by *Cannabis sativa.*

FIG. 7 shows an exemplary metabolic pathway for the production of cannabinoids by *Cannabis sativa.*

The biosynthetic route for the production of cannabidiolic acid in *Cannabis sativa* is shown in FIG. 7. The pathway begins with the conversion of Hexanoic acid (a simple fatty acid) to Hexanoyl-CoA by Hexanoyl-CoA Synthetase. Hexanoyl-CoA is converted to Oleviolic acid (OA), a polyketide, by a Polyketide synthase. OA is then prenylated with the monoterpene geranyl diphosphate to cannabigerolic acid by an Aromatic prenyltransferase. Finally, cannabidiolic acid (CBDA) is produced by cyclizing cannabigerolic acid via CBDA synthase (CBDAs). In summary, it takes four enzymatic steps to produce CBDA from Hexanoic acid. The inventors have engineered this metabolic pathway into *S. cerevisiae* (a species of yeast) for the production of CBDA.

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, through genetic engineering many of the required enzymes can be added and the production of GPP can be increased. In order to add the required enzymes for CBDA production in yeast the inventors created plasmids that contain the essential genes in the CBDA biosynthetic pathway. The inventors have transformed these genes into *S. cerevisiae.*

Synthesis of Fusion Genes Required for CBDA Production in *S. cerevisiae.*

The genome of *Cannabis sativa* has been investigated and the acyl-activating enzymes CsAAE1 was determined to convert hexanoic acid to hexanoyl-CoA (Step 1 in FIG. 7). The inventors have overexpressed CsAAE1 in yeast while simultaneously supplementing the growth media with Hexanoic acid. By supplementing the media with hexanoic acid, the inventors ensured that the yeast have the required starting materials for the production of hexanoyl-CoA.

The next enzymatic step that was engineered into the yeast strain was for the production of Olivetolic acid (OA) from hexanoyl-CoA. This step requires the substrates hexanoyl-CoA and 3 malonyl-CoA molecules, with the malonyl-CoA molecule produced by yeast naturally. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In some embodiments, stoichiometric amounts of both of these enzymes are preferred; as it has been experimentally determined that OAC binds a chemical intermediate made by OS. In various embodiments, in order to ensure the proper amounts of OS and OAC the inventors have created a single gene that is a fusion of OS, a self cleaving T2A peptide, and the OAC gene (OS-T2A-OAC) and in certain cases an HA tag was inserted at the C-terminus of OAC to verify protein expression. This entire fusion protein was produced in yeast and the self cleaving peptide is spliced in vivo to produce OS and OAC.

The next enzymatic step requires the production of geranyl pyrophosphate (GPP). In yeast the prenyltransferace Erg20 condenses isopentenyl diphosphate (IPP) and dimethylallyl diphosphate (DMAP) to geranyl pyrophosphate (GPP) and feranyl pyrophosphate (FPP) naturally. While only these two products are produced in yeast, a greater quantity of FPP when compared to GPP is produced. More GPP is required for the production of CBDA. In order to increase the production of GPP compared to FPP the inventors inserted a mutant prenyltransferase, Erg20(K179E) in the yeast strain. This mutant has been shown to shift the ratio of GPP:FPP to 70:30. This Erg20(K179E) mutant was placed on a fusion gene with CsAAE1, the enzyme for hexanoyl-CoA, and a self-cleaving peptide, T2A (CsAAE1-T2A-Erg20(K179E). We also added a FLAG tag to the C-terminus of the Erg20p (K197E) enzyme (CsAAE1-T2A-Erg20(K179E)-FLAG) to verify expression of this fusion protein in yeast in certain yeast strains. After production in yeast the self-cleaving peptide was cut producing CsAAE1 and Erg20(K179E).

Once the inventors verified that they had enough GPP to prenylate Olivetolic acid to cannabigerolic acid the inventors inserted the aromatic prenyltransferase (CsPt1) gene into the yeast. In this final enzymatic step the inventors placed the cannabidiolic acid synthase (CBDAs) gene into yeast for the conversion of cannabigerolic acid to CBDA. Similar to the inventors' previous approach, they introduced a single gene containing CsPt1, a self-cleaving peptide T2A, CBDs, and in certain cases a MYC tag was inserted at the C-terminus of CBDs in order to verify production of each enzyme (CsPt1-T2A-CBDs-MYC).

Creation of a Stable Yeast Strain Producing the Metabolic Pathway for CBDA.

Three stable transformations of *S. cerevisiae* where created utilizing selection for leucine, uracil and tryptophan. The inventors first transformed an auxotrophic yeast strain (his3D1/leu2/trp1-289/ura3-52) with the CsAAE1-T2A-Erg20(K197E)-FLAG gene in an integrating vector. 5 μg of CsAAE1-T2A-Erg20(K197E)-FLAG in a vector containing a gene for tryptophan depletion resistance was linearized with the restriction enzyme EcoRV, transformed into chemically competent InVSc1, and grown on Yeast Nitrogen Base without amino acids and 0.5% ammonium sulfate (YNBA) agar plates supplemented with histidine, leucine, tryptophan, 1% glucose and 2% lactic acid are grown at 30° C. until colonies are formed. Any yeast colonies that did not incorporate the plasmid, that contains the CsAAE1-T2A-Erg20 (K197E)-FLAG gene died since the starting yeast strain is a tryptophan auxotroph. All colonies, with successful plasmid incorporation, where picked and grown in YNBA supplemented with histidine, leucine and uracil, 1% glucose and 2% lactic acid. All colonies were screened for protein production by taking whole cell extracts of each induced clone and the total protein was subjected to SDS-PAGE followed by western blotting against the c-terminal tag of Erg20(K197E). Positive clones where stored at −80° C. in glycerol stocks. The highest expressing clone was taken for the second transformation and was designated as VscGPHA.

Using the VscGPHA strains the inventors added 5 μg of OS-T2A-OAC-HA in the a vector containing a gene for leucine depletion resistance. This plasmid was linearized with the restriction enzyme AseI and transformed into chemically competent VscGPHA and grown on YNBA agar plates supplemented with histidine and uracil, 1% glucose and 2% lactic acid and grown at 30° C. until colonies were formed. Any yeast colonies that did not incorporate the plasmid that contains the OS-T2A-OAC-HA gene died since the VscGPHA is a leucine auxotroph. All colonies, with successful plasmid incorporation, were picked and grown in YNBA supplemented with histidine, and leucine. All colonies were screened for protein production by taking whole cell extracts of each induced clone and subjected the total protein to SDS-PAGE followed by western blotting against the c-terminal HA tag of OAC. Positive clones were stored at −80° C. in glycerol stocks. The highest expressing clone was taken for the second stable transformation and was designated VscGPHOA.

The final stable transformation was done in a similar way as the previous transformation. The CsPT-T2A-CBDAs-MYC gene was placed in the vector containing a gene for uracil depletion resistance 5 μg of this plasmid was linearized with EcorV and transformed into chemically competent VscGPHOA. Transformed VscGPHOA was grown in YNBA supplemented with histidine, 1% glucose and 2% lactic acid. Any yeast colonies that did not incorporate the plasmid that contains the CsPT-T2A-CBDAs-MYC gene died since they lacked leucine. All colonies were picked and grown in YNBA supplemented with histidine, 1% glucose and 2% lactic acid. All colonies were screened for protein production by taking whole cell extracts of each induced clone and subjecting the total protein to SDS-PAGE followed by western blotting against the c-terminal Myc tag of CBDAs. Positive clones are stored at −80° C. in glycerol stocks. The highest expressing CBDAs was taken for the final strain and designated VscCBDA.

Production of CBDA in Yeast.

To initiate the reconstituted metabolic pathway of CBDA a colony of VscCBDA was freshly streaked on a plate of a frozen glycerol stock of VscCBDA. A small culture of VscCBDA was grown in YNBA supplemented with 0.05% histidine, 1% glucose, 2% lactic acid, and 0.03% hexanoic acid overnight at 30° C. The overnight culture was transferred to 1 L of YNBA supplemented with 0.05% histidine, 1% glucose, 2% lactic acid, and 0.03% hexanoic acid and was grown at 30° C. until mid-log phase. Cells were pelleted by centrifugation then washed with 200 ml of phosphate buffered saline (PBS) and repelleted. Pelleted cells were resuspended with 1 L of YNBA supplemented with 0.05% histidine, 2% galactose, and 0.03% hexanoic acid and grown at 30° C. overnight.

Overnight 1 L cultures were pelleted by centrifugation, resuspended, washed one time in PBS and pelleted. Cell pellets were resuspended in 40% (wt/vol) KOH and 50% (vol/vol) ethanol solution and boiled for 10 minutes. Metabolite extraction was done by extracting from the boiled extracts 3 times with hexane, then 3 times with ethyl acetate. The spent supernatant broth was extracted in a similar fashion as described above. Organic phases of extracts of each sample were pooled then dried by a rotary evaporator and stored for liquid chromatography mass spectrometry (LC-MS) and gas chromatography mass spectrometry (GC-MS) analysis to confirm and quantitate how much CBDA is produced from strain VscCBDA.

Biosynthetic Production of Cannabidiolic Acid (CBDA) in *K. marxianus*.

Through genetic engineering the inventors have reconstituted the cannabidiolic acid (CBDA) metabolic pathway found in *Cannabis sativa* into *K. marxianus* (a species of yeast). Producing CBGA is an initial step in producing many cannabinoids from *Cannabis sativa* in *K. marxianus*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Synthesis of Fusion Genes Required for CBDA Production in *K. Marxianus*.

Figure 8:
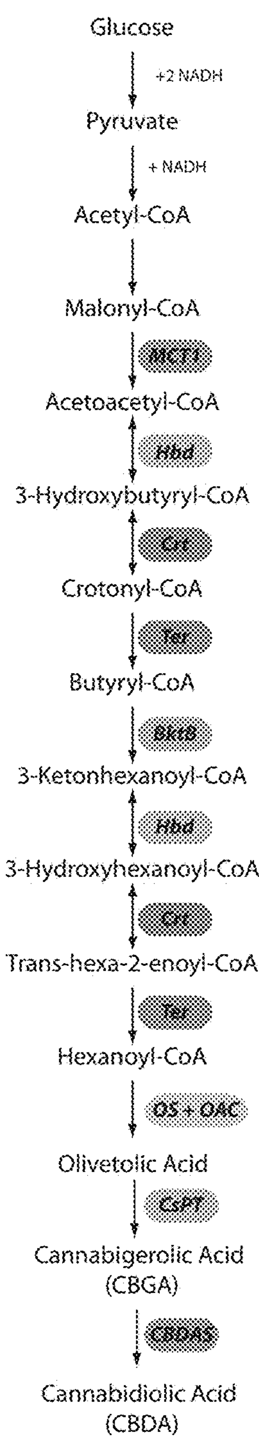
FIG. 8 shows an exemplary biosynthetic route for the production of CBDA from glucose.

FIG. 8 shows an exemplary biosynthetic route for the production of CBDA from glucose. The biosynthetic route for the production of cannabidiolic acid in *Cannabis sativa*, from glucose to CBDA is shown in FIG. 8. The pathway begins with the conversion of glucose to malonyl-CoA through a series of steps that are common to many strains of yeast. The conversion of malonyl-CoA to Acetoacetyl-CoA is conducted by the enzyme MCT1, an acyl-carrier-protein. Acetoacetyl-CoA is converted to 3-Hydroxybutyryl-CoA by the enzyme 3-hydroxybutyryl-CoA dehydrogenase (Hbd) from *Clostridium acetobutylicum*. Next, 3-Hydroxybutyryl-CoA is converted into Crotonyl-CoA by the enzyme crotonase (Crt) from *Clostridium acetobutylicum* and the conversion of Crotonyl-CoA to Butyryl-CoA is controlled by the enzyme trans-enoyl-CoA reducatase (Ter) from *Treponema denticola*. The Butyryl-CoA is converted to 3-Ketonhexanoyl-CoA by the enzyme β-ketothiolase (Bktb) from *Ralstonia Eutropha*. 3-Ketonhexanoyl-CoA is converted to 3-Hydroxyhexanoyl-CoA by the enzyme Hbd. Hydroxyhexanoyl-CoA is converted to Trans-hexa-2-enoyl-CoA by the enzyme Crt. Trans-hexa-2-enoyl-CoA is converted to Hexanoyl-CoA by the enzyme Ter. Hexanoyl-CoA, with 3 malonyl-CoAs, is converted to Oleviolic acid (OA) by a Polyketide synthase and cyclase, OA and OAC respectively. OA is then prenylated with the monoterpene geranyl diphosphate to cannabigerolic acid by an Aromatic prenyltransferase, CsPT. Finally, cannabidiolic acid (CBDA) is produced by cyclizing cannabigerolic acid via CBDA synthase (CBDAS). We have engineered this metabolic pathway into *K. marxianus* (a species of yeast) for the production of CBDA (FIG. 8).

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, the inventors through genetic engineering created many of the required enzymes that can be added so the production of GPP was increased. In order to add the required enzymes for CBDA production in yeast the inventors created plasmids that contain the essential genes in the CBDA biosynthetic pathway. The inventors have transformed these genes into *K. marxianus.*

Creation of a Stable *K. marxianus* Strain Producing the Metabolic Pathways for Hexonyl-coA and CBDA.

Two stable transformations of *K. marxianus* were created utilizing selection for uracil and G418 (Geneticin). The inventors first transformed an auxotrophic *K. marxianus* strain (ATCC 17555 KM5) with 5 different genes needed to produce high levels of hexanoyl-CoA. After functional conformation of the genes required for hexanoyl-CoA the inventors did a second transformation with the genes responsible for CBDA production. The molecular biology methods required for biosynthetic production of CBDA in *K. marxianus* are outlined below.

Gene names Crt, Bktb, MCT1, TeR, Hbd, Erg20p(K179E) were codon optimized, synthesized and subclonned into puc57 and p426 ATCC with the restriction enzymes SpeI and SalI.

Genes Crt, Bktb, MCT1, TeR, Hbd, and Erg20p(K179E) were amplified via PCR using the primers GPD_F and URA_R and all 6 amplicons were electroporated into *K. marxianus* ATCC 17555 KM5 at a concentration of 200 nM and selected onto yeast nitrogen base (YNB) supplemented with amino acid dropout mix (DO supplement—Ura Clonetech 630416) 2% glucose, and 2% Agar plates.

Gene integration and functional gene expression of Crt, Bktb, MCT1, TeR, Hbd, and Erg20p(K179E) was validated by genomic PCR and RT-PCR methods respectively. The final strain produced containing the functional expression of Crt, Bktb, MCT1, TeR, Hbd, and Erg20p(K179E) was labeled kMarxHex1.

Gene names CBDAs, CsPt, OS, and OAC were codon optimized and synthesized by Genscript. The codon optimized gene sequences of CBDAs and CsPt were cloned in frame with a nucleotide sequence containing a self cleaving T2A peptide and designated as CstTCbds. The codon optimized gene sequences of OS and OAC were cloned in frame with a nucleotide sequence containing a self cleaving T2A peptide and designated as OSTOc. CsTCbds and OSTOc were cloned in frame with an *S. cerevisiae* internal ribosomal entry site (IRES), Ure2, into a galactose inducible vector and the final gene sequence pcen/arsGal-OSTOc-IRES-CsTCbds plasmid can be seen below. The plasmid pcen/arsGal-OSTOc-IRES-CstTCbds was used to synthesize a functional gene fragment that expresses the enzymes CBDAs, CsPt, OS, and OAC by using the primers GalIRES_F, GalIRES_R.

The Gibson Assembly method was used to subclone the PCR fragment from [0057] into the plasmid HO-poly-KanMx4-HO (ATCC 87804) using the primers KmXIRES_F and KmXIRES_R to create the plasmid pHOOSCstKnMxHO.

The plasmid pHOOSCstKnMxHO was digested with NotI and transformed into kMarxHex1 using standard electroporation methods. The selection of stable integrants was done with yeast nitrogen base (YNB) supplemented with amino acid dropout mix (DO supplement—Ura Clonetech 630416) 2% glucose, 1 mg/ml G418 (Gibco) and 2% Agar plates.

Gene integration and functional gene expression of pHOOSCstKnMxHO validated by genomic PCR and RT-PCR methods respectively. The final strain produced containing the functional expression of Crt, Bktb, MCT1, TeR, Hbd, Erg20p(K179E) CBDAs, CsPt, OS, and OAC was labeled k.MarxCBDA.

Production of CBDA in *K. marxianus.*

To initiate the reconstituted metabolic pathway of CBDA, a colony from k.Marx CBDA was freshly streaked onto an agar plate from a frozen glycerol stock of k.Marx CBDA. A small culture of VscCBDA was grown in YNBA base (YNB) supplemented with amino acid dropout mix (DO supplement—Ura Clonetech 630416) 2% glucose, 1 mg/ml G418 (Gibco) and 2% Agar plates was grown overnight at 30° C. The overnight culture was transferred to 1 L of YNBA supplemented with base (YNB) supplemented with amino acid dropout mix (DO supplement—Ura Clonetech 630416) 2% glucose, and 1 mg/ml G418 (Gibco) and was grown at 30° C. until mid-log phase. Cells were pelleted by centrifugation then washed with 200 ml of phosphate buffered saline (PBS) and repelleted. Pelleted cells were resuspended with 1 L of YNBA supplemented with base (YNB) supplemented with amino acid dropout mix (DO supplement—Ura Clonetech 630416) 2% galactose, and 1 mg/ml G418 (Gibco) and grown at 30° C. overnight.

Processing CBDA for Analysis of Cannabinoid Production.

Overnight 1 L cultures were pelleted by centrifugation, resuspended, washed one time in PBS and pelleted. The process for extracting cannabinoids from the yeast generally follows the following basic steps:

1. Remove the yeast cells from the media by centrifugation or filtration.
2. Lysis the cells using either chemical or mechanical methods or a combination of methods. Mechanical methods can include a French Press or glass bead milling or other standard methods. Chemical methods can include enzymatic cell lysis, solvent cell lysis, or detergent based cell lysis.
3. Perform a liquid-liquid extraction of the cannabinoids form the cell lysate using the appropriate chemical solvent. An appropriate solvent is any solvent where the cannabinoids are highly soluble in this solvent and the solvent is not miscible in water. Examples of this are hexane, ethyl acetate, and cyclohexane. Preferred solvents can be straight or branched alkane chains (C5-C8) work well; mixtures of these solvents can also be use.

Protocol Used for Cannabinoid Extraction from Yeast Cell Lysate

1. After lysising the cells using any mechanical technique, add 1 mL of 4M KCl, pH2.0 to each 1 mL of cell lysate.

2. Add 1-2 mLs of ethyl acetate for each 1 mL of cell lysate.
3. Rigorously mix for 1 min.
4. Centrifuge the mixture for 5 min at 1000×g.
5. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for Cannabinoid Extraction from Growth Media (for Secreted Cannabinoid Samples)

1. Add 1 mL of ethyl acetate for every 1 mL of growth media.
2. Rigorously mix for 1 min.
3. Centrifuge the mixture for 5 min at 1000×g.
4. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for GC-MS Analysis of Cannabinoid Extracts for k.Marx CBDA

1. Remove solvent from samples under vacuum.
2. Re-suspend dry samples in either 100 uL of dry hexane or dry ethyl acetate
3. Add 20 uL of N-Methyl-N-(trimethylsilyl) trifluoroacetamide (MSTFA)
4. Briefly mix
5. Heat solution to 60° C. for 10-15 minutes
6. GC-MS Method
   a. Instrument Agilent 6890-5975 GC-MS (Model Number: Agilent 19091S-433)
   b. Column HP-5MS 5% Phenyl Methyl Siloxane
   c. OVEN:
      i.
      ii.

| | |
|---|---|
| Initial temp: 100° C. (On) | Maximum temp: 300° C. |
| Initial time: 3.00 min | Equilibration time: 0.50 min |

iii. Ramps:

| # | Rate | Final temp | Final time |
|---|---|---|---|
| 1 - | 30.00 | 280 | 1.00 |
| 2 - | 70.00 | 300 | 5.00 |
| 3 - | 0.0 (Off) | | |

iv. Post temp: 0° C.
      v. Post time: 0.00 min
      vi. Run time: 15.29 min

What is claimed is:

1. A method for making tetrahydrocannabinolic acid, the method comprising:

transforming *S. cerevisiae* with a first nucleotide sequence comprising the nucleotide SEQ. ID. NO. 9 or 2 expressing an acyl-activating enzyme and expressing a mutant prenyltransferase;

transforming the *S. cerevisiae* with a second nucleotide sequence comprising the nucleotide SEQ. ID. NO. 5 or 10 expressing olivetolic synthase and expressing olivetolic acid cyclase; and transforming the *S. cerevisiae* with a third nucleotide sequence comprising the nucleotide sequence SEQ. ID. NO. 3 expressing aromatic prenyltransferase and expressing tetrahydrocannabinolic acid synthase.

2. A method for making tetrahydrocannabinolic acid, the method comprising:

transforming *S. cerevisiae* with a first nucleotide sequence comprising the nucleotide SEQ. ID. NO. 9 or 2 expressing an acyl-activating enzyme and expressing a mutant prenyltransferase;

transforming the *S. cerevisiae* with a second nucleotide sequence comprising the nucleotide SEQ. ID. NO. 5 or 10 expressing olivetolic synthase and expressing olivetolic acid cyclase; and transforming the *S. cerevisiae* with a third nucleotide sequence comprising the nucleotide sequence SEQ. ID. NO. 19 expressing aromatic prenyltransferase and expressing tetrahydrocannabinolic acid synthase.

3. A method for making tetrahydrocannabinolic acid, the method comprising:

transforming *S. cerevisiae* with a first nucleotide sequence comprising the nucleotide SEQ. ID. NO. 1 expressing an acyl-activating enzyme;

transforming the *S. cerevisiae* with a second nucleotide sequence comprising the nucleotide SEQ. ID. NO. 24 expressing a mutant prenyltransferase;

transforming the *S. cerevisiae* with a third nucleotide sequence comprising the nucleotide sequence SEQ. ID. NO. 25 expressing olivetolic synthase;

transforming the *S. cerevisiae* with a fourth nucleotide sequence comprising the nucleotide SEQ. ID. NO. 26 expressing olivetolic acid cyclase;

transforming the *S. cerevisiae* with a fifth nucleotide sequence comprising the nucleotide SEQ. ID. NO. 27 expressing aromatic prenyltransferase; and transforming the *S. cerevisiae* with a sixth nucleotide comprising the nucleotide sequence of SEQ. ID. NO. 29 expressing tetrahydrocannabinol (“THC”) synthase.

* * * * *

UNITED STATES PATENT AND TRADEMARK OFFICE

CERTIFICATE OF CORRECTION

PATENT NO. : 10,392,635 B2
APPLICATION NO. : 16/122702
DATED : August 27, 2019
INVENTOR(S) : Jason L. Poulos and Anthony N. Farina It is certified that error appears in the above-identified patent and that said Letters Patent is hereby corrected as shown below:

On the Title Page

Item (72) correct inventor's name from "Anthony N. Farnia" to "Anthony N. Farina".

Signed and Sealed this
Twenty-eighth Day of March, 2023

Katherine Kelly Vidal

Katherine Kelly Vidal
*Director of the United States Patent and Trademark Office*